United States Patent

Nagano et al.

Patent Number: 5,834,576
Date of Patent: Nov. 10, 1998

[54] ACRYLIC ACID DERIVATIVES, METHOD FOR PREPARING THE ACRYLIC ACID DERIVATIVES, AND ACRYLIC ACID POLYMERS

[75] Inventors: Hideaki Nagano; Koichi Nakagawa; Keiji Yurugi; Mitsuaki Makino, all of Himeji; Tsuyoshi Hirata; Koichiro Nagare, both of Yokohama; Yuichi Kita, Akashi, all of Japan

[73] Assignee: Nippon Shokubai Co., Ltd., Osaka, Japan

[21] Appl. No.: 607,605

[22] Filed: Feb. 27, 1996

[30] Foreign Application Priority Data

Feb. 28, 1995 [JP] Japan .................................. 7-040619
Mar. 24, 1995 [JP] Japan .................................. 7-066300

[51] Int. Cl.$^6$ .................................................. C08F 220/64
[52] U.S. Cl. ........................ 526/318.3; 524/5; 526/240; 560/183; 562/587
[58] Field of Search .................................. 526/240, 241, 526/318.3; 562/587; 560/183

[56] References Cited

U.S. PATENT DOCUMENTS

| | | | |
|---|---|---|---|
| 3,678,093 | 7/1972 | Morita | 560/183 |
| 4,002,676 | 1/1977 | Borggrefe | 260/535 |
| 4,923,642 | 5/1990 | Rutzen | 260/404 |

FOREIGN PATENT DOCUMENTS

| | | |
|---|---|---|
| 52-30489 B | 8/1977 | Japan . |
| 53-15493 B | 5/1978 | Japan . |
| 58-38380 B2 | 8/1983 | Japan . |
| 59-18338 B2 | 4/1984 | Japan . |
| 5-70408 A | 3/1993 | Japan . |
| 6-135896 A | 5/1994 | Japan . |

OTHER PUBLICATIONS

"Nissan/Blenmer Pe(Polyethylene Glycol Monometacarylate)" (Brochure of Nippon Oil & Fats Co., Ltd., pp. 1–3).
"Radical polymerization of α–(alkoxymethyl)–and α–(oligo(ethyleneoxy)methyl)acrylic esters and characterization of the resulting polymers" B. Yamada et al., *Polymer Preprints*, Japan vol. 41, No. 6 (1992) pp. 1707–1709.

"Functional Polyether Compounds", Y Tanizaki, Nippon Oil and Fats Co., Ltd., *Oil Chemistry*, vol. 31, No. 5, (1982) pp. 253–255.

*Primary Examiner*—Paul R. Michl
*Attorney, Agent, or Firm*—Kubovcik & Kubovcik

[57] ABSTRACT

A novel acrylic ester which is represented by general formula (2)

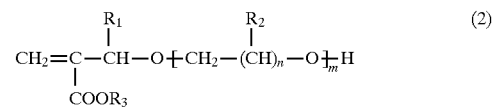

wherein $R_1$ and $R_2$ independently represent a hydrogen atom or an organic residue, $R_3$ represents an organic residue, n is a positive number among 1 to 3, and m is a positive number among 1 to 100 and which is applicable to various uses, is obtained by reacting an acrylic ester of general formula (3)

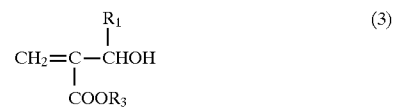

wherein $R_1$ represents a hydrogen atom or an organic residue, and $R_3$ represents an organic residue, with a cyclic ether compound of general formula (4)

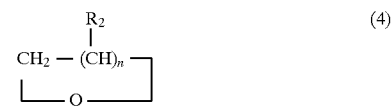

wherein $R_2$ represents a hydrogen atom or an organic residue, and n is a positive number among 1 to 3. Moreover, a novel acrylic acid derivative whose use is even wider is obtained by hydrolyzing the acrylic acid derivative.

52 Claims, 14 Drawing Sheets

ACRYLIC ACID DERIVATIVES, METHOD FOR PREPARING THE ACRYLIC ACID DERIVATIVES, AND ACRYLIC ACID POLYMERS

FIELD OF THE INVENTION

The present invention relates to acrylic acid derivatives, a method for preparing the acrylic acid derivatives, and acrylic acid polymers suitable for various uses, for example, crosslinking monomers used for crosslinking reaction of a urethane resin and a melamine resin, paint, adhesive agents, surface active agents, washing agent builder, plasticizer, solid electrolyte, antistatic monomers, anti-fogging agents, flocculating agents, dye-affinity modifier, textile modifier, textile treatment agents, dimensional stability imparting agents for wood, scarring preventing agents, hydrophilic monomers, dispersing agents, inorganic fine particle dispersing agents, drilling-mud additives, and concrete admixture.

BACKGROUND OF THE INVENTION

By copolymerizing a monomer containing a hydroxyl group with another monomer (a copolymerizable component) and then reacting the monomer with a crosslinking agent capable of reacting with the hydroxyl group, for example, an isocyanate compound and a melamine resin, the monomer is used for cold-setting paint and baking paint. (Meth)acrylic compounds to which a cyclic ether compound is added are known examples of such a monomer. Examples of such (meth)acrylic compounds are hydroxyalkyl(meth) acrylates, such as 2-hydroxyethyl(meth)acrylate, 2-hydroxy (ethoxy)ethyl(meth)acrylate, and 2-hydroxypropyl(meth) acrylate.

However, the hydroxyalkyl(meta)acrylates suffer from such a problem that the hydroxyalkyl(meth)acrylates are easily hydrolyzed under the presence of a base and a hydroxyalkyl group is eliminated. Thus, (meth)acrylic compounds which do not undergo hydrolysis and are applicable to various uses are expected.

For example, one of the uses of a conventional (meth) acrylic compound is a cement dispersing agent. The cement dispersing agent has great influences on the quality and performance of cement composition, such as cement paste, mortar, and concrete. In 1981, early deterioration of concrete structures caused social problems, and technical innovation of cement dispersing agents have been actively carried out ever since so as to meet strong demand for improved workability and durability of concrete by reducing the quantity of water per unit volume of concrete.

In order to improve the workability of concrete, a so-called plasticizing method has been used. More specifically, in this method, first, freshly mixed concrete with low fluidity (hereinafter referred to as slump) is prepared by adding an air entraining and water reducing agent (hereinafter referred to as the AE water reducing agent) in a plant. Next, after transporting the freshly mixed concrete (hereinafter referred to as the fresh concrete) to a building site by a fresh concrete transportation vehicle, the fresh concrete is plasticized by adding a plasticizer so as to increase the slump to a predetermined value.

However, in this method, since the agitation and mixing of concrete are performed while adding the plasticizer in the fresh concrete transportation vehicle, the following problems arise. For example, (1) noise and exhaust gas generated by the addition of the plasticizer to the fresh concrete, (2) the responsibility for the quality of the resulting plasticized concrete, and (3) an extreme lowering of the fluidity of the plasticized concrete with time (hereinafter referred to as the slump loss).

In order to solve such problems, manufacturers of chemical admixtures have been actively carrying out the development of so-called high-performance air entraining and water reducing agents which achieve an extremely small slump loss as well as water reducing ability and are capable of being added to fresh concrete in a fresh concrete plant.

Among the high-performance AE water reducing agents, polycarboxylic high-performance AE water reducing agents are superior because they have water reducing ability as well as slump maintaining ability. Typical examples of such polycarboxylic high-performance AE water reducing agents are: (a) copolymers formed by copolymerization of poly-alkylene glycol mono(meth)acrylate monomers, (meth) acrylic acid monomers, and other monomers capable of being copolymerized with the above monomers (see Japanese Publication for Examined Patent Application (Tokukosho) No. 59-18338/1984); and (b) copolymers formed by copolymerization of polyethylene glycol mono (meth)allylether, maleic monomers, and other monomers copolymerizable with the above monomers.

Such a copolymer contains a carboxyl group having a cement particle adhesion property and a polyalkylene glycol chain having a cement particle dispersing property (hereinafter just referred to as dispersing property) in a polymer.

However, the above-mentioned conventional polycarboxylic high-performance AE water reducing agent causes an excessive amount of entrained air in proportion to the loadings thereof. Consequently, if the loadings of the polycarboxylic high-performance AE water reducing agent increase, a desired concrete strength cannot be obtained. Therefore, there is demand for a cement dispersing agent which has superior water reducing ability and slump maintaining ability, and which is capable of reducing the entrainment of air and imparting a desired strength to a cement composition in a stable manner with small loadings.

SUMMARY OF THE INVENTION

Considering the above problems, an object of the present invention is to provide acrylic acid derivatives, a method for preparing the acrylic acid derivatives, and acrylic acid polymers suitable for various uses, for example, crosslinking monomers used for crosslinking reaction of a urethane resin and a melamine resin, paint, adhesive agents, surface active agents, washing agent builder, plasticizer, solid electrolyte, antistatic monomers, anti-fogging agents, flocculating agents, dye-affinity modifier, textile modifier, textile treatment agents, dimensional stability imparting agents for wood, scarring preventing agents, hydrophilic monomers, dispersing agents, inorganic fine particle dispersing agents, drilling-mud additives, and concrete admixture.

In order to achieve the above object, the inventors studied eagerly and invented preparation of novel acrylic acid derivatives by reacting α-hydroxyalkyl acrylic ester with a cyclic ether compound, that solve the conventional problems and are applicable to various uses. The reaction of α-hydroxyalkyl acrylic ester with a cyclic ether compound has not been known. Moreover, the inventors invented preparation of novel acrylic ester derivatives capable of being applied to various uses by hydrolysis of the acrylic acid derivatives.

The present invention relates to an acrylic acid derivative represented by general formula (1)

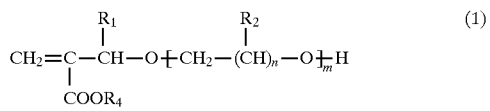

(1)

(wherein $R_1$ and $R_2$ independently represent a hydrogen atom or an organic residue, $R_4$ represents a hydrogen atom or counter-ions, n is a positive number among 1 to 3, and m is a positive number among 1 to 100).

The present invention relates to an acrylic acid derivative represented by general formula (2)

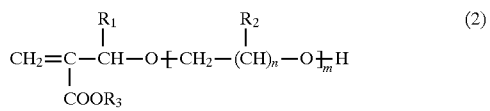

(2)

(wherein $R_1$ and $R_2$ independently represent a hydrogen atom or an organic residue, $R_3$ represents an organic residue, n is a positive number among 1 to 3, and m is a positive number among 1 to 100).

In order to achieve the above object, a method for preparing the acrylic acid derivative of general formula (1) according to the present invention includes the step of hydrolyzing the acrylic acid derivative of general formula (2).

Moreover, in order to achieve the above object, a method for preparing the acrylic acid derivative of general formula (2) of the present invention includes the step of reacting acrylic ester represented by general formula (3)

(3)

(wherein $R_1$ represents a hydrogen atom or an organic residue, and $R_3$ represents an organic residue) with a cyclic ether compound represented by general formula (4)

(4)

(wherein $R_2$ represents a hydrogen atom or an organic residue, and n is a positive number among 1 to 3).

Furthermore, the present invention relates to an acrylic acid polymer having a structural unit represented by general formula (5)

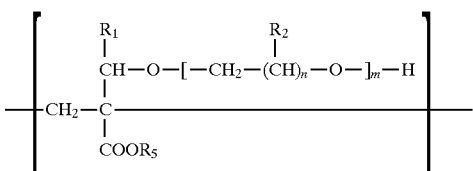

(5)

(wherein $R_1$ and $R_2$ independently represent a hydrogen atom or an organic residue, $R_5$ represents a hydrogen atom, counter-ions or an organic residue, n is a positive number among 1 to 3, and m is a positive number among 1 to 100).

With the above-mentioned structures, novel acrylic acid derivatives of general formulas (1) and (2) and novel acrylic acid polymer can be used in the same way as known monomers containing a hydroxyl group, for example, hydroxyalkyl(meth)acrylate. For instance, the acrylic acid derivatives and the acrylic acid polymer can be used as so-called adhesion improving agents for paint. Namely, by adding the acrylic acid derivatives and the acrylic acid polymer to paint, the adhesion of a coating film to a material to be coated is improved. In addition, the acrylic acid derivatives and the acrylic acid polymer are suitable as crosslinking monomers used for crosslinking reaction of a urethane resin and a melamine resin, paint, adhesive agents, surface active agents, washing agent builder, plasticizer, solid electrolyte, antistatic monomers, anti-fogging agents, flocculating agents, dye-affinity modifier, textile modifier, textile treatment agents, dimensional stability imparting agents for wood, scarring preventing agents, hydrophilic monomers, dispersing agents, inorganic fine particle dispersing agents, drilling-mud additives, and concrete admixture.

As disclosed in Japanese Publication for Unexamined Patent Application (Tokukaihei) No. 5-70408/1993, it is known that the acrylic ester represented by general formula (3), i.e., α-hydroxyalkyl acrylic ester, for use as starting material of the acrylic acid derivative of general formula (2) contains compounds, such as a dehydrated condensation product (hereinafter referred to as ether dimer) and an acetal product (hereinafter referred to as acetal dimer), as impurities.

The inventors studied impurities contained in the acrylic acid derivative of general formula (2) and found that the addition of the cyclic compound to the α-hydroxyalkyl acrylic ester causes a side reaction and increases the amounts of the ether dimer and the acetal dimer. The inventors also found that the addition of the cyclic compound to the α-hydroxyalkyl acrylic ester causes an ester interchange reaction between the hydroxyl group and ester group of the α-hydroxyalkyl acrylic ester or the acrylic acid derivative of general formula (2) and that a dimer bonded by ester linkage is produced as an impurity.

These impurities as crosslinking components have at least two double bonds in a molecule. If an acrylic acid derivative containing such a crosslinking component is polymerized, a crosslinking reaction occurs and gelation may result. In order to prevent the gelation of acrylic acid polymer, it is desirable to remove the crosslinking component from the acrylic acid derivative.

The inventors eagerly studied and found that there is a difference between the solubility of the crosslinking components as impurities and that of the acrylic acid derivative in water and in solvents. In short, the inventors found that the crosslinking impurities can be separated and removed from the acrylic acid derivative by washing the acrylic acid derivative containing the crosslinking components as impurities with a specified solvent, water, or a mixture of water and the specified solvent.

In order to achieve the above object, a method for purifying acrylic acid derivatives according to the present invention includes the step of washing the acrylic acid derivative represented by general formula (2) containing crosslinking components as impurities with an organic solvent (A) in which the solubility of the crosslinking components is higher than the solubility of the acrylic acid derivative.

In this case, an organic solvent having a solubility parameter of not greater than 8.5 is preferably used as the organic solvent (A).

Another method for purifying acrylic acid derivatives according to the present invention includes the step of washing the acrylic acid derivative of general formula (2) containing crosslinking components as impurities with a washing agent (I) containing at least water.

When washing the acrylic acid derivative containing the crosslinking components as impurities with a washing agent containing at least water, it is desirable that the washing agent (I) further includes an organic solvent (B) that separates from water to form an organic solvent layer and a water layer. An organic solvent having a solubility parameter of not greater than 10 is preferably used as the organic solvent (B).

With this structure by washing an acrylic acid derivative containing crosslinking components as impurities with the washing agent (I) containing at least water so as to extract the acrylic acid derivative into a water layer, it is possible to separate and remove the crosslinking components. It is thus possible to reduce the amount of impurities, and prepare the acrylic acid derivative which is copolymerizable with another monomer in a desired ratio without causing gelation during polymerization and which is applicable to various uses.

For example, it has been known that polyethylene glycol is present as an impurity in polyethylene glycol mono(meth) acrylate formed by addition of ethylene oxide to (meth) acrylic acid. The reasons for the presence of the impurity in the polyethylene glycol mono(meth)acrylate are: (1) addition of ethylene oxide to water in the (meth)acrylic acid as starting material; and (2) formation of polyethylene glycol and polyethylene glycol di(meth)acrylate by an ester interchange reaction in the polyethylene glycol di(meth)acrylate occurred as a side reaction by the addition of the ethylene oxide to the (meth)acrylic acid.

The inventors found as a result of study that polyalkylene glycol such as polyethylene glycol is formed by the influence of water in the starting material during the preparation of the acrylic acid derivative of general formula (2) by addition of cyclic ether to α-hydroxyalkyl acrylic ester in the same manner as in the addition of ethylene oxide to the (meth)acrylic acid. The inventors also found that a dimer bonded by ester linkage is obtained as a by-product by an ester interchange reaction between a hydroxyl group and an ester group of the α-hydroxyalkyl acrylic ester or the acrylic acid derivative of general formula (2) and that alcohol such as ethanol is separated from the α-hydroxyalkyl acrylic ester or the acrylic acid derivative and a reaction in which the cyclic ether is added to the alcohol occurs. Moreover, the α-hydroxyalkyl acrylic ester causes a dehydrating reaction between two molecules, and ether dimer and water are generated. Furthermore, the cyclic ether is also added to water, and polyethylene glycol is generated. The alcohol generated by these reactions is a non-polymerizable impurity.

A compound having polymerizable vinyl group and hydroxyl group in a molecule is usually used as urethane crosslinking monomer or melamine crosslinking monomer. However, for example, when the compound is reacted with an isocyanate compound and the product of the reaction is used as urethane acrylate oligomer, if a non-polymerizable alcohol is contained as an impurity, the non-polymerizable alcohol also reacts with the isocyanate compound. Thus, in order to increase the yield of the target product, it is necessary to increase the amount of the isocyanate compound.

Therefore, when using the acrylic acid derivative represented by general formula (2) as urethane acrylate oligomer, if the non-polymerizable alcohol is present as an impurity, it is also necessary to increase the amount of the isocyanate compound.

Moreover, when carrying out crosslinking by reacting an acrylic acid polymer formed by polymerization of the acrylic acid derivative of general formula (2) with an isocyanate compound, it is necessary to increase the amount of the isocyanate compound or purify the acrylic acid polymer in order to achieve sufficient crosslinking. The reason for this is that the hydroxyl group of the non-polymerizable alcohol as an impurity has higher reactivity than the hydroxyl group in a side chain of the acrylic acid polymer. Therefore, if the acrylic acid derivative contains the non-polymerizable alcohol, the crosslinking reaction may not be performed at a low cost. In order to perform urethane crosslinking or melamine crosslinking efficiently, it is desirable to remove the non-polymerizable alcohol from the acrylic acid derivative.

The inventors studied acrylic acid derivatives of general formula (2) and found that, in an acrylic acid derivative in which the number of added moles of the cyclic ether is small, there is a difference in the solubility in water or solvents between the non-polymerizable alcohol and the acrylic acid derivative. The inventors also found the possibility of removing the non-polymerizable alcohol from the acrylic acid derivative of general formula (2) by washing the acrylic acid derivative containing the non-polymerizable alcohol as an impurity with water or a mixture of water and a specified solvent.

In order to achieve the above object, a method for purifying acrylic acid derivatives of the present invention includes the step of washing an acrylic acid derivative containing a non-polymerizable alcohol as an impurity, represented by general formula (6)

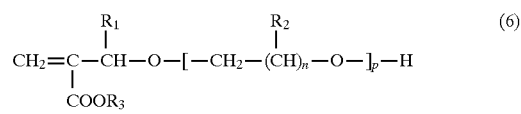

(wherein $R_1$ and $R_2$ independently represent a hydrogen atom or an organic residue, $R_3$ represents an organic residue, n is a positive number among 1 to 3, and p is a positive number among 1 to 10), with a washing agent (II) containing at least water.

It is desirable that the washing agent (II) contains water, and an organic solvent (C) that separates from water to form an organic solvent layer and a water layer. An organic solvent having a solubility parameter of not lower than 7 is preferably used as the organic solvent (C).

In this structure, by washing the acrylic acid derivative containing the non-polymerizable alcohol as an impurity with the washing agent (II) containing at least water, it is possible to extract the non-polymerizable alcohol into the water layer from the acrylic acid derivative and remove the non-polymerizable alcohol. It is thus possible to reduce the amount of impurity, and prepare the acrylic acid derivative capable of performing efficient urethane crosslinking and melamine crosslinking.

The inventors studied eagerly to achieve the above object and found that, if the acrylic acid polymer is used as a cement dispersing agent, the cement dispersing agent containing the acrylic acid polymer having a specific structural unit has superior water reducing ability and slump maintaining ability, and is capable of reducing the entrainment of air and imparting a predetermined strength to a cement composition in a stable manner with small loadings.

Namely, the present invention relates to a cement dispersing agent containing an acrylic acid polymer having a structural unit represented by general formula (7)

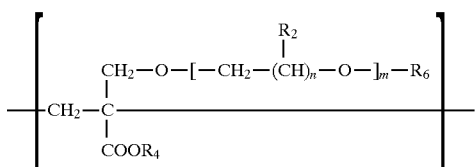

(wherein $R_2$ and $R_6$ independently represent a hydrogen atom or an organic residue, $R_4$ represents a hydrogen atom or counter-ions, n is a positive number among 1 to 3, and m is a positive number among 1 to 100 representing the average number of added moles of oxyalkylene group).

The present invention relates to a cement dispersing agent containing at least one kind of polymer selected from the group consisting of an acrylic acid polymer (D) formed by polymerization of a monomeric composition (III) containing at least an acrylic acid derivative represented by general formula (8)

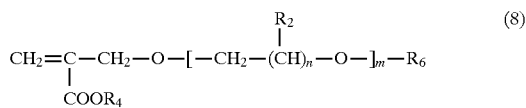

(wherein $R_2$ and $R_6$ independently represent a hydrogen atom or an organic residue, $R_4$ represents a hydrogen atom or counter-ions, n is a positive number among 1 to 3, and m is a positive number among 1 to 100 representing the average number of added moles of oxyalkylene group), an acrylic acid polymer (E) formed by neutralizing the acrylic acid polymer (D) with an alkaline substance, and an acrylic acid polymer (G) formed by hydrolyzing with an alkaline substance an acrylic acid polymer (F) obtained by polymerization of a monomeric composition (IV) containing at least an acrylic acid derivative represented by general formula (9)

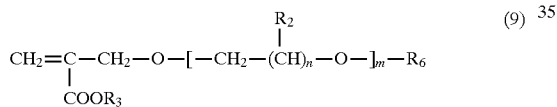

(wherein $R_2$ and $R_6$ independently represent a hydrogen atom or an organic residue, $R_3$ represents an organic residue, n is a positive number among 1 to 3, and m is a positive number among 1 to 100 representing the average number of added moles of oxyalkylene group).

The present invention also relates to a cement dispersing agent wherein the monomeric composition (III) further contains a (meth)acrylic acid monomer represented by general formula (10)

(wherein $R_7$ represents a hydrogen atom, methyl group or —$CH_2OH$ group, and $R_8$ represents a hydrogen atom or counter-ions).

Moreover, the present invention relates to a cement dispersing agent wherein the monomeric composition (IV) further contains at least one kind of (meth)acrylic acid monomer selected from the group consisting of the (meth)acrylic acid monomer represented by general formula (10) and a (meth)acrylic acid monomer represented by general formula (11)

(wherein $R_9$ represents a hydrogen atom, methyl group or —$CH_2OH$ group, and $R_{10}$ represents an organic residue).

Furthermore, the present invention relates to a cement composition including cement, water, and a cement dispersing agent containing an acrylic acid polymer having a structural unit of general formula (7)

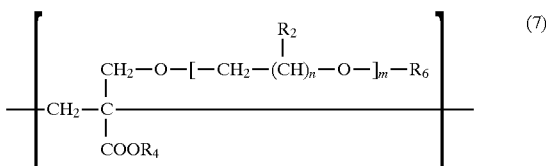

(wherein $R_2$ and $R_6$ independently represent a hydrogen atom or an organic residue, $R_4$ represents a hydrogen atom or counter-ions, n is a positive number among 1 to 3, and m is a positive number among 1 to 100 representing the average number of added moles of oxyalkylene group).

With the above structures, the cement dispersing agent and the cement composition of the present invention have water reducing ability and slump maintaining ability superior to those of conventional cement dispersing agents and cement compositions, and are capable of decreasing the amount of the cement dispersing agent with respect to cement. Thus, the cement dispersing agent and the cement composition of the present invention can reduce the entrainment of air, and impart a predetermined strength to a hardened cement composition in a stable manner. Such a structure allows a reduction in the cost of producing the cement composition.

In order to achieve the above object, a method for preparing an acrylic acid derivative represented by general formula (12)

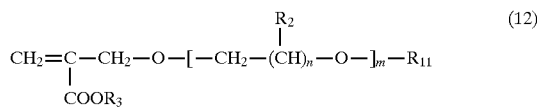

(wherein $R_2$ represents a hydrogen atom or an organic residue, $R_3$ and $R_{11}$ independently represent an organic residue, n is a positive number among 1 to 3, and m is a positive number among 1 to 100 representing the average number of added moles of oxyalkylene group) includes the step of reacting acrylic ester represented by general formula (13)

(wherein $R_3$ represents an organic residue) with a compound containing a hydroxyl group, represented by general formula (14)

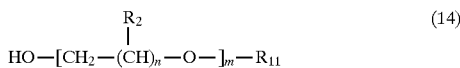

(wherein $R_2$ represents a hydrogen atom or an organic residue, $R_{11}$ represents an organic residue, n is a positive number among 1 to 3, and m is a positive number among 1 to 100) under the presence of an acid catalyst, a polymerization inhibitor, and molecular oxygen.

With this structure, a desired acrylic acid derivative can be easily prepared by reacting the acrylic ester of general formula (13) with a compound containing the hydroxyl group of general formula (14) under the presence of a polymerization inhibitor, molecular oxygen, and an acid catalyst (preferably, a protonic acid). With this method, since a hydrogen halide as a by-product is not formed by the method for preparing the acrylic acid derivative of general formula (9), it is possible to prevent corrosion of a manufacturing device and environmental distraction. Moreover, in the acrylic acid derivative prepared by the above method, since a side chain portion derived from the compound containing the hydroxyl group is bonded together with a skeleton portion derived from the acrylic ester by ether linkage, the acrylic acid derivative does not undergo hydrolysis and the side chain portion is not eliminated.

The following description will discuss the present invention in detail.

An acrylic acid derivative represented by general formula (1)

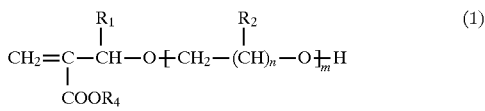

(wherein $R_1$ and $R_2$ independently represent a hydrogen atom or an organic residue, $R_4$ represents a hydrogen atom or counter-ions, n is a positive number among 1 to 3, and m is a positive number among 1 to 100) of the present invention (hereinafter just referred to as the acrylic acid compound for the sake of convenience) is not particularly limited, but is a compound wherein substituents represented by $R_1$ and $R_2$ are independently constituted by a hydrogen atom or an organic residue, a substituent represented by $R_4$ is a hydrogen atom or counter-ions, n is a positive number among 1 to 3, and m is a positive number among 1 to 100. The preferred compounds as the acrylic acid derivative are those having a hydrogen atom as $R_1$, a hydrogen atom, methyl group or ethyl group as $R_2$, and a hydrogen atom, monovalent metal, bivalent metal, ammonium group or organic amine group as $R_4$.

An acrylic acid derivative represented by general formula (2)

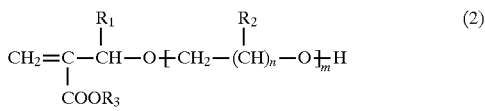

(wherein $R_1$ and $R_2$ independently represent a hydrogen atom or an organic residue, $R_3$ represents an organic residue, n is a positive number among 1 to 3, and m is a positive number among 1 to 100) of the present invention (hereinafter just referred to as the acrylic ester compound for the sake of convenience) is not particularly limited, but is a compound wherein substituents represented by $R_1$ and $R_2$ are independently constituted by a hydrogen atom or an organic residue, a substituent represented by $R_3$ is an organic residue, n is a positive number among 1 to 3, and m is a positive number among 1 to 100. The preferred compounds as the acrylic acid derivative are those having a hydrogen atom as $R_1$, a hydrogen atom, methyl group or ethyl group as $R_2$, and an alkyl group having 1 to 18 carbons as $R_3$.

An acrylic acid polymer having a structural unit represented by general formula (5)

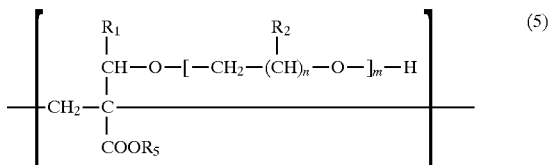

(wherein $R_1$ and $R_2$ independently represent a hydrogen atom or an organic residue, $R_5$ represents a hydrogen atom, counter-ions or an organic residue, n is a positive number among 1 to 3, and m is a positive number among 1 to 100) of the present invention is not particularly limited but is a polymer wherein substituents represented by $R_1$ and $R_2$ are independently constituted by a hydrogen atom or an organic residue, a substituent represented by $R_5$ is a hydrogen atom, counter-ions or organic residue, n is a positive number among 1 to 3, and m is a positive number among 1 to 100. The substituent represented by $R_5$ is a substituent derived from the substituents represented by $R_3$ and $R_4$ above. The number-average molecular weight of the acrylic acid polymer is within a range of from 1,000 to 1,000,000. An acrylic acid polymer having a number-average molecular weight in a range of from 10,000 to 500,000 is particularly effective because it is easily obtained by normal radical polymerization and is easy to handle.

An acrylic ester represented by general formula (3)

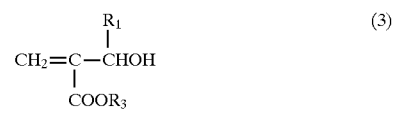

(wherein $R_1$ represents a hydrogen atom or an organic residue, and $R_3$ represents an organic residue) used as starting material in a method for preparing the acrylic ester compounds of the present invention is not particularly limited, but is a compound wherein a substituent represented by $R_1$ is a hydrogen atom or an organic residue, and a substituent represented by $R_3$ is an organic residue, i.e., α-hydroxyalkyl acrylic esters.

Examples of the substituent represented by $R_3$ are straight-chain, branched-chain and cyclic alkyl groups having 1 to 18 carbons, hydroxyalkyl groups having 1 to 8 carbons, alkoxy alkyl groups having 2 to 20 carbons, halogenated alkyl groups having 1 to 8 carbons, and aryl groups.

Examples of the acrylic ester of general formula (3) are alkyl-α-hydroxyalkyl acrylates, such as methyl-α-hydroxymethyl acrylate, ethyl-α-hydroxymethyl acrylate, n-butyl-α-hydroxymethyl acrylate, 2-ethylhexyl-α-hydroxymethyl acrylate, methyl-α-(1-hydroxyethyl) acrylate, ethyl-α-(1-hydroxyethyl) acrylate, n-butyl-α-(1-hydroxyethyl) acrylate, and 2-ethylhexyl-α-(1-hydroxyethyl) acrylate.

These acrylic esters may be used alone or in combinations of more than one kind of the acrylic esters. Among the above exemplified compounds, the preferred compounds are methyl-α-hydroxymethyl acrylate, ethyl-α-hydroxymethyl acrylate, n-butyl-α-hydroxymethyl acrylate, and 2-ethylhexyl-α-hydroxymethyl acrylate because they show satisfactory reactivity and polymerizable property with cyclic ether compounds.

Such acrylic esters can be easily obtained by a conventional known method, for example, by reacting corresponding acrylate compound and aldehyde compound under the presence of a catalyst such as a basic ion exchange resin (Japanese Publication for Unexamined Patent Application (Tokukaihei) 6-135896/1994).

A cyclic ether compound represented by general formula (4)

(wherein $R_2$ represents a hydrogen atom or an organic residue, and n is a positive number among 1 to 3) used as starting material in the method for preparing acrylic ester compounds of the present invention, is not particularly limited, but is a compound wherein the substituent represented by $R_2$ is a hydrogen atom or an organic residue and n is a positive number among 1 to 3. Namely, such a cyclic ether compound includes alkylene oxides, tetrahydrofurans, and alkyl glycidyl ethers. Examples of alkylene oxides are ethylene oxide wherein $R_2$ is a hydrogen atom and n is 1, propylene oxide wherein $R_2$ is a hydrogen atom and n is 2, and butylene oxide wherein $R_2$ is a hydrogen atom and n is 3. Examples of alkyl glycidyl ethers are aryl glycidyl ether, phenyl glycidyl ethers, and epichlorohydrin. Among these compounds, ethylene oxide, propylene oxide, butylene oxide and tetrahydrofuran are more preferred because they show excellent reaction and polymerizable properties with acrylic esters.

It is possible to use only one kind of cyclic ether compound or mix more than one kind of the cyclic ethers. Therefore, in the acrylic ester compound of general formula (2) and the acrylic acid polymer having the structural unit of general formula (5), a portion derived from the cyclic ether compound, i.e., a repeated structure of oxyalkylene group represented by —$CH_2(CHR_2)_n$—O, has the following structure. More specifically, the substituent represented by $R_2$ may be independently formed by a hydrogen atom or an organic residue in each oxyalkylene group, and these oxyalkylene groups may be bonded in a block or at random.

Such acrylic ester compounds can be easily obtained by reacting acrylic ester with a cyclic ether compound under the presence of a catalyst such as a ring scission polymerization catalyst. The method for preparing acrylic ester compounds, i.e., a method for reacting acrylic ester with a cyclic ether compound, is not particularly limited, and known methods (for example, a method for performing addition reaction of a cyclic ether compound with a hydroxyl group of conventional alcohols) can be used. The reaction of the acrylic ester with the cyclic ether compound is an exothermic reaction. Since the exotherm during the reaction is great, one example of preferred methods adds a cyclic ether compound little by little after adding a predetermined amount of a catalyst to acrylic ester.

Examples of such a catalyst are: protonic acids including mineral acids, such as hydrochloric acid, sulfuric acid, phosphoric acid and boric acid, partially neutralized salts of the mineral acids, heteropoly acids, such as tungstophosphoric acid, molybdophosphoric acid, tungstosilicic acid and phosphomolybdic acid, partially neutralized salts of the heteropoly acids, and organic sulfonic acids, such as methane sulfonic acid and paratoluene sulfonic acid; Lewis acids, such as boron fluoride, boron chloride, aluminum chloride, tin dichloride, and tin tetrachloride; and basic catalysts including metal hydroxides such as sodium hydroxide, potassium hydroxide, magnesium hydroxide and calcium hydroxide, alkali metal alkoxides such as sodium methoxide and sodium ethoxide, tertiary amines such as triethylamine and tributyl amine, and quaternary ammonium salts of the tertiary amines. The catalyst is not particularly limited. The above-mentioned catalysts may be used alone, or in combinations of more than one kind of the catalysts.

The amount of the catalyst to be added to the acrylic ester varies depending on the kind of the acrylic ester used. For example, the proportion of the catalyst to the acrylic ester is preferably within a range of from 0.001 weight percent to 10 weight percent, and more preferably within a range of from 0.01 weight percent to 5 weight percent. When the amount of the catalyst is less than 0.001 weight percent, it is hard to exhibit the catalyst activity to the full. As a result, the reaction time becomes too long, and the acrylic ester compound cannot be produced efficiently. On the other hand, if the amount of the catalyst exceeds 10 weight percent, a further improvement of the catalytic effect, for example, a shortening of the reaction time in proportion to the increase in the amount of the catalyst, cannot be expected. Namely, part of the catalyst is wasted, resulting in economical inefficiency.

The amount of the cyclic ether compound to be added to the acrylic ester varies depending on the physical properties of a desired acrylic ester compound (or acrylic acid polymer), in other words, depending on the length of a part of the acrylic ester compound derived from the cyclic ether compound, i.e., the value of m. For instance, the amount of the cyclic ether compound to be added to one mole of the acrylic ester is preferably within a range of from 1 mole to 100 moles. When the amount of the cyclic ether compound is relatively small, the flow of the polymer of the resulting acrylic ether compound becomes lower. On the other hand, when the amount of the cyclic ether compound is relatively large, the polymer of the resulting acrylic ether compound becomes softer and has higher flowability.

The reaction conditions are not particularly limited. However, the acrylic ester and the cyclic ether compound as the starting material, and the acrylic ester compound as a reaction product contain vinyl group in a molecule, and easily undergo polymerization. Therefore, when reacting the acrylic ester with the cyclic ether compound, it is desirable to add a polymerization inhibitor or molecular oxygen to the system of reaction in order to restrain the polymerization of the acrylic ester, the cyclic ether compound and the acrylic ester compound.

The polymerization inhibitor is not particularly limited. Examples are hydroquinone, hydroquinone monomethyl ether, p-benzoquinone, t-butyl catechol, and phenothiazine. These polymerization inhibitors may be used alone, or in combinations of more than one kind of the polymerization inhibitors. Although the amount of the polymerization inhibitor is not particularly limited, the proportion of the polymerization inhibitor to the acrylic ester is preferably, for example, within a range of from 0.001 weight percent to 5 weight percent. An example of the molecular oxygen is air. If air is used, it is desirable to dissolve the air in the system of reaction, i.e., the acrylic ester, or blow the air into the acrylic ester (bubbling). In order to sufficiently restrain the polymerization, it is desirable to use the polymerization inhibitor and the molecular oxygen together.

It is possible to carry out the reaction without a solvent or in the presence of a solvent. Examples of such a solvent are: ketones such as methyl ethyl ketone; ethers such as dipropyl ether; and hydrocarbons such as benzene, toluene, cyclohexane, hexane, and heptane. The solvent is not particularly limited if it does not interfere with the reaction. The amount of the solvent is not particularly limited.

Since the reaction of the acrylic ester and a cyclic ether compound is an exothermic reaction, it is desirable to proceed the reaction while maintaining the reaction temperature to be substantially uniform by removing excessive heat from the system of reaction and by adding to the system of reaction an amount of the cyclic ether compound corresponding to the exotherm removed from the system of reaction. However, it is not necessary to proceed the reaction at a substantially uniform reaction temperature.

The reaction temperature is not particularly limited. However, in order to restrain the polymerization, the reaction temperature is preferably within a range of from 0° C. to 150° C., more preferably within a range of from 30° C. to 120° C., and most preferably within a range of from 30° C. to 80° C. If the reaction temperature is lower than 0° C., the reaction time becomes too long, preventing efficient preparation of acrylic ester compounds. On the other hand, if the reaction temperature is higher than 150° C., the polymerization cannot be restrained. The reaction time may be suitably decided depending on the reaction temperature, the kinds, combinations and amounts of the acrylic ester, cyclic ether compound and catalyst. The reaction pressure is not particularly limited, and the reaction may be performed under normal pressure (atmospheric pressure), reduced pressure or increased pressure.

For example, if the catalyst is heteropoly acid and/or its partially neutralized salt, the reaction solution after the reaction contains the heteropoly acid and/or its salt, or a very small amount of by-product. In this case, after the reaction, the system of reaction, i.e., the reaction solution is contacted with an absorbent such as an acid absorbing agent to absorb the catalyst in the solution with the absorbent so as to produce an insoluble (catalyst). Subsequently, by filtering the reaction solution, the insoluble (catalyst) can be easily removed. The method for removing the catalyst is not particularly limited, and various methods can be used.

Thus, desired acrylic ester compounds, i.e., novel acrylic acid derivatives of the present invention are easily obtained by removing the catalyst from the system of reaction by a predetermined method after the reaction.

Examples of such acrylic ester compounds are: ethylene oxide adducts of α-hydroxyalkyl acrylic esters, such as methyl-2-(2-hydroxyethoxy) methyl acrylate, ethyl-2-(2-hydroxyethoxy) methyl acrylate, butyl-2-(2-hydroxyethoxy) methyl acrylate, methyl-2-[2-(2-hydroxyethoxy) ethoxy] methyl acrylate, ethyl-2-[2-(2-hydroxyethoxy) ethoxy] methyl acrylate, butyl-2-[2-(2-hydroxyethoxy) ethoxy] methyl acrylate, methyl-2-(ω-hydroxypolyethylene glycoxy) methyl acrylate, ethyl-2-(ω-hydroxypolyethylene glycoxy) methyl acrylate, butyl-2-(ω-hydroxypolyethylene glycoxy) methyl acrylate, and 2-ethylhexyl-2-(ω-hydroxypolyethylene glycoxy) methyl acrylate;

propylene oxide adducts, such as methyl-2-(2-hydroxypropoxy) methyl acrylate, ethyl-2-(2-hydroxypropoxy) methyl acrylate, butyl-2-(2-hydroxypropoxy) methyl acrylate, methyl-2-[2-(2-hydroxypropoxy) propoxy] methyl acrylate, ethyl-2-[2-(2-hydroxypropoxy) propoxy] methyl acrylate, butyl-2-[2-(2-hydroxypropoxy) propoxy] methyl acrylate, methyl-2-(ω-hydroxypolypropylene glycoxy) methyl acrylate, ethyl-2-(ω-hydroxypolypropylene glycoxy) methyl acrylate, butyl-2-(ω-hydroxypolypropylene glycoxy) methyl acrylate, and 2-ethylhexyl-2-(ω-hydroxypolypropylene glycoxy) methyl acrylate; and adducts to α-hydroxymethyl acrylic esters, such as alkylene oxides including butylene oxide, tetrahydrofuran compounds, and alkyl glycidyl ether compounds including allyl glycidyl ether, phenyl glycidyl ether and epichlorohydrin. Among these acrylic ester compounds, ethylene oxide adducts and propylene oxide adducts are most preferably used.

Like other compounds having a polymerizable vinyl group and a hydroxyl group in a molecule, the acrylic ester compounds can fit for various uses, for example, adhesion improving agents for paint, urethane crosslinking monomers, melamine crosslinking monomers, paint, adhesive agents, surface active agents, washing agent builder, plasticizer, solid electrolyte, antistatic monomers, antifogging agents, flocculating agents, dye-affinity modifier, textile modifier, textile treatment agents, dimensional stability imparting agent for wood, preventing agents, hydrophilic monomers, dispersing agents, inorganic fine particle dispersing agents, drilling-mud additives, and concrete admixture.

Among these acrylic ester compounds, compounds wherein the repeated unit represented by m is a positive number among 1 to 80 are preferred, and compounds wherein m is a positive number among 1 to 50 are more preferred.

However, such an acrylic ester compound contains a very small amount of a plurality kinds of impurities because of the effect of a side reaction occurred during the reaction. More specifically, the acrylic ester compound before purification (hereinafter just referred to as coarse acrylic ester compound) contains impurities such as crosslinking components and non-polymerizable alcohols. For instance, when an acrylic ester compound containing a crosslinking component as an impurity is polymerized, a crosslinking reaction occurs, and the possibility of gelation arises. On the other hand, if an acrylic ester compound containing non-polymerizable alcohol as an impurity is reacted with, for example, an isocyanate compound, a side reaction which is different from a target reaction occurs. Namely, the non-polymerizable alcohol also reacts with the isocyanate compound. In order to improve the yield of the target product, it is necessary to increase the amount of the isocyanate compound.

By removing the crosslinking component depending on the use, it is possible to obtain an acrylic ester compound with improved purity and to prevent the crosslinking reaction. Moreover, by removing the non-polymerizable alcohol depending on the use, it is possible to obtain an acrylic ester compound with improved purity capable of performing efficient urethane crosslinking and melamine crosslinking.

A method for removing a crosslinking component is shown below. Examples of the crosslinking component are: ether dimer having more than one double bond in a molecule, represented by general formula (15)

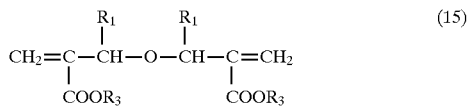

(wherein $R_1$ represents a hydrogen atom or an organic residue, and $R_3$ represents an organic residue), and acetal dimer represented by general formula (16)

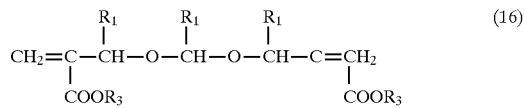

(wherein $R_3$ represents an organic residue); and a dimer bonded by ester linkage by an ester interchange reaction between a hydroxyl group and an ester group of α-hydroxyalkyl acrylic ester or acrylic ester compound (hereinafter referred to as ester-type dimer). As the ether dimer of general formula (15) and the acetal dimer of general formula (16), compounds wherein the substituent represented by $R_3$ is methyl group, ethyl group, butyl group or octyl group, are mainly listed.

The crosslinking component can be easily separated and removed by washing the acrylic ester compound containing the crosslinking component, i.e., the coarse acrylic ester compound, with the organic solvent (A) in which the solubility of the crosslinking component is higher than the solubility of the acrylic ester compound, or with the washing agent (I) containing at least water.

As the organic solvent (A), a compound whose solubility parameter is not greater than 8.5 is preferred, and a compound whose solubility parameter is within a range of from 7.0 to 8.3 is more preferred. A compound whose solubility parameter is more than 8.5 is not suitable because such a compound cannot selectively dissolve only the crosslinking component.

The solubility parameter [δ] (unit: $(cal/cm^3)^{1/2}$) is a measure of solubility, and defined by the equation $$\delta = (\Delta H - RT/V)^{1/2}$$

(wherein V is molecular volume ($cm^3$/mol), ΔH is heat of evaporation (cal/mol), R is a gas constant, and T is an absolute temperature (K)).

The organic solvent (A) is not particularly limited. Examples of the organic solvent (A) are aliphatic hydrocarbons such as hexanes (whose solubility parameter is 7.3: the solubility parameter of the following exemplified compounds will be indicated in brackets), cyclohexane (8.2), and methylcyclohexane (7.8).

A weight ratio of the organic solvent (A) used for washing the coarse acrylic ester compound to the coarse acrylic ester compound is preferably within a range of from 0.01 to 100, and more preferably within a range of from 0.1 to 10. If the weight ratio of the organic solvent (A) to the coarse acrylic ester compound is less than 0.01, the crosslinking component cannot be sufficiently removed. On the other hand, if the weight ratio of the organic solvent (A) to the coarse acrylic ester compound exceeds 100, the productivity is lowered.

A method for washing the coarse acrylic ester compound is not particularly limited, and conventionally known various methods can be used. Examples of the washing methods are agitation and line mixing, and it is desirable to select an effective method depending on the purpose. The crosslinking component is extracted and removed from the coarse acrylic ester compound by arranging the mixture to stand still to separate into two layers and by separating the layer of the organic solvent (A) as a crosslinking component layer from an acrylic ester compound layer.

If the removal of the crosslinking component is not sufficient, washing may further be performed by adding the organic solvent (A). The number of times of washing is not particularly limited, and washing may be repeated until the sufficient effect is exhibited.

After the removal of the crosslinking component, the resulting acrylic ester compound can be directly applied to various uses. However, the acrylic ester compound sometimes contains a small amount of the organic solvent (A) used for washing. Therefore, the remaining organic solvent (A) may be removed after washing depending on the use.

The method for removing the organic solvent (A) is not particularly limited, and various known methods can be used. Examples are evaporation, distillation, blowing gas which is not explosive, water extraction, and separation using a column. It is possible to recover and reuse the organic solvent (A).

Moreover, since the acrylic ester compound contains a vinyl group in a molecule, it easily undergoes polymerization. It is therefore desirable to add a polymerization inhibiter or molecular oxygen to restrain the polymerization of the vinyl group in the acrylic ester compound during washing or condensation for obtaining the acrylic ester compound.

As the polymerization inhibitor, for example, the same compounds as the polymerization inhibitors listed for the additional reaction of the acrylic ester and the cyclic ether can be used. Although the amount of the polymerization inhibitor is not particularly limited, it is preferably within a range of from 0.001 weight percent to 5 weight percent with respect to the acrylic ester compound.

As the molecular oxygen, for example, air may be used. In this case, condensation is performed while blowing the air, i.e., while performing so-called bubbling, during the removal of the organic solvent (A). In order to sufficiently restrain the polymerization, it is desirable to use both the polymerization inhibitor and the molecular oxygen.

The pressure during washing and during the removal of the organic solvent (A) is not particularly limited. Namely, washing and the removal of the organic solvent (A) may be performed under a normal pressure (atmospheric pressure), a reduced pressure or an increased pressure.

As described above, by washing the coarse acrylic ester compound containing the crosslinking component as an impurity with the organic solvent (A), it is possible to extract the crosslinking component into the layer of the organic solvent (A) from the coarse acrylic ester compound for removal. It is thus possible to reduce the amount of the impurity and prepare an acrylic ester compound capable of being polymerized with other monomers in a desired ratio without causing gelation during polymerization and being applied to various uses. Moreover, with this method, since the organic solvent (A) can selectively dissolve the crosslinking component, it is possible to remove the crosslinking component even from a non-aqueous acrylic ester compound.

The washing agent (I) used for washing the coarse acrylic ester compound is a washing agent containing at least water. Water, or a mixed solution of water and an organic solvent which is separable from a layer of water (hereinafter referred to as the organic solvent (B)) may be used as the washing agent (I).

The weight ratio of water used for washing the coarse acrylic ester compound, i.e., the amount of water contained in the washing agent (I), to the coarse acrylic ester compound is preferably within a range of from 0.01 to 100, and more preferably within a range of from 0.1 to 50 irrespectively of whether water or the mixed solution of water and the organic solvent (B) is used. If the weight ratio of water to the coarse acrylic ester compound is lower than 0.01, the yield of the resulting acrylic ester compound is lowered. On the other hand, if the weight ratio of water to the coarse acrylic ester compound exceeds 100, the productivity is lowered.

The organic solvent (B) is not particularly limited if it is an organic solvent insoluble in water. More specifically, the organic solvent (B) is preferably an organic solvent whose solubility parameter is not higher than 10, and more preferably a solvent whose solubility parameter is within a range of from 7.0 to 9.5. If the solubility parameter exceeds 10, the time taken for separating the organic solvent (B) from the layer of water increases, resulting in a lowering of the productivity.

The organic solvent (B) is not particularly limited. Examples of the organic solvent (B) are: aliphatic hydrocarbons such as hexanes (whose solubility parameter is 7.3: the solubility parameter of the following exemplified compounds will be indicated in brackets), cyclohexane (8.2), and methylcyclohexane (7.8); aromatic hydrocarbons, such as benzene (9.2), toluene (8.9), and xylene (8.8); acetates, such as ethyl acetate (9.1), and butyl acetate (8.5); propionic esters, such as ethyl propionate (8.4); and ketones, such as methyl ethyl ketone (9.3), methyl propyl ketone (8.7), and methyl isobutyl ketone (8.4). Among these organic solvents (B), solvents having a solubility parameter of not lower than 8.5, such as aromatic hydrocarbons including benzene, toluene, and xylene, and acetates, such as ethyl acetate and butyl acetate are most preferred because they can satisfactory dissolve the acrylic ester compound. Since the washing agent (I) contains the organic solvent (B) in addition to water, improved liquid separation and productivity will result.

The weight ratio of the organic solvent (B) used for washing the coarse acrylic ester compound, i.e., the amount of the organic solvent (B) contained in the washing agent (I) when the mixed solution of water and the organic solvent (B) is used as the washing agent (I), to the coarse acrylic ester compound is preferably more than 0 but not greater than 100, and more preferably more than 0 but not greater than 10. If the weight ratio of the organic solvent (B) to the coarse acrylic ester compound exceeds 100, the productivity is lowered.

A method for washing the coarse acrylic ester is not particularly limited, and conventionally known various methods can be used. Examples of the washing method are agitation and line mixing, and it is desirable to select an effective method depending on the purpose. The crosslinking component is extracted from the coarse acrylic ester compound by arranging the mixture to stand still to separate into two layers and by separating a water layer containing the acrylic ester compound from a crosslinking component layer.

If the removal of the crosslinking component is not sufficient, washing may further be performed by adding the washing agent (I). The number of times of washing is not particularly limited and may be repeated until a sufficient effect is exhibited.

After the removal of the crosslinking component, an aqueous solution of the resulting acrylic ester compound can be directly applied to various uses. However, the aqueous solution of the acrylic ester compound sometimes contains a small amount of the organic solvent (B) used for washing. Therefore, the remaining organic solvent (B) may be removed after washing depending on the use.

The method for removing the organic solvent (B) is not particularly limited, and various known methods can be used. Examples are evaporation, distillation, and blowing gas which is not explosive.

If an acrylic ester compound that is not an aqueous solution is desired, water can be removed. The method for removing water is not particularly limited. Examples are evaporation of water, and evaporation of water by adding another organic solvent which forms an azeotropic mixture with water to lower the boiling point. The used organic solvents can be recovered for reuse.

Moreover, since the acrylic ester compound contains a vinyl group in a molecule, it easily undergoes polymerization. It is therefore desirable to add a polymerization inhibiter or molecular oxygen to restrain the polymerization of the vinyl group in the acrylic ester compound during washing or condensation for obtaining the acrylic ester compound. As the polymerization inhibitor and the molecular oxygen, for example, the same compounds as the polymerization inhibitors listed for the additional reaction of the acrylic esters and the cyclic ether can be used. Although the amount of the polymerization inhibitor is not particularly limited, it is preferably within a range of from 0.001 weight percent to 5 weight percent with respect to the acrylic ester compound.

The pressure during washing and during the removal of the organic solvent (B) and water is not particularly limited. Namely, washing and the removal of the organic solvent (B) and water may be performed under a normal pressure (atmospheric pressure), a reduced pressure or an increased pressure.

As described above, by washing the coarse acrylic ester compound containing the crosslinking component as an impurity with the washing agent (I) containing at least water, it is possible to extract the crosslinking component into the water layer and to separate the crosslinking component for removal. It is thus possible to reduce the amount of the impurity, and prepare an acrylic ester compound capable of being copolymerized with other monomers in a desired ratio without causing gelation during polymerization and of being applied to various uses. Moreover, when a water-soluble acrylic ester compound is treated with the above method, the cost of purification is reduced, and a desired acrylic ester compound is prepared at a low cost.

The following description will discuss a method for removing non-polymerizable alcohols. The non-polymerizable alcohols are compounds containing non-polymerizable hydroxyl groups, such as polyalkylene glycols and polyalkylene glycol monoalkyl ethers.

Examples of the polyalkylene glycols are: glycols, such as polyethylene glycol, polypropylene glycol, polybutylene glycol; and compounds formed by water and alkyl glycidyl ether added to water.

The polyalkylene glycol monoalkyl ethers are products of reaction of alkyl alcohol and glycols such as alkyl monoglycol ether, and products of reaction of alkyl alcohol and alkyl glycidyl ether. Examples are: polyethylene glycol monoalkyl ethers, such as polyethylene glycol monomethyl ether, polyethylene glycol monoethyl ether, polyethylene glycol monobutyl ether, and polyethylene glycol mono-2-ethylhexyl ether; polypropylene glycol monoalkyl ethers, such as polypropylene glycol monomethyl ether, polypropylene glycol monoethyl ether, polypropylene glycol monobutyl ether, and polypropylene glycol mono-2-ethylhexyl ether; and polybutylene glycol monoalkyl ethers, such as polybutylene glycol monomethyl ether, polybutylene glycol monoethyl ether, polybutylene glycol monobutyl ether, and polybutylene glycol mono-2-ethylhexyl ether.

In an acrylic ester compound in which the number of added moles of the cyclic ether is small among the acrylic ester compound, the non-polymerizable alcohol can be easily separated and removed from the coarse acrylic ester compound by washing the acrylic ester compound containing the non-polymerizable alcohol as an impurity, i.e., the coarse acrylic ester compound with a washing agent (II) containing at least water. If the number of added moles of the cyclic ether becomes higher, the acrylic ester compound is also easily dissolved in water. Consequently, it is hard to separate the non-polymerizable alcohol and the coarse acrylic ether compound. Thus, by washing the coarse acrylic ester compound containing the non-polymerizable alcohol as an impurity, represented by general formula (6)

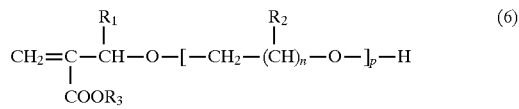

wherein $R_1$ and $R_2$ independently represent a hydrogen atom or an organic residue, $R_3$ represents an organic residue, n is a positive number among 1 to 3, and p is a positive number among 1 to 10), with the washing agent (II), the non-polymerizable alcohol is extracted into the water layer, and the non-polymerizable alcohol can be removed from the coarse acrylic ester compound.

The washing agent (II) used for washing the non-polymerizable alcohol is a washing agent containing at least water. Water, or a mixed solution of water and an organic solvent (C) which is separable from the layer of water may be used as the washing agent (II).

The weight ratio of water used for washing the non-polymerizable alcohol, i.e., the amount of water contained in the washing agent (II), to the coarse acrylic ester compound is preferably within a range of from 0.001 to 100, and more preferably within a range of from 0.01 to 10 irrespectively of whether water or the mixed solution of water and the organic solvent (C) is used. If the weight ratio of water to the coarse acrylic ester compound is lower than 0.001, the efficiency of removing the non-polymerizable is lowered. On the other hand, if the weight ratio of water to the coarse acrylic ester compound exceeds 100, the yield of the final acrylic ester compound and the productivity are lowered.

The organic solvent (C) is not particularly limited if it is an organic solvent insoluble in water. More specifically, the organic solvent (C) is preferably an organic solvent whose solubility parameter is not lower than 7, more preferably a solvent whose solubility parameter is not lower than 8, and most preferably a solvent whose solubility parameter is not lower than 8.5. If the solubility parameter is less than 7, it has high inflammability and is hard to be handled.

The organic solvent (C) is not particularly limited. Examples of the organic solvent (C) are: aliphatic hydrocarbons such as hexanes (whose solubility parameter is 7.3: the solubility parameter of the following exemplified compounds will be indicated in brackets), cyclohexane (8.2), and methylcyclohexane (7.8); aromatic hydrocarbons, such as benzene (9.2), toluene (8.9), and xylene (8.8); acetates, such as ethyl acetate (9.1), and butyl acetate (8.5); propionic esters, such as ethyl propionate (8.4); ketones, such as methyl ethyl ketone (9.3), methyl propyl ketone (8.7), and methyl isobutyl ketone (8.4); and higher alcohols, such as n-heptanol (10.6), and n-octanol (10.3). Among these organic solvents (C), the preferred solvents are those having a solubility parameter of not lower than 8.5, for example, aromatic hydrocarbons such as benzene, toluene, and xylene, and acetates, such as ethyl acetate and butyl acetate, because they can satisfactory dissolve the acrylic ester compound. Since the washing agent (II) contains the organic solvent (C) in addition to water, improved liquid separation and productivity will result.

The weight ratio of the organic solvent (C), i.e., the amount of the organic solvent (C) contained in the washing agent (II) when the mixed solution of water and the organic solvent (C) is used, to the coarse acrylic ester compound is preferably more than 0 but not greater than 100, and more preferably more than 0 but not greater than 10. If the weight ratio of the organic solvent (C) to the coarse acrylic ester compound exceeds 100, the productivity is lowered.

A method for washing the coarse acrylic ester containing the non-polymerizable alcohol is not particularly limited, and the above-mentioned washing methods can be used. In this case, however, since the non-polymerizable alcohol moves into the water layer, the non-polymerizable alcohol can be removed from the coarse acrylic ester compound by, for example, performing agitation, line mixing, arranging the mixture to stand still so as to separate the mixture into two layers and separating the water layer containing the non-polymerizable alcohol from the acrylic ester compound layer (organic solvent layer).

In this case, the number of times of washing is also not particularly limited, and washing may be repeated until a sufficient effect is exhibited. The final acrylic ester compound obtained after the removal of the non-polymerizable alcohol is directly applicable to various uses. However, the acrylic ester compound sometimes contains a small amount of the organic solvent (C) and water used for washing. Therefore, the remaining organic solvent (C) and water may be removed after washing depending on the use. The method for removing the organic solvent (C) is not particularly limited, and various known methods can be used. The same methods as mentioned above, for example, evaporation, distillation, and blowing gas which is not explosive can be used. It is possible to recover the used organic solvent (C) for reuse.

Either or both of the removal of the crosslinking component and the removal of the non-polymerizable alcohol is/are performed according to the use. The order of performing the removal of the crosslinking component and the removal of the non-polymerizable alcohol is not particularly limited. Namely, the removable of the non-polymerizable alcohol may be performed after the removal of the crosslinking component, or the removal of the crosslinking component may be performed after the removable of the non-polymerizable alcohol. Moreover, if the same organic solvent and water are used in the respective washing steps, it is possible to continuously move to the next step without performing the removal process after the washing steps.

Thus, by removing the impurity according to the necessity, a high-quality acrylic ester compound suitable for the above-mentioned various uses can be easily prepared.

The above-mentioned acrylic ester compound can be applied by itself as a novel acrylic acid derivative to various uses, and can also be used as starting material of the acrylic acid compound represented by general formula (1) above.

Namely, the acrylic acid compound represented by general formula (1) of the present invention is easily prepared by hydrolyzing the acrylic ester compound of general formula (2) above. The method for preparing the acrylic acid compound is not particularly limited. For example, a method including the step of adding the acrylic ester compound little by little to water into which a small amount of a catalyst has been added may be used.

Although the amount of water used for hydrolyzing is not particularly limited, the weight ratio of water to the acrylic ester compound is preferably within a range of from 0.001 to 1000, and more preferably within a range of from 0.01 to 100. If the weight ratio of water to the acrylic ester compound is less than 0.001, the reaction takes a long time, and hydrolyzing cannot be performed efficiently. On the other hand, if the weight ratio of water to the acrylic ester compound exceeds 1000, the productivity of the acrylic acid compound is lowered, thereby causing an industrial disadvantage.

The catalyst used for hydrolyzing is not particularly limited. Examples are: hydroxides, metal oxides and metal carbonates of alkali metal (monovalent metal) such as sodium and potassium; hydroxides, metal oxides and metal carbonates of alkaline earth metal (bivalent metal) such as magnesium and barium; ammonia; tertiary amines, such as trimethylamine and triethylamine; basic ion exchange resins; and protonic acids including mineral acids, such as hydrochloric acid, sulfuric acid, phosphoric acid and boric acid, partially neutralized salts of the mineral acids, heteropoly acids, such as tungstophosphoric acid, molybdophosphoric acid, tungstosilicic acid and phosphomolybdic acid, partially neutralized salts of the heteropoly acids, organic sulfonic acids, such as methanesulfonic acid and paratoluene sulfonic acid, and acid ion exchange resins.

Although the amount of the catalyst is not particularly limited, it is preferably within a range of from 0.01 moles to 10 moles with respect to one mole of the acrylic ester compound, and more preferably within a range of from 0.1 moles to 5 moles. If the amount of the catalyst is less than 0.01 moles, it is hard to exhibit the catalyst activity to the full. As a result, the reaction time becomes too long, causing an industrial disadvantage. On the other hand, if the amount of the catalyst exceeds 10 moles, a further improvement of the catalytic effect, for example, a shortening of the reaction time in proportion to the increase in the amount of the catalyst, cannot be expected. Namely, part of the catalyst is wasted, resulting in economical inefficiency.

The reaction temperature for hydrolyzing is preferably within a range of from 0° C. to 150° C., and more preferably within a range of from 30° C. to 120° C. If the reaction temperature is lower than 0° C., the reaction time becomes too long, causing an industrial disadvantage. On the other hand, if the reaction temperature is higher than 150° C., the polymerization of the acrylic ester compound and the acrylic acid compound as a hydrolyzed product cannot be restrained.

Since a polymerization inhibitor has already been added to the acrylic ester compound as starting material during hydrolyzing, there is no need to further add a polymerization inhibitor for the purpose of restraining polymerization. However, the polymerization inhibitor may further be added.

When further adding the polymerization inhibitor during hydrolyzing, for example, the same compounds as those listed for the method of preparing the acrylic ester compound can be used. Although the amount of the polymerization inhibitor is not particularly limited, the proportion of the polymerization inhibitor to the acrylic ester compound is preferably, for example, within a range of from 0.001 weight percent to 5 weight percent.

The reaction time in hydrolyzing may be suitably decided according to the reaction temperature, the kinds, combinations and amounts of the acrylic ester compound and the catalyst so as to complete the reaction. The reaction pressure is not particularly limited, and the reaction may be performed under normal pressure (atmospheric pressure), reduced pressure or increased pressure.

The acrylic acid polymer of the present invention is easily prepared by polymerizing the acrylic ester compound or the acrylic acid compound independently, polymerizing the acrylic ester compound and the acrylic acid compound together, or copolymerizing the acrylic ester compound and the acrylic acid compound together with a copolymerizable monomer copolymerizable with the acrylic ester compound and the acrylic acid compound.

Examples of such a copolymerizable monomer are styrene compounds, acrylonitrile, and other acrylic acid monomers. However, the copolymerizable monomer is not particularly limited if it does not deteriorate various physical properties required by the acrylic acid polymers. Namely, structural units other than the structural unit of general formula (5) for forming the acrylic acid polymer of the present invention, are not particularly limited.

More specifically, such a copolymerizable monomer includes:

(c) (meth)acrylic acid monomers represented by general formula (17)

(wherein $R_{12}$ represents a hydrogen atom, methyl group or an organic residue, and $R_{13}$ represents a hydrogen atom or counter-ions), for example, acrylic acids, methacrylic acids, α-(hydroxymethyl)acrylic acid, and monovalent metallic salts, bivalent metallic salts, ammonium salts and organic amine salts thereof;

(d) (meth)acrylic acid monomers represented by general formula (18)

(wherein $R_{14}$ represents a hydrogen atom or an organic residue, and $R_{15}$ represents an organic residue), for example, methyl acrylate, ethyl acrylate, n-propyl acrylate, isopropyl acrylate, n-butyl acrylate, isobutyl acrylate, sec-butyl acrylate, t-butyl acrylate, n-octyl acrylate, isooctyl acrylate, 2-ethylhexyl acrylate, methyl methacrylate, ethyl methacrylate, n-propyl methacrylate, isopropyl methacrylate, n-butyl methacrylate, isobutyl methacrylate, sec-butyl methacrylate, t-butyl methacrylate, n-octyl methacrylate, isooctyl methacrylate, 2-ethylhexyl methacrylate, methyl-α-(hydroxymethyl) acrylate, ethyl-α-(hydroxymethyl) acrylate, propyl-α-(hydroxymethyl) acrylate, isopropyl-α-(hydroxymethyl) acrylate, n-butyl-α-(hydroxymethyl) acrylate, isobutyl-α-(hydroxymethyl) acrylate, sec-butyl-α-(hydroxymethyl) acrylate, t-butyl-α-(hydroxymethyl) acrylate, n-octyl-α-(hydroxymethyl) acrylate, isooctyl-α-(hydroxymethyl) acrylate, and 2-ethylhexyl-α-(hydroxymethyl) acrylate;

(e) monomers other than the above-mentioned monomers (acrylic acid compounds, acrylic ester compounds, (meth)acrylic acid monomers of general formulas (17) and (18)) (hereinafter just referred to as other monomers for the sake of explanation), for example, esters formed by aliphatic alcohols having 1 to 20 carbons and (meth)acrylic acids;

polyalkylene glycol mono(meth)acrylates, such as polyethylene glycol mono(meth)acrylate, polypropylene glycol mono(meth)acrylate, polybutylene glycol mono (meth)acrylate, polyethylene glycol polypropylene glycol mono(meth)acrylate, polyethylene glycol polybutylene glycol mono(meth)acrylate, and polypropylene glycol polybutylene glycol mono(meth)acrylate;

alkoxy polyalkylene glycol (meth)acrylates, such as methoxypolyethylene glycol (meth)acrylate, ethoxypolyethylene glycol (meth)acrylate, methoxypolypropylene glycol (meth)acrylate, ethoxypolypropylene glycol (meth)acrylate, methoxypolybutylene glycol (meth)acrylate, ethoxypolybutylene glycol (meth)acrylate, methoxypolyethylene glycol polypropylene glycol (meth)acrylate, methoxypolyethylene glycol polybutylene glycol (meth)acrylate, methoxypolypropylene glycol polybutylene glycol (meth)acrylate, ethoxypolyethylene glycol polypropylene glycol (meth) acrylate, ethoxypolyethylene glycol polybutylene glycol (meth)acrylate, and ethoxypolypropylene glycol polybutylene glycol (meth)acrylate; and alkyl-α-(alkoxypolyalkylene glycoxy methyl) acrylic esters represented by general formula (19)

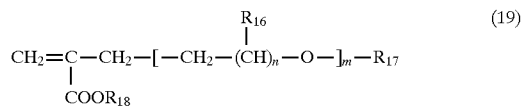

(wherein $R_{16}$ represents a hydrogen atom or a methyl group, $R_{17}$ represents a hydrogen atom, an alkyl group having 1 to 18 carbons or a phenyl group, $R_{18}$ represents an alkyl group having 1 to 18 carbons, n is zero or a positive number among 1 to 3, and m is a positive number among 1 to 100); unsaturated dicarboxylic acids such as maleic acid, fumaric acid and citraconic acid, and monoesters or diesters formed by the unsaturated dicarboxylic acids, aliphatic alcohols having 1 to 20 carbons, glycols having 2 to 4 carbons or polyalkylene glycols having 2 to 100 glycols; unsaturated amides, such as (meth)acryl amide and (meth)acrylalkyl amide; vinyl esters, such as vinyl acetate and vinyl propionate; aromatic vinyl such as styrene; unsaturated sulfonic acids, such as vinylsulfonate, (meth)acrylsulfonate, sulfoethyl(meth)acrylate, 2-methylpropane sulfonate(meth) acrylamide and styrene sulfonate, and their monovalent metallic salts, bivalent metallic salts, ammonium salts and organic amine salts; and polyfunctional monomers, such as ethylene glycol di(meth)acrylate, diethylene glycol di(meth) acrylate, triethylene glycol di(meth)acrylate, polyethylene glycol di(meth)acrylate, tripropylene glycol di(meth) acrylate, polypropylene glycol di(meth)acrylate, butanediol di(meth)acrylate, hexanediol di(meth)acrylate, trimethylolpropane tri(meth)acrylate, pentaerythritol tri(meth)acrylate, pentaerythritol tetra(meth)acrylate, dipentaerythritol penta (meth)acrylate, dipentaerythritol hexa(meth)acrylate, ether dimer of general formula (20)

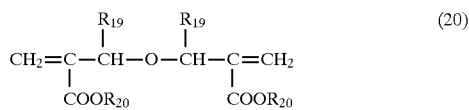

(wherein $R_{12}$ represents a hydrogen atom or an organic residue, and $R_{20}$ represents a hydrogen atom, counter ions or an organic residue), and acetal dimer of general formula (21)

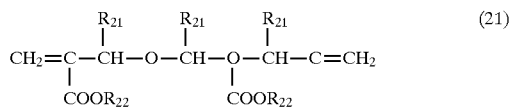

(wherein $R_{21}$ represents a hydrogen atom or an organic residue, and $R_{22}$ represents a hydrogen atom, counter ions or an organic residue. It is possible to use only one kind of the copolymerizable monomer or suitably mix more than one kind of the copolymerizable monomers.

The amounts of the acrylic acid compound, the acrylic ester compound, and the copolymerizable monomer are not particularly limited, and can be decided according to desired physical properties.

A method for preparing the acrylic acid polymer is not particularly limited, and it is possible to use various known polymerization methods, such as a method using a polymerization initiator, for example, a radical polymerization initiator, methods using radiation such as ionized radiation, electron rays, and irradiation of ultraviolet rays, and a method using heat. For instance, a desired acrylic acid polymer can be easily prepared by solution polymerization in which polymerization is performed in a solvent under the presence of the polymerization initiator, or bulk polymerization which is performed without a solvent.

The solution polymerization can be performed batch-wise or continuously. Examples of the solvent used for the solution polymerization are: water; alcohols, such as methyl alcohol, ethyl alcohol, and isopropyl alcohol; hydrocarbons, such as benzene, toluene, xylene, cyclohexane, and n-hexane; esters such as ethyl acetate; and ketones, such as acetone, and methyl ethyl ketone. However, the solvent is not particularly limited if it does not interfere with the reaction. Considering the solubility of monomers as starting material and the resulting acrylic acid polymer, and the use of the acrylic acid polymer, it is desirable to use water and/or lower alcohols having 1 to 4 carbons among the above solvents. Among the lower alcohols having 1 to 4 carbons, methyl alcohol, ethyl alcohol, and isopropyl alcohol are particularly effective. The amount of the solvent is not particularly limited.

The polymerization initiator used for polymerization in water is not particularly limited if it is soluble in water. Examples are: peroxides, such as persulfate and hydrogen peroxide of ammonium or alkaline metal; and azoamidine compounds, such as azobis-2-methyl propion amidine hydrochloride. It is possible to use a promotor such as sodium hydrogen sulfite in addition to such polymerization initiators.

Examples of the polymerization initiator used for polymerization in the presence of an organic solvent, for example, lower alcohols, aromatic carbon hydrides, aliphatic carbon hydrides and ketones are: peroxides, such as benzoyl peroxide, lauroyl peroxide; hydroperoxides, such as cumene hydroperoxide; azo-compounds, such as azobisisobutyronitrile. It is possible to use promotors such as amine compounds together with the above polymerization initiators.

Moreover, when using a water and lower-alcohol mixed solvent, a desired solvent and promotor are selected from the polymerization initiators, and combinations of the polymerization initiators and the promoters.

The reaction temperature during solution polymerization is not particularly limited, and is preferably set, for example, within a range of from 0° C. to 120° C. depending on the kinds of the solvent and polymerization initiator used. The reaction time is decided according to the reaction temperature, the kinds and combinations of monomers, or the kind of the polymerization initiator so as to complete the polymerization reaction.

Examples of the polymerization initiator used for bulk polymerization are: peroxides, such as benzoyl peroxide, lauroyl peroxide; hydroperoxides, such as cumene hydroperoxide; azo-compounds, such as azobisisobutyronitrile.

The reaction temperature during bulk polymerization is not particularly limited, and is preferably set, for example, within a range of from 50° C. to 200° C. The reaction time is decided according to the reaction temperature, the kinds, combinations and amounts of monomers, or the composition of the monomeric composition and the kind of the polymerization initiator so as to complete the polymerization reaction.

When preparing an acrylic acid polymer having a structural unit represented by general formula (22)

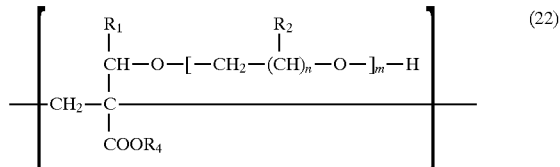

(wherein $R_1$ and $R_2$ independently represent a hydrogen atom or an organic residue, $R_4$ represents a hydrogen atom or counter-ions, n is a positive number among 1 to 3, and m is a positive number among 1 to 100) as the above acrylic acid polymer, for example, an acrylic acid polymer having a structural unit represented by general formula (23)

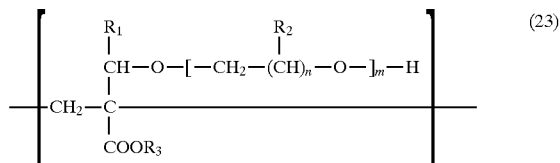

(wherein $R_1$ and $R_2$ independently represent a hydrogen atom or an organic residue, $R_3$ represents an organic residue, n is a positive number among 1 to 3, and m is a positive number among 1 to 100) is prepared by copolymerizing the acrylic ester compound alone or copolymerizing the acrylic ester compound and copolymerizable monomer, and then carboxylic ester of the acrylic acid polymer of general formula (23) is further hydrolyzed with an alkaline substance.

The alkaline substance used for hydrolyzing is not particularly limited. Preferable examples are inorganic salts, such as hydroxides, chlorides and carbonates of monovalent metal and bivalent metal; ammonia; and organic amines.

The degree of polymerization of the resulting acrylic acid polymers is indicated by a number-average molecular weight, and is preferably within a range of from 1,000 to 1,000,000. It is also desirable to perform the polymerization reaction under an atmosphere of inactive gas such as nitrogen gas.

As described above, the novel acrylic ester compound represented by general formula (2) of the present invention is easily prepared by reacting the acrylic ester of general formula (3) with the cyclic ether compound represented by general formula (4). Moreover, the novel acrylic acid compound represented by general formula (1) of the present invention is easily obtained by hydrolyzing the acrylic ester compound of general formula (2). Furthermore, the novel acrylic acid polymer of the present invention has the structural unit represented by general formula (5), and the number-average molecular weight of the acrylic acid polymers is within a range of from 1,000 to 1,000,000.

The novel acrylic acid compound, acrylic ester compound, and acrylic acid polymer of the present invention are fit for the same uses as those of monomers containing known hydroxyl group, for example, hydroxyalkyl(meth)acrylate. For instance, the above acrylic acid compounds, acrylic ester compounds and acrylic acid polymers can be used as so-called paint adhesion improvement agents. More specifically, by adding the above acrylic acid compound, acrylic ester compound or acrylic acid polymer to paint, the adhesion of a coating film to a material to be coated is improved. Furthermore, the above acrylic acid compounds, acrylic ester compounds and acrylic acid polymers are suitably used as crosslinking monomers for crosslinking reaction of a urethane resin and a melamine resin, paint, adhesive agents, surface active agents, washing agent builder, plasticizer, solid electrolyte, antistatic monomers, anti-fogging agents, flocculating agents, dye-affinity modifier, textile modifier, textile treatment agents, dimensional stability imparting agents for wood, scarring preventing agents, hydrophilic monomers, dispersing agents, inorganic fine particle dispersing agent, drilling-mud additives, and concrete admixture.

The physical properties of the acrylic acid compounds, acrylic ester compounds and acrylic acid polymers may be varied to some extent by changing the combinations of the substituents represented by $R_1$, $R_2$, $R_3$, $R_4$ and $R_5$, and the values of n and m.

When using such an acrylic acid polymer for a cement dispersing agent, it is suitable to use the acrylic acid polymer represented by general formula (7)

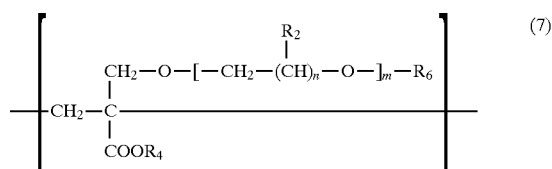

(wherein $R_2$ and $R_6$ independently represent a hydrogen atom or an organic residue, $R_4$ represents a hydrogen atom or counter-ions, n is a positive number among 1 to 3, and m is a positive number among 1 to 100 representing the average number of added moles of oxyalkylene group). The following description will discuss a cement dispersing agent formed by the acrylic acid polymer of general formula (7), and a cement composition containing such a cement dispersing agent.

A cement dispersing agent of the present invention contains an acrylic acid polymer having a structural unit represented by general formula (7). The acrylic acid polymer has a structural unit in which substituents represented by $R_2$ and $R_6$ are independently formed by a hydrogen atom or an organic residue, a substituent represented by $R_4$ is a hydrogen atom or counter-ions, n is a positive number among 1 to 3, and m is a positive number among 1 to 100. The preferred polymers as the acrylic acid polymer are those wherein $R_2$ is a hydrogen atom or an alkyl group having 1 to 8 carbons, $R_6$ is a hydrogen atom, or an alkyl group or phenyl group having 1 to 8 carbons, and $R_4$ is a hydrogen atom, monovalent metal, bivalent metal, an ammonium group or an organic amine group.

The acrylic acid polymers having the structural unit of general formula (7) are easily prepared by, for example, polymerizing a monomeric composition (III) containing at least the acrylic acid derivative of general formula (8)

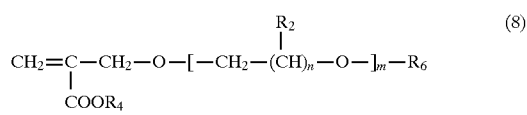

(wherein $R_2$ and $R_6$ independently represent a hydrogen atom or an organic residue, $R_4$ represents a hydrogen atom or counter-ions, n is a positive number among 1 to 3, and m is a positive number among 1 to 100 representing the average number of added moles of oxyalkylene group (hereinafter referred to as the oxyacrylic acid monomers for the sake of explanation)). The monomeric composition (III) may contain the (meth)acrylic acid monomer represented by general formula (10)

(wherein $R_7$ represents a hydrogen atom, methyl group or —$CH_2OH$ group, and $R_8$ represents a hydrogen atom or counter-ions), and may further contain monomer other than the above oxyacrylic acid monomer and the (meth)acrylic acid monomer.

The oxyacrylic acid monomer represented by general formula (8) is a compound in which substituents represented by $R_2$ and $R_6$ are independently formed by a hydrogen atom or an organic residue, a substituent represented by $R_4$ is a hydrogen atom or counter-ions, n is a positive number among 1 to 3, and m is a positive number among 1 to 100 representing the average number of added moles of oxyalkylene group. The preferred compounds as the oxyacrylic acid monomer are those wherein $R_2$ is a hydrogen atom or an alkyl group having 1 to 8 carbons, $R_6$ is a hydrogen atom, or an alkyl group or phenyl group having 1 to 8 carbons, and $R_4$ is a hydrogen atom, monovalent metal, bivalent metal, an ammonium group or an organic amine group.

Such an oxyacrylic acid monomer is easily obtained by the following methods. For example, (i) hydrolyzing carboxylic ester after addition of alkylene oxide to α-(hydroxymethyl) acrylic ester (see the method for preparing acrylic acid compound mentioned above), (ii) hydrolyzing carboxylic acid after reacting α-(hydroxymethyl) acrylic ester with polyalkylene glycol monoalkyl ether, and (iii)

hydrolyzing carboxylic acid after reacting α-(halomethyl) acrylic ester with polyalkylene glycol monoalkyl ether. It is possible to use only one kind of alkylene oxide as starting material in the above reaction, or mix more than one kind of alkylene oxides. Therefore, in the oxyacrylic acid polymer of general formula (7) and the oxyacrylic acid monomer of general formula (8), a portion derived from alkylene oxide, i.e., a repeated structure of oxyalkylene group represented by —CH$_2$(CHR$_2$)$_n$—O, has the following structure. More specifically, the substituent represented by R$_2$ may be independently formed by a hydrogen atom or an organic residue in each oxyalkylene group, and these oxyalkylene groups may be bonded in a block or at random.

Examples of the oxyacrylic acid monomer are:

α-(hydroxypolyalkylene oxymethyl) acrylic acids, such as α-(hydroxypolyethylene oxymethyl) acrylic acid, α-(hydroxypolypropylene oxymethyl) acrylic acid, and α-(hydroxypolybutylene oxymethyl) acrylic acid;

α-(alkoxypolyethylene oxymethyl) acrylic acids, such as α-(methoxypolyethylene oxymethyl) acrylic acid, α-(ethoxypolyethylene oxymethyl) acrylic acid, α-(phenoxypolyethylene oxymethyl) acrylic acid;

α-(alkoxypolypropylene oxymethyl) acrylic acids, such as α-(methoxypolypropylene oxymethyl) acrylic acid, α-(ethoxypolypropylene oxymethyl) acrylic acid, and α-(phenoxypolypropylene oxymethyl) acrylic acid;

α-(alkoxypolybutylene oxymethyl) acrylic acids, such as α-(methoxypolybutylene oxymethyl) acrylic acid, α-(ethoxypolybutylene oxymethyl) acrylic acid, and α-(phenoxypolybutylene oxymethyl) acrylic acid;

α-(hydroxypolyalkylene oxymethyl) acrylic acids, such as α-(hydroxypolyethylene oxypolypropylene oxymethyl) acrylic acid, α-(hydroxypolyethylene oxypolybutylene oxymethyl) acrylic acid, α-(hydroxypolypropylene oxypolybutylene oxymethyl) acrylic acid, α-(hydroxypolyethylene oxypolypropylene oxypolybutylene oxymethyl) acrylic acids;

α-(alkoxypolyalkylene oxymethyl) acrylic acids, such as α-(methoxypolyethylene oxypolypropylene oxymethyl) acrylic acid, α-(methoxypolyethylene oxypolybutylene oxymethyl) acrylic acid, α-(methoxypolypropylene oxypolybutylene oxymethyl) acrylic acid, α-(methoxypolyethylene oxypolypropylene oxypolybutylene oxymethyl) acrylic acid, α-(ethoxypolyethylene oxypolypropylene oxymethyl) acrylic acid, α-(ethoxypolyethylene oxypolybutylene oxymethyl) acrylic acid, α-(ethoxypolypropylene oxypolybutylene oxymethyl) acrylic acid, α-(ethoxypolyethylene oxypolypropylene oxypolybutylene oxymethyl) acrylic acid, α-(phenoxypolyethylene oxypolypropylene oxymethyl) acrylic acid, α-(phenoxypolyethylene oxypolybutylene oxymethyl) acrylic acid, α-(phenoxypolypropylene oxypolybutylene oxymethyl) acrylic acid, α-(phenoxypolyethylene oxypolypropylene oxypolybutylene oxymethyl) acrylic acid; and monovalent metallic salts such as sodium salt and potassium salt, bivalent metallic salts such as magnesium salt and zinc salt, ammonium salt, and organic amine salts such as trimethylamine salt and triethylamine salt of the above-listed compounds.

It is possible to use only one kind of the oxyacrylic acid monomers, or suitable combinations of more than one kind of the oxyacrylic acid monomers. The average number of added moles of oxyalkylene group is within a range of from 1 to 100, and such oxyacrylic acid monomers exhibit strong cement dispersing effects by hydrophilic nature and stereospecific repulsion of polyalkylene group. Thus, among the oxyacrylic acid monomers, it is more desirable to use α-(hydroxypolyalkylene oxymethyl) acrylic acids, α-(methoxypolyethylene oxymethyl) acrylic acids, and their monovalent metallic salts wherein the average number of added moles of oxyalkylene group is within a range of from 1 to 100, more preferably within a range of from 5 to 100.

The (meth)acrylic acid monomer represented by general formula (10) is not particularly limited, but is a compound wherein the substituent represented by R$_7$ is a hydrogen atom, methyl group or —CH$_2$OH group, and the substituent represented by R$_8$ is a hydrogen atom or counter-ions. Counter-ions represented by R$_8$ are, for example, monovalent metal, bivalent metal, ammonium group and organic amine group.

The (meth)acrylic acid monomer represented by general formula (10) which is used for the monomeric composition (III), if necessary, is not particularly limited. The same compounds as those exemplified as (meth)acrylic acid monomers of general formula (17) can be used. It is possible to use only one kind of (meth)acrylic acid monomer of general formula (10) or combinations of more than one kind of (meth)acrylic acid monomers of general formula (10). Among the (meth)acrylic acid monomers of general formula (10), acrylic acids, methacrylic acids and their sodium salts are preferred because they show excellent reactivity and polymerizable properties with the oxyacrylic acid monomer.

Furthermore, other monomers copolymerizable with the oxyacrylic acid monomer and the (meth)acrylic acid monomer of general formula (10), i.e., other monomers contained in the monomeric composition (III), if necessary (hereinafter just referred to as other monomers), are compounds which do not deteriorate required various physical properties of the acrylic acid polymer (D) (hereinafter referred to as polymer (D) formed by copolymerization of the monomeric composition (III)).

The above-mentioned other monomers are not particularly limited, and the same compounds as those exemplified in the preparation of the acrylic acid polymer having the structural unit of general formula (5) may be used. It is possible to use only one kind of the other monomer or combinations of more than one kind of the other monomers.

The amount of monomer in the monomeric composition (III) is not particularly limited. However, the amount of oxyacrylic acid monomer is preferably within a range of from 1 weight percent to 100 weight percent, and more preferably within a range of from 20 weight percent to 100 weight percent. It is possible to prepare a cement dispersing agent which has superior water reducing ability and slump maintaining ability and is capable of lowering air entrainment with small loadings by arranging the monomeric composition (III) to contain the above oxyacrylic acid monomer.

The (meth)acrylic acid monomer of general formula (10) and the other monomer are used, if necessary, so that the (meth)acrylic acid monomer is within a range of from 99 weight percent to 0 weight percent and the other monomer is within a range of from 1 weight percent to 50 weight percent (the total amount of the oxyacrylic acid monomer, the (meth)acrylic acid monomer of general formula (10), and the other monomer is 100 weight percent). If the respective monomers fall outside of the above ranges, the target cement dispersing agent with superior properties cannot be obtained.

The combinations of the monomers in the monomeric composition (III) are not particularly limited if at least the oxyacrylic acid monomer is contained. Namely, structural units other than the structural unit of general formula (7) in the polymer (D) formed by polymerization of the monomeric composition (III) are not particularly limited. The monomers in the monomeric composition (III) can be freely combined if the content falls within the above mentioned range. However, it is desirable to combine 20 weight percent to 100 weight percent of the oxyacrylic acid monomer and 80 weight percent to 0 weight percent of the (meth)acrylic acid monomer of general formula (10).

It is also possible to prepare the acrylic acid polymer having the structural unit represented by general formula (7) by polymerizing the monomeric composition (IV) containing at least the acrylic acid derivative represented by general formula (9)

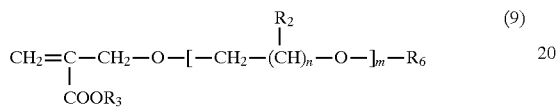

(wherein $R_2$ and $R_6$ independently represent a hydrogen atom or an organic residue, $R_3$ represents an organic residue, n is a positive number among 1 to 3, and m is a positive number among 1 to 100 representing the average number of added moles of oxyalkylene group (hereinafter referred to as the oxyacrylate monomers for the sake of explanation)), and by hydrolyzing the resulting acrylic acid polymer (F) (hereinafter just referred to as the polymer (F)) with an alkaline substance. Moreover, the monomeric composition (IV) may contain, if necessary, the (meth)acrylic acid monomer of general formula (10) and/or the (meth)acrylic acid monomer represented by general formula (11)

(wherein $R_9$ represents a hydrogen atom, methyl group or —$CH_2OH$ group, and $R_{10}$ represents an organic residue), and may further contain monomer other than the above monomers (the oxyacrylate monomers and the (meth)acrylic acid monomers of generals formulas (10) and (11)).

The oxyacrylate monomer represented by general formula (9) is a compound in which substituents represented by $R_2$ and $R_6$ are independently formed by a hydrogen atom or an organic residue, a substituent represented by $R_3$ is an organic residue, n is a positive number among 1 to 3, and m is a positive number among 1 to 100 representing the average number of added moles of oxyalkylene group. The preferred compounds as the oxyacrylate monomer are those wherein $R_2$ is a hydrogen atom or an alkyl group having 1 to 8 carbons, $R_6$ is a hydrogen atom, or an alkyl group or phenyl group having 1 to 8 carbons, and $R_3$ is an alkyl group having 1 to 8 carbons.

Such an oxyacrylate monomer is easily obtained by the following methods. For example, (iv) adding alkylene oxide to α-(hydroxymethyl) acrylic ester (see the method for preparing acrylic ester compound mentioned above), (v) reacting α-(hydroxymethyl) acrylic ester with polyalkylene glycol monoalkyl ether, and (vi) reacting α-(halomethyl) acrylic ester with polyalkylene glycol monoalkyl ether. It is possible to use only one kind of alkylene oxide as starting material or suitably mix more than one kind of alkylene oxides for the reaction. Therefore, in the oxyacrylate monomer of general formula (9), a portion derived from alkylene oxide, i.e., a repeated structure of oxyalkylene group represented by —$CH_2(CHR_2)_n$—O, has the following structure. More specifically, the substituent represented by $R_2$ may be independently formed by a hydrogen atom or an organic residue in each oxyalkylene group, and these oxyalkylene groups may be bonded in a block or at random. A method for preparing the oxyacrylate monomer will be described later in detail.

Examples of the oxyacrylate monomers are:

α-(hydroxy polyalkylene oxymethyl) acrylic esters, such as methyl-α-(hydroxypolyethylene oxymethyl) acrylate, ethyl-α-(hydroxypolyethylene oxymethyl) acrylate, butyl-α-(hydroxypolyethylene oxymethyl) acrylate, octyl-α-(hydroxypolyethylene oxymethyl) acrylate, methyl-α-(hydroxypolypropylene oxymethyl) acrylate, ethyl-α-(hydroxypolypropylene oxymethyl) acrylate, butyl-α-(hydroxypolypropylene oxymethyl) acrylate, octyl-α-(hydroxypolypropylene oxymethyl) acrylate, methyl-α-(hydroxypolybutylene oxymethyl) acrylate, ethyl-α-(hydroxypolybutylene oxymethyl) acrylate, butyl-α-(hydroxypolybutylene oxymethyl) acrylate, and octyl-α-(hydroxypolybutylene oxymethyl) acrylate;

α-(alkoxypolyethylene oxymethyl) acrylic esters, such as methyl-α-(methoxypolyethylene oxymethyl) acrylate, ethyl-α-(methoxypolyethylene oxymethyl) acrylate, butyl-α-(methoxypolyethylene oxymethyl) acrylate, octyl-α-(methoxypolyethylene oxymethyl) acrylate, methyl-α-(ethoxypolyethylene oxymethyl) acrylate, ethyl-α-(ethoxypolyethylene oxymethyl) acrylate, butyl-α-(ethoxypolyethylene oxymethyl) acrylate, octyl-α-(ethoxypolyethylene oxymethyl) acrylate, methyl-α-(phenoxypolyethylene oxymethyl) acrylate, ethyl-α-(phenoxypolyethylene oxymethyl) acrylate, butyl-α-(phenoxypolyethylene oxymethyl) acrylate, and octyl-α-(phenoxypolyethylene oxymethyl) acrylate;

α-(alkoxypolypropylene oxymethyl) acrylic esters, such as methyl-α-(methoxypolypropylene oxymethyl) acrylate, ethyl-α-(methoxypolypropylene oxymethyl) acrylate, butyl-α-(methoxypolypropylene oxymethyl) acrylate, octyl-α-(methoxypolypropylene oxymethyl) acrylate, methyl-α-(ethoxypolypropylene oxymethyl) acrylate, ethyl-α-(ethoxypolypropylene oxymethyl) acrylate, butyl-α-(ethoxypolypropylene oxymethyl) acrylate, octyl-α-(ethoxypolypropylene oxymethyl) acrylate, methyl-α-(phenoxypolypropylene oxymethyl) acrylate, ethyl-α-(phenoxypolypropylene oxymethyl) acrylate, butyl-α-(phenoxypolypropylene oxymethyl) acrylate, and octyl-α-(phenoxypolypropylene oxymethyl) acrylate;

α-(alkoxypolybutylene oxymethyl) acrylic esters, such as methyl-α-(methoxypolybutylene oxymethyl) acrylate, ethyl-α-(methoxypolybutylene oxymethyl) acrylate, butyl-α-(methoxypolybutylene oxymethyl) acrylate, octyl-α-(methoxypolybutylene oxymethyl) acrylate, methyl-α-(ethoxypolybutylene oxymethyl) acrylate, ethyl-α-(ethoxypolybutylene oxymethyl) acrylate, butyl-α-(ethoxypolybutylene oxymethyl) acrylate, octyl-α-(ethoxypolybutylene oxymethyl) acrylate, methyl-α-(phenoxypolybutylene oxymethyl) acrylate, ethyl-α-(phenoxypolybutylene oxymethyl) acrylate, butyl-α-(phenoxypolybutylene oxymethyl) acrylate, octyl-α-(phenoxypolybutylene oxymethyl) acrylate;

α-(hydroxypolyalkylene oxymethyl) acrylic esters, such as methyl-α-(hydroxypolyethylene oxypolypropylene oxymethyl) acrylate, ethyl-α-(hydroxypolyethylene oxypolypropylene oxymethyl) acrylate, butyl-α-

(hydroxypolyethylene oxypolypropylene oxymethyl) acrylate, octyl-α-(hydroxypolyethylene oxypolypropylene oxymethyl) acrylate, methyl-α-(hydroxypolyethylene oxypolybutylene oxymethyl) acrylate, ethyl-α-(hydroxypolyethylene oxypolybutylene oxymethyl) acrylate, butyl-α-(hydroxypolyethylene oxypolybutylene oxymethyl) acrylate, octyl-α-(hydroxypolyethylene oxypolybutylene oxymethyl) acrylate:

methyl-α-(hydroxypolypropylene oxypolybutylene oxymethyl) acrylate, ethyl-α-(hydroxypolypropylene oxypolybutylene oxymethyl) acrylate, butyl-α-(hydroxypolypropylene oxypolybutylene oxymethyl) acrylate, octyl-α-(hydroxypolypropylene oxypolybutylene oxymethyl) acrylate, methyl-α-(hydroxypolyethylene oxypolypropylene oxypolybutylene oxymethyl) acrylate, ethyl-α-(hydroxypolyethylene oxypolypropylene oxypolybutylene oxymethyl) acrylate, butyl-α-(hydroxypolyethylene oxypolypropylene oxypolybutylene oxymethyl) acrylate, octyl-α-(hydroxypolyethylene oxypolypropylene oxypolybutylene oxymethyl) acrylate; and α-(alkoxypolyalkylene oxymethyl) acrylic esters, such as methyl-α-(methoxypolyethylene oxypolypropylene oxymethyl) acrylate, ethyl-α-(methoxypolyethylene oxypolypropylene oxymethyl) acrylate, butyl-α-(methoxypolyethylene oxypolypropylene oxymethyl) acrylate, octyl-α-(methoxypolyethylene oxypolypropylene oxymethyl) acrylate, methyl-α-(methoxypolyethylene oxypolybutylene oxymethyl) acrylate, ethyl-α-(methoxypolyethylene oxypolybutylene oxymethyl) acrylate, butyl-α-(methoxypolyethylene oxypolybutylene oxymethyl) acrylate, octyl-α-(methoxypolyethylene oxypolybutylene oxymethyl) acrylate, methyl-α-(methoxypolypropylene oxypolybutylene oxymethyl) acrylate, ethyl-α-(methoxypolypropylene oxypolybutylene oxymethyl) acrylate, butyl-α-(methoxypolypropylene oxypolybutylene oxymethyl) acrylate, octyl-α-(methoxypolypropylene oxypolybutylene oxymethyl) acrylate, methyl-α-(methoxypolyethylene oxypolypropylene oxypolybutylene oxymethyl) acrylate, ethyl-α-(methoxypolyethylene oxypolypropylene oxypolybutylene oxymethyl) acrylate, butyl-α-(methoxypolyethylene oxypolypropylene oxypolybutylene oxymethyl) acrylate, octyl-α-(methoxypolyethylene oxypolypropylene oxypolybutylene oxymethyl) acrylate, methyl-α-(ethoxypolyethylene oxypolypropylene oxymethyl) acrylate, ethyl-α-(ethoxypolyethylene oxypolypropylene oxymethyl) acrylate, butyl-α-(ethoxypolyethylene oxypolypropylene oxymethyl) acrylate, octyl-α-(ethoxypolyethylene oxypolypropylene oxymethyl) acrylate, methyl-α-(ethoxypolyethylene oxypolybutylene oxymethyl) acrylate, ethyl-α-(ethoxypolyethylene oxypolybutylene oxymethyl) acrylate, butyl-α-(ethoxypolyethylene oxypolybutylene oxymethyl) acrylate, octyl-α-(ethoxypolyethylene oxypolybutylene oxymethyl) acrylate, methyl-α-(ethoxypolypropylene oxypolybutylene oxymethyl) acrylate, ethyl-α-(ethoxypolypropylene oxypolybutylene oxymethyl) acrylate, butyl-α-(ethoxypolypropylene oxypolybutylene oxymethyl) acrylate, octyl-α-(ethoxypolypropylene oxypolybutylene oxymethyl) acrylate, methyl-α-(ethoxypolyethylene oxypolypropylene oxypolybutylene oxymethyl) acrylate, ethyl-α-(ethoxypolyethylene oxypolypropylene oxypolybutylene oxymethyl) acrylate, butyl-α-(ethoxypolyethylene oxypolypropylene oxypolybutylene oxymethyl) acrylate, octyl-α-(ethoxypolyethylene oxypolypropylene oxypolybutylene oxymethyl) acrylate, methyl-α-(phenoxypolyethylene oxypolypropylene oxymethyl) acrylate, ethyl-α-(phenoxypolyethylene oxypolypropylene oxymethyl) acrylate, butyl-α-(phenoxypolyethylene oxypolypropylene oxymethyl) acrylate, octyl-α-(phenoxypolyethylene oxypolypropylene oxymethyl) acrylate, methyl-α-(phenoxypolyethylene oxypolybutylene oxymethyl) acrylate, ethyl-α-(phenoxypolyethylene oxypolybutylene oxymethyl) acrylate, butyl-α-(phenoxypolyethylene oxypolybutylene oxymethyl) acrylate, octyl-α-(phenoxypolyethylene oxypolybutylene oxymethyl) acrylate, methyl-α-(phenoxypolypropylene oxypolybutylene oxymethyl) acrylate, ethyl-α-(phenoxypolypropylene oxypolybutylene oxymethyl) acrylate, butyl-α-(phenoxypolypropylene oxypolybutylene oxymethyl) acrylate, octyl-α-(phenoxypolypropylene oxypolybutylene oxymethyl) acrylate, methyl-α-(phenoxypolyethylene oxypolypropylene oxypolybutylene oxymethyl) acrylate, ethyl-α-(phenoxypolyethylene oxypolypropylene oxypolybutylene oxymethyl) acrylate, butyl-α-(phenoxypolyethylene oxypolypropylene oxypolybutylene oxymethyl) acrylate, and octyl-α-(phenoxypolyethylene oxypolypropylene oxypolybutylene oxymethyl) acrylate.

It is possible to use only one kind of the oxyacrylate monomer, or suitable combinations of more than one kind of the oxyacrylate monomers. The average number of added moles of oxyalkylene group in such an oxyacrylate monomer is within a range of from 1 to 100, and these oxyacrylate monomers exhibit strong cement dispersing effects by hydrophilic nature and stereospecific repulsion of polyalkylene group. Thus, among the oxyacrylate monomers, it is more desirable to use alkyl-α-(hydroxypolyethylene oxymethyl) acrylic esters and alkyl-α-(methoxypolyethylene oxymethyl) acrylic esters wherein the average number of added moles of oxyalkylene group is within a range of from 5 to 100.

The (meta)acrylic acid monomer represented by general formula (11) is not particularly limited, but is a compound wherein the substituent represented by $R_9$ is a hydrogen atom, methyl group or —$CH_2OH$ group, and the substituent represented by $R_{10}$ is an organic residue. More specifically, the substituent represented by $R_{10}$ is, for example, an alkyl group having 1 to 8 carbons.

The (meth)acrylic acid monomer of general formula (11) which is used for the monomeric composition (IV), if necessary, is not particularly limited. The same compounds as those exemplified as (meth)acrylic acid monomer of general formula (18). It is possible to use only one kind of (meth)acrylic acid monomer of general formula (11) or combinations of more than one kind of (meth)acrylate monomers of general formula (11). The preferred (meth) acrylic acid monomers of general formula (11) are methyl acrylate, ethyl acrylate, n-butyl acrylate, 2-ethylhexyl acrylate, methyl methacrylate, ethyl methacrylate, n-butyl methacrylate, and 2-ethylhexyl methacrylate because they show excellent reactivity and polymerizable properties with the oxyacrylate monomers.

Moreover, as the (meth)acrylic acid monomer of general formula (10) which is used for the monomeric composition (IV), the same compounds as those exemplified as the above-mentioned (meth)acrylic acid monomers. The compounds which are exemplified as the preferred compounds in the method for preparing the monomeric composition (III) can also be used as preferred compounds of such a (meth) acrylic acid monomer.

Furthermore, other monomers copolymerizable with the above monomers (the oxyacrylate monomers, the (meth) acrylic acid monomers of general formulas (10) and (11)), i.e., other monomers contained in the monomeric composition (IV), if necessary (hereinafter just referred to as other monomers), are compounds which do not deteriorate required various physical properties of the acrylic acid polymer (G) (hereinafter referred to as polymer (G)) obtained by hydrolyzing the polymer (F) formed by the polymerization of the monomeric composition (IV) with an alkaline substance. The above-mentioned other monomers are not particularly limited, and the same compounds as those exemplified in the preparation of the acrylic acid polymers having the structural unit represented by general formula (5) can be used. It is possible to use only one kind of the other monomer or combinations of more than one kind of the other monomers.

The amount of monomers contained in the monomeric composition (IV) is not particularly limited. However, the amount of oxyacrylate monomer is preferably within a range of from 1 weight percent to 100 weight percent, and more preferably within a range of from 20 weight percent to 100 weight percent. It is possible to prepare cement dispersing agents which have superior water reducing ability and slump maintaining ability and are capable of lowering air entrainment with small loadings by arranging the monomeric composition (IV) to contain the above oxyacrylate monomer.

The (meth)acrylic acid monomers of general formulas (10) and (11) and the other monomer are used, if necessary, so that (meth)acrylic acid monomer of general formula (10) is within a range of from 99 weight percent to 0 weight percent, the (meth)acrylic acid monomer of general formula (11) is within a range of from 99 weight percent to 0 weight percent and the other monomer is within a range of from 0 weight percent to 50 weight percent (the total amount of the oxyacrylate monomer, the (meth)acrylic acid monomers of general formulas (10) and (11) and the other monomer is 100 weight percent). If the respective monomers fall outside of the above ranges, a target cement dispersing agent with superior properties cannot be obtained.

The combinations of the monomers in the monomeric composition (IV) are not particularly limited if at least the oxyacrylate monomer is contained. Namely, structural units other than the structural unit of general formula (7) in the polymer (G) obtained by hydrolyzing the polymer (F) formed by the polymerization of the monomeric composition (IV) with the alkaline substance are not particularly limited. The monomers in the monomeric composition (IV) can be freely combined if the content falls within the above mentioned range. However, it is desirable to combine 20 weight percent to 100 weight percent of the oxyacrylate monomer and 80 weight percent to 0 weight percent of the (meth)acrylic acid monomer.

A method for preparing the polymer (D) or the polymer (F) is not particularly limited, and it is possible to use the same methods as those explained in the preparation of the acrylic acid polymers having the structural unit represented by general formula (5). Namely, it is possible to use various known methods for polymerization, for example, a method using a polymerization initiator such as a radical polymerization initiator, a method using radiation such as ionized radiation, electron rays, and irradiation of ultraviolet rays, and a method using heat. For instance, the desired polymers (D) and (F) can be easily prepared by solution polymerization in which polymerization is performed in a solvent under the presence of the polymerization initiator, or bulk polymerization which is performed without a solvent.

The solution polymerization can be performed batch-wise or continuously. Examples of the solvent used for the solution polymerization are: water; alcohols, such as methyl alcohol, ethyl alcohol, and isopropyl alcohol; hydrocarbons, such as benzene, toluene, xylene, cyclohexane, and n-hexane; esters such as ethyl acetate; and ketones, such as acetone, and methyl ethyl ketone. However, the solvent is not particularly limited if it does not interfere with the reaction. Considering the solubility of monomer as starting material and the resulting polymers (D) and (F) and the uses of the polymers (D) and (F), it is desirable to use water and/or lower alcohols having 1 to 4 carbons among the above solvents. Among the lower alcohols having 1 to 4 carbons, methyl alcohol, ethyl alcohol, and isopropyl alcohol are particularly effective. The amount of the solvent is not particularly limited.

The polymerization initiator used for polymerization in the presence of water is not particularly limited if it is soluble in water. Examples are: peroxides, such as persulfate and hydrogen peroxide of ammonium or alkaline metal; and azoamidine compounds, such as azobis-2-methyl propion amidine hydrochloride. It is possible to use a promotor such as sodium hydrogen sulfite in addition to these polymerization initiators.

Examples of the polymerization initiator used for polymerization in the presence of an organic solvent, for example, lower alcohols, aromatic carbon hydrides, aliphatic carbon hydrides, esters and ketones, are: peroxides, such as benzoyl peroxide, and lauroyl peroxide; hydroperoxides, such as cumene hydroperoxide; and azo-compounds, such as azobisisobutyronitrile. It is possible to use a promotor such as an amine compound together with the polymerization initiators.

Moreover, when using a water and lower-alcohol mixed solvent, a desired polymerization initiator and a desired promotor are selected from the polymerization initiators, and combinations of the polymerization initiators and the promoters.

The reaction temperature during solution polymerization is not particularly limited, and is preferably set, for example, within a range of from 0° C. to 120° C. depending on the composition of the monomeric composition (III) or (IV) used, and the kinds of the solvent and polymerization initiator used. The reaction time is decided according to the reaction temperature, the composition of the monomeric composition (III) or (IV) used, and the kind of the polymerization initiator used so as to complete the polymerization reaction.

Examples of the polymerization initiator used for bulk polymerization are: peroxides, such as benzoyl peroxide, lauroyl peroxide; hydroperoxides, such as cumene hydroperoxide; and azo-compounds, such as azobisisobutyronitrile.

The reaction temperature during bulk polymerization is not particularly limited, and is preferably set, for example, within a range of from 50° C. to 200° C. The reaction time is decided according to the reaction temperature, the composition of the monomeric composition (III) or (IV) used, and the kind of the polymerization initiator so as to complete the polymerization reaction.

Suitable examples of the alkaline substance used for hydrolyzing the carboxylic esters are: inorganic salts, such as hydroxides, chlorides and carbonates of monovalent metal and bivalent metal; ammonia; and organic amines. Thus, by hydrolyzing the carboxylic ester of the polymer (F), the polymer (G) having the structural unit of general formula (7) is easily obtained. The polymer (G) has superior water reducing ability and slump maintaining ability, and is suitably used as a cement dispersing agent.

On the other hand, although the polymer (D) by itself has superior water reducing ability and slump maintaining ability and is suitably used as a cement dispersing agent, the acrylic acid polymer (E)(hereinafter just referred to as the polymer (E)) obtained by neutralizing the polymer (D) with an alkaline substance may be used as a cement dispersing agent, if necessary. The polymer (E) is a polymer obtained by neutralizing the polymer (D), and also has a structural unit represented by general formula (7). Suitable examples of the alkaline substance are: inorganic salts, such as hydroxides, chlorides and carbonates of monovalent metal and bivalent metal; ammonia; and organic amines.

The weight-average molecular weight (Mw) of the polymer (D), polymer (E) and polymer (G) obtained by the above method is preferably within a range of from 1000 to 500,000. If the weight-average molecular weight (Mw) is less than 1000, the water reducing ability and slump loss preventing ability of the resulting cement dispersing agent degrade. On the other hand, if the weight-average molecular weight (Mw) exceeds 500,000, the water reducing ability of the resulting cement dispersing agent degrades.

Thus, the cement dispersing agent of the present invention is characterized by containing the acrylic acid polymer having the structural unit represented by general formula (7). Examples of the polymer of general formula (7) are at least one kind of polymer selected from the group consisting of the polymer (D), the polymer (E) and the polymer (G).

Moreover, the cement dispersing agent of the present invention may be used in combinations of at least one kind of acrylic acid polymer as a main component selected from the group consisting of the polymer (D), the polymer (E) and the polymer (G), and other known cement admixture. Examples of the cement admixture are conventional cement dispersing agents, air-entraining agents, antifoaming agents, cement wetting agents, blowing agents, waterproofing agents, delaying agents, quick-setting agents, water-soluble polymeric substances, thickeners, flocculating agents, drying and shrinking agents, strength promoting agents, and accelerating agents.

The cement composition of the present invention contains at least cement, water, and the above cement dispersing agent. Examples of the cement are hydraulic materials except for dental cement such as plaster including gypsum, and hydraulic cement such as portland cement, high alumina cement and various blended cements.

The cement dispersing agent of the present invention can produce significant effects with lower loadings compared to the conventional cement dispersing agents. The amount of the cement dispersing agent contained in the cement composition varies depending on the kind of the cement dispersing agent used and the kind and loadings of cement. For instance, if mortar or concrete using hydraulic cement is used as the cement composition, the amount of the cement dispersing agent is preferably within a range of from 0.01 weight percent to 1.0 weight percent of the cement, and more preferably within 0.02 weight percent to 0.5 weight percent. Since the cement composition contains the cement dispersing agent of the present invention, i.e., a cement dispersing agent containing an acrylic acid polymer having the structural unit of general formula (7) as a main component, it is possible to produce the following effects: increased slump of the cement composition, reduced quantity of water per unit volume of concrete, increased strength, and improved durability. If the content of the cement dispersing agent, i.e., the loadings of the cement dispersing agent with respect to cement, is lower than 0.01 weight percent, the above-mentioned effects cannot be sufficiently exhibited. Whereas if the loadings of the cement dispersing agent exceed 1.0 weight percent, further improvements of the effects in proportion to the increased loadings cannot be expected. Namely, part of the added cement dispersing agent is wasted, resulting in economical inefficiency.

The time at which the cement dispersing agent is loaded to other materials constituting the cement composition is not particularly limited. For example, it is desirable to load the cement dispersing agent at the time of mixing. The method of mixing is not particularly limited, and, for example, a forced mixing type mixer may be used.

For example, the cement composition may contain fine aggregate and coarse aggregate which are usually used for the preparation of concrete, and other conventional additives used for the conventional cement composition.

As described above, the cement dispersing agent of the present invention contains the acrylic acid polymer having the structural unit of general formula (7). Examples of the acrylic acid polymer are: the polymer (D) formed by polymerization of the monomeric composition (III) containing at least the oxyacrylic acid monomer represented by general formula (8); the polymer (E) formed by hydrolyzing the polymer (D) with an alkaline substance; and the polymer (G) obtained by hydrolyzing with an alkaline substance the polymer (F) formed by the polymerization of the monomeric composition (IV) containing at least the oxyacrylate monomer of general formula (9). Each of the polymers (D), (F) and (G) can be used independently as a cement dispersing agent. It is also possible to mix the polymers (D), (F) and (G), or mix the polymers (D), (F) and (G) with cement admixture other than these polymers for use as cement dispersing agents. Moreover, the cement composition of the present invention contains at least cement, water and the above-mentioned cement dispersing agent.

With this structure, the cement dispersing agent and the cement composition of the present invention have superior water reducing ability and slump maintaining ability compared to the conventional cement dispersing agents and cement compositions, thereby reducing the loadings of the cement dispersing agent with respect to cement. Furthermore, the cement dispersing agent and the cement composition of the present invention achieve lower air entrainment, and are capable of imparting a predetermined strength to the hardened cement composition in a stable manner.

The reasons for the achievement of reduction in loadings and lowering of air entrainment are not assured, but the inventors conjecture as follows. The cement dispersing agent of the present invention is formed by a monomer having a carboxylic group which adheres to cement particles and a polyalkylene glycol group for dispersing the cement particles in a molecule as an essential monomeric component. Therefore, the polymer as main component of the cement dispersing agent of the present invention has a uniform composition without deviation in polymer composition distribution which is derived from the difference in copolymerizable properties between two monomers having a carboxylic group and polyalkylene glycol group, respectively, during copolymerization. Thus, the cement dispersing agent of the present invention has balanced cement particle adhesion ability and cement particle dispersing ability, and can fully utilize the ability, thereby reducing loadings of the cement dispersing agent and lowering of air entrainment. However, the cement dispersing agent of the present invention is not necessarily limited by such reasons.

The following description will discuss in detail a method for preparing the acrylic acid derivative of general formula (8), i.e., oxyacrylate monomer, which is suitable as a starting material of such a cement dispersing agent.

As described above, the oxyacrylate monomer can be easily prepared by, for example, any of the above-mentioned methods: (iv) adding alkylene oxide to α-(hydroxymethyl) acrylic ester; (v) reacting polyalkylene glycol monoalkyl ether with α-(hydroxymethyl) acrylic ester; and (vi) reacting polyalkylene glycol monoalkyl ether with α-(halomethyl) acrylic ether.

Method (iv) is suitable for the preparation of the oxyacrylate monomer of general formula (9), particularly, a compound wherein a substituent represented by $R_6$ is a hydrogen atom. Method (iv) is the same as the method explained in the preparation of the acrylate monomer of general formula (2).

Method (v) or (vi) are suitable for the preparation of oxyacrylate monomer of general formula (9), particularly, a compound wherein a substituent represented by $R_6$ is an organic residue.

Method (vi) is a known method. The method for preparing the oxyacrylate monomer is not particularly limited, and various methods may be used. However, method (vi) uses α-(halomethyl) acrylic ester as starting material. Therefore, if the oxyacrylate monomer is industrially produced by method (vi), it is necessary to use means for preventing corrosion of the manufacturing device, and the process of purifying the resulting reaction product is complicated. Moreover, hydrogen halide is generated as a by-product during preparation, and if the hydrogen halide is discarded, environmental distraction will result.

The following description will discuss a method for preparing a novel acrylic acid derivative irrelevant of the above-mentioned problems, i.e., method (v) for preparing an oxyacrylate monomer represented by general formula (12)

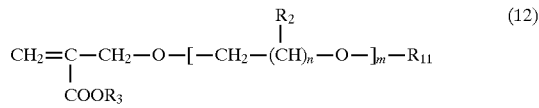

(wherein $R_2$ represents a hydrogen atom or an organic residue, $R_3$ and $R_{11}$ independently represent an organic residue, n is a positive number among 1 to 3, and m is a positive number among 1 to 100 representing the average number of added moles of oxyalkylene group).

The oxyacrylate monomer of general formula (12) of the present invention is easily prepared by reacting an acrylic ester represented by general formula (13)

(wherein $R_3$ represents an organic residue) with a compound containing a hydroxyl group, represented by general formula (14)

(wherein $R_2$ represents a hydrogen atom or an organic residue, $R_{11}$ represents an organic residue, n is a positive number among 1 to 3, and m is a positive number among 1 to 100).

The acrylic ester of general formula (13) used as starting material in the above preparation method is not particularly limited, but is a compound wherein a substituent represented by $R_3$ is an organic residue, i.e., α-(hydroxymethyl)acrylic esters. More specifically, examples of such an organic residue represented by $R_3$ are straight-chain, branched-chain or cyclic alkyl groups having 1 to 18 carbons.

Examples of the acrylic ester of general formula (13) are methyl-α-hydroxymethyl acrylate, ethyl-α-hydroxymethyl acrylate, n-butyl-α-hydroxymethyl acrylate, and 2-ethylhexyl-α-hydroxymethyl acrylate.

It is possible to use only one kind of the acrylic ester or mix more than one kind of the acrylic esters. Among these compounds, methyl-α-hydroxymethyl acrylate, ethyl-α-hydroxymethyl acrylate, and n-butyl-α-hydroxymethyl acrylate are preferred because they show excellent reactivity and polymerization properties with respect to the compound having hydroxyl group of general formula (14) and are easy to obtain.

The acrylic ester can be easily obtained by a conventional known method, for example, by reacting corresponding acrylate compound and aldehyde compound under the presence of a catalyst such as a basic ion exchange resin (Japanese Publication for Unexamined Patent Application (Tokukaihei) 6-135896/1994).

The compound containing hydroxyl group of general formula (14) used as starting material in the method for preparing oxyacrylate monomers of the present invention is not particularly limited. Examples are polyalkylene glycol monoalkyl ethers, such as methyl-cellosolve, ethyl-cellosolve, butyl-cellosolve, Carbitol, polyethylene glycol monomethoxy ether, and polypropylene glycol monoethoxy ether. It is possible to use only one kind of compound containing hydroxyl group or mix more than one kind of compounds containing hydroxyl group.

Although the amount of a compound containing hydroxyl group to be added to acrylic ester varies depending on the kind of the compound containing hydroxyl group used, it is preferably set, for example, within a range of from 0.1 mole to 10 mole with respect to one mole of the acrylic ester.

The catalyst used in the method for preparing oxyacrylate monomer of the present invention is an acid, and more preferably protonic acid.

The catalyst is not particularly limited. Examples of such a catalyst are protonic acids including mineral acids, such as hydrochloric acid, sulfuric acid, phosphoric acid and boric acid, partially neutralized salts of the mineral acids; heteropoly acids, such as tungstophosphoric acid, molybdophosphoric acid, tungstosilicic acid and phosphomolybdic acid, and partially neutralized salts of the heteropoly acids; and organic sulfonic acids, such as methane sulfonic acid and paratoluene sulfonic acid; and acid ion exchange resin. It is possible to use only one kind of catalyst or mix more than one kind of catalyst.

The amount of the catalyst to be added to acrylic ester varies depending on the kind of acrylic ester used. For example, the proportion of the catalyst to the acrylic ester is preferably within a range of from 0.001 mole percent to 50 mole percent, and more preferably within a range of from 0.01 mole percent to 20 mole percent. When the amount of the catalyst is less than 0.001 mole percent, it is hard to exhibit the catalyst activity to the full. As a result, the reaction time becomes too long, and the oxyacrylate monomer cannot be produced efficiently. On the other hand, if the amount of the catalyst exceeds 50 mole percent, a further improvement of the catalytic effect, for example, a shortening of the reaction time in proportion to the increase in the amount of the catalyst, cannot be expected. Namely, part of the catalyst is wasted, resulting in economical inefficiency.

The reaction conditions are not particularly limited. However, the acrylic ester and the oxyacrylate monomer as the starting material contain vinyl group in a molecule, and easily undergo polymerization. Therefore, when reacting such an acrylic ester with the compound containing hydroxyl group, it is necessary to add a polymerization inhibitor and molecular oxygen to the system of reaction in order to restrain the polymerization of the acrylic ester and the oxyacrylate monomer.

The polymerization inhibitor is not particularly limited. Examples are hydroquinone, hydroquinone monomethyl ether, p-benzoquinone, t-butyl catechol, and phenothiazine. These polymerization inhibitors may be used alone, or in combinations of more than one kind of the polymerization inhibitors. Although the amount of the polymerization inhibitor is not particularly limited, the proportion of the polymerization inhibitor to the acrylic ester is preferably, for example, within a range of from 0.001 weight percent to 5 weight percent. An example of the molecular oxygen is air. If air is used, it is desirable to blow the air into the system of reaction, i.e., into the acrylic ester (bubbling). In order to sufficiently restrain the polymerization, it is necessary to use the polymerization inhibitor and the molecular oxygen together.

It is possible to carry out the reaction without a solvent or in the presence of a solvent. Examples of such a solvent are: ketones such as methyl ethyl ketone; ethers such as dipropyl ether; and aromatic hydrocarbons such as benzene, toluene, xylene, and chlorobenzene, and aliphatic hydrocarbons such as cyclohexane, hexanes, methyl cyclohexane and heptane. The solvent is not particularly limited if it does not interfere with the reaction. The amount of the solvent is not particularly limited.

The reaction temperature is not particularly limited. However, in order to restrain the polymerization, the reaction temperature is preferably within a range of from 0° C. to 150° C., and more preferably within a range of from 40° C. to 120° C. If the reaction temperature is lower than 0° C., the reaction time becomes too long, preventing efficient preparation of oxyacrylate monomers. On the other hand, if the reaction temperature is higher than 150° C., the polymerization cannot be restrained. The reaction time may be suitably decided depending on the reaction temperature, the kinds, combinations and amounts of the acrylic ester, compound containing hydroxyl group, solvent and catalyst so as to complete the reaction. The reaction pressure is not particularly limited, and the reaction may be performed under normal pressure (atmospheric pressure), reduced pressure or increased pressure.

Moreover, since this reaction is a dehydrating reaction, it is desirable to swiftly remove water generated by the reaction from the system of reaction. The method for removing water is not particularly limited. For example, water can be easily removed from the reaction solution by forming an azeotropic mixture with the compound containing hydroxyl group or the solvent. It is also possible to carry out the reaction without removal of water.

After the reaction, the reaction product, i.e., a desired oxyacrylate monomer is easily obtained by purifying the reaction solution. The purifying means is not particularly limited, and for example, the reaction solution is purified by performing extraction using an extractant and then removing the extractant. Examples of the extractant are: aliphatic hydrocarbons such as hexanes, cyclohexane, and methyl cyclohexane; and aromatic hydrocarbons such as benzene, toluene, and xylene. The extractant is not particularly limited if it dissolves the reaction product, and does not dissolve together with unreacted product, by-product other than the reaction product and the catalyst. The method for removing the extractant is not particularly limited, and various methods can be used, for example, distillation and evaporation. As another purifying means, it is also possible to perform separation and purification by distillation, or so-called column chromatography.

As described above, a novel method for preparing the novel oxyacrylate monomer of the present invention is a method of heating acrylic ester of general formula (13) and a compound containing hydroxyl group of general formula (14) under the presence of a polymerization inhibitor, molecular oxygen, and an acid catalyst (more preferably, protonic acid).

With this preparation method of the present invention, since a halogen halide is not formed as a by-product during the preparation of the oxyacrylate monomer, it is possible to prevent problems caused by the conventional preparation methods, for example, corrosion of a manufacturing device and environmental distraction. Moreover, in oxyacrylate monomers prepared by the method of the present invention, since a side chain portion derived from the compound containing hydroxyl group is bonded together with a skeleton portion derived from the acrylic ester by ether linkage, the oxyacrylate monomers are not hydrolyzed and the side chain portion is not eliminated. The oxyacrylate monomers prepared by the above method have excellent polymerization property and are suitably used as starting material of the cement dispersing agent.

For a fuller understanding of the nature and advantages of the invention, reference should be made to the ensuing detailed description taken in conjunction with the accompanying drawings.

DESCRIPTION OF THE PREFERRED EMBODIMENTS

The following examples and comparative examples are presented to more specifically explain the present invention. However, the present invention is not limited to those examples. The terms "part" and "percent" used in the following description represent "weight part" and "weight percent", respectively.

EXAMPLE 1

130 grams of ethyl-α-hydroxymethyl acrylate as acrylic ester, 150 grams of toluene as a solvent, 1.4 grams of boron trifluoride ethyl ether complex as a catalyst, and 0.08 grams of hydroquinone as a polymerization inhibitor were loaded and agitated in a 1000 ml pressure resistant reaction vessel having a thermometer, a gas blowing pipe and an agitator. Subsequently, after blowing nitrogen gas as an inactive gas into the reaction vessel to have a pressure of 2.5 kg/cm$^2$, 88 grams of ethylene oxide as a cyclic ether compound was gradually injected into the reaction solution while keeping the temperature in the reaction vessel within a range of from 35° C. and 45° C.

After the injection, by agitating the reaction solution for two hours at 50° C., reaction was completed. After the completion of the reaction, the temperature in the vessel was brought to 40° C., the pressure was reduced to 100 mmHg, and unreacted ethylene oxide was removed. Thereafter, the reaction solution was transferred to a rotary evaporator, and toluene was removed at 70° C. under a reduced pressure of 40 mmHg. Additionally, 3 grams of magnesium oxide as an absorbent was added to the reaction solution, and the reaction solution was agitated for two hours at 50° C. so as to cause the magnesium oxide to absorb the boron trifluoride ethyl ether complex in the solution. As a result, an insoluble was obtained. Subsequently, the reaction solution was subjected to suction filtration, and purification was performed by removing the insoluble. Consequently, 58 grams of transparent pale yellow liquid was obtained.

Figure 1:
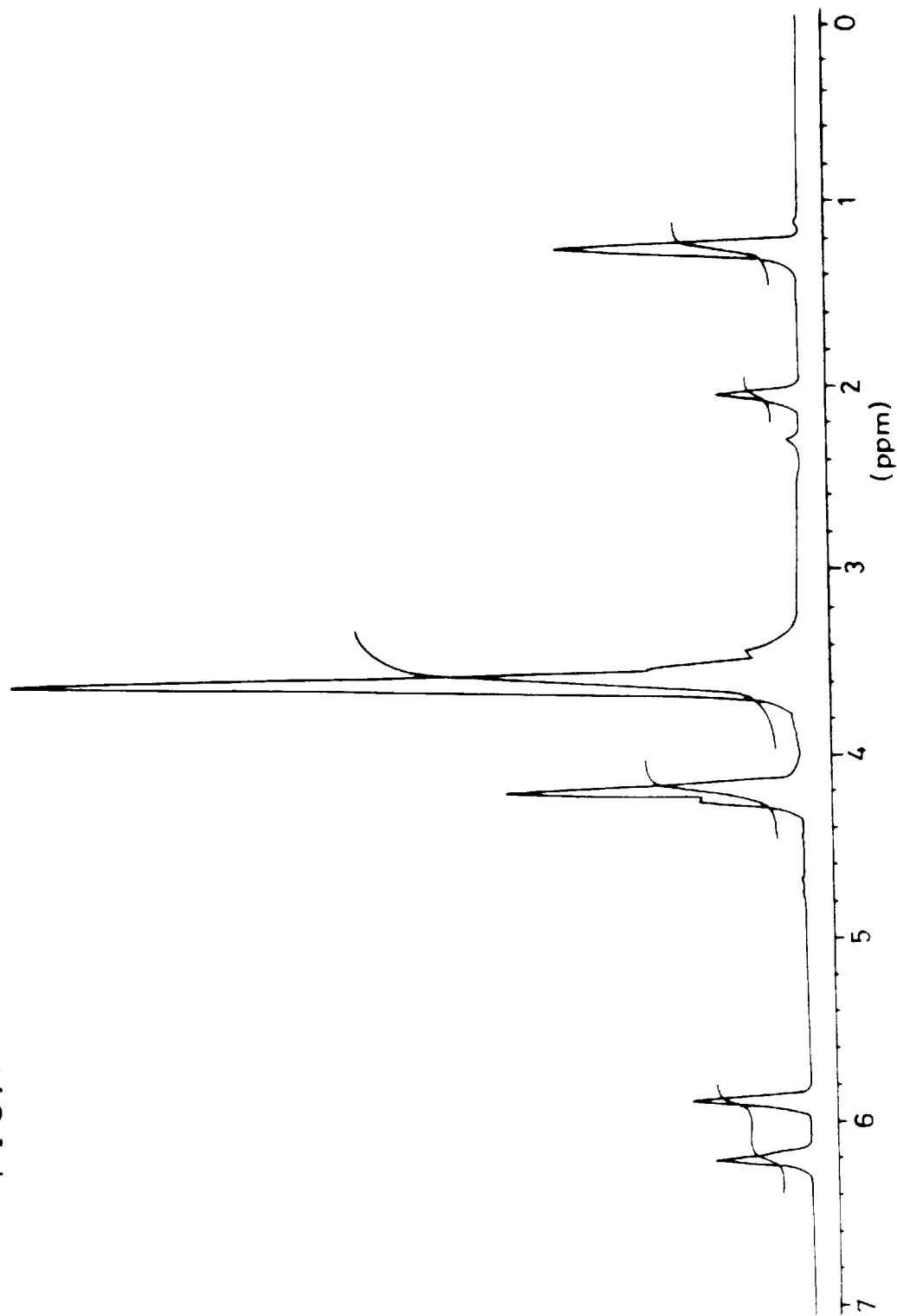
FIG. 1 is a chart of $^1$H-NMR of a reaction product obtained in one embodiment of the present invention.
Figure 2:
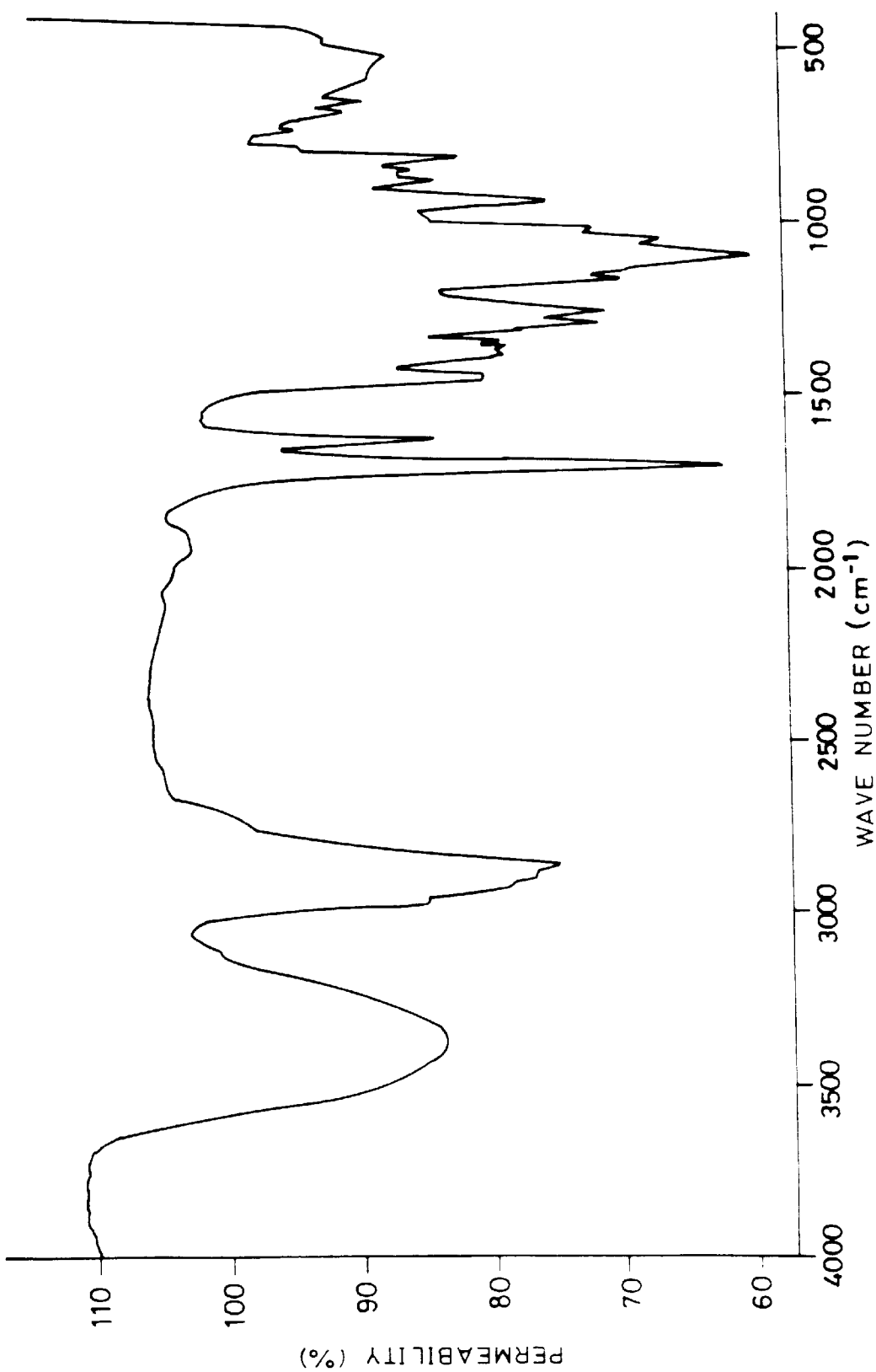
FIG. 2 is an infrared absorption spectrum of the reaction product.

Identification of the transparent pale yellow liquid was performed by measuring $^1$H-NMR and infrared absorption spectrum (IR). As a result, the transparent pale yellow liquid as a reaction product was identified as a novel acrylic ester compound of the present invention. Furthermore, the hydroxyl value of the acrylic ester compound was measured as 269 mg KOH/g by a predetermined method. It was found from the result of measurement that 1.8 moles of ethylene oxide was added per mole of ethyl-α-hydroxymethyl acrylate. In addition, the viscosity of the acrylic ester compound at 25° C. was measured as 18.5 cps by a predetermined method. The chart of $^1$H-NMR and the infrared absorption spectrum of the reaction product are shown in FIGS. 1 and 2, respectively.

EXAMPLE 2

10 grams of the acrylic ester compound which was obtained in Example 1 and 0.01 grams of 2,2'-azobisisobutyronitrile as a polymerization initiator were loaded in a test tube. After subjecting to nitrogen replacement, the test tube was closed with a stopper. Next, by heating the acrylic acid derivative to 80° C., polymerization of the acrylic ester compound was performed to form a polymer.

Figure 3:
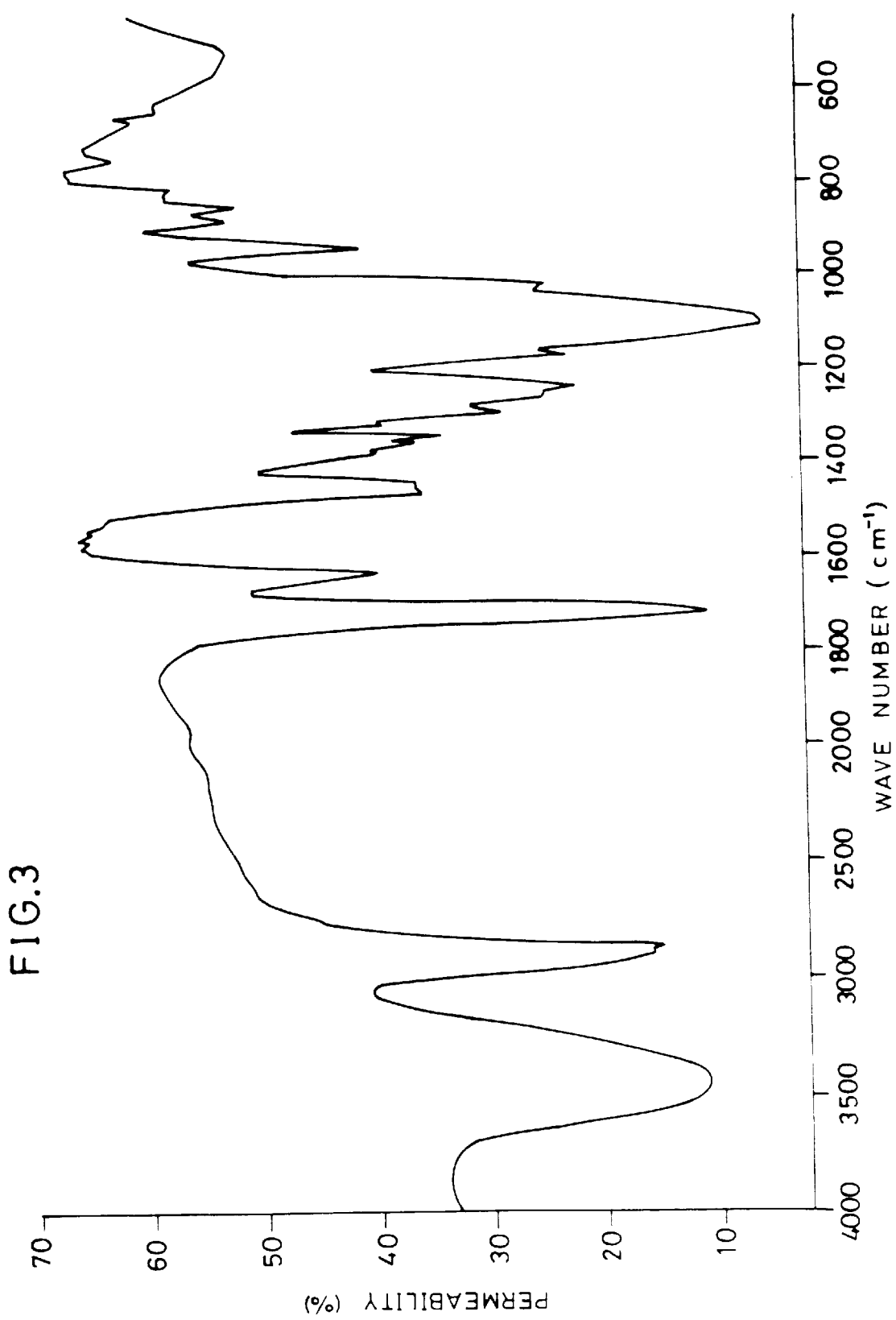
FIG. 3 is an infrared absorption spectrum of a polymer formed by polymerization of the reaction product.

Identification of the polymer was performed by measuring $^1$H-NMR and infrared absorption spectrum. As a result, the polymer was identified as a novel acrylic acid polymer of the present invention. The number-average molecular weight of the acrylic acid polymer measured by a gel permeation chromatography (GPC) was 40,000. The infrared absorption spectrum of the polymer is shown in FIG. 3.

EXAMPLE 3

6.9 grams of the acrylic ester compound which was obtained in Example 1, 3.1 grams of styrene as a copolymerizable monomer, and 0.01 grams of 2,2'-azobisisobutyronitrile as a polymerization initiator were loaded in a test tube. After subjecting to nitrogen replacement, the test tube was closed with a stopper. Next, by heating the acrylic ester compound to 80° C., polymerization of the acrylic ester compound was performed so as to yield a polymer.

Figure 4:
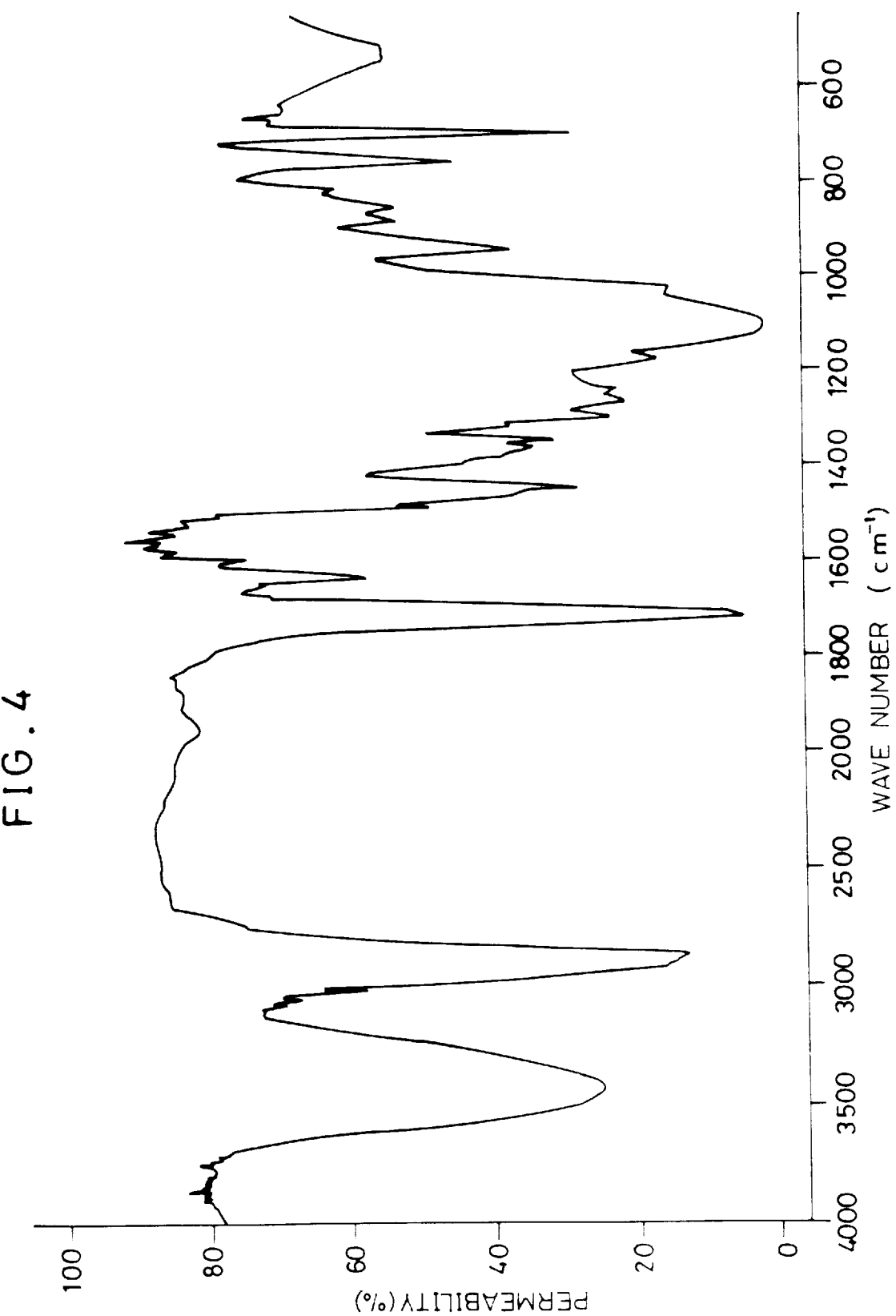
FIG. 4 is an infrared absorption spectrum of another polymer formed by polymerization of the reaction product.

Identification of the polymer was performed in the same manner as in Example 2. As a result, the polymer was identified as a novel acrylic acid polymer of the present invention. The number-average molecular weight of the acrylic acid polymer measured by gel permeation chromatography was 63,000. The infrared absorption spectrum of the polymer is shown in FIG. 4.

EXAMPLE 4

A reaction was carried out in the same manner as in Example 3 except that 3.1 grams of methyl methacrylate was used as a copolymerizable monomer instead of 3.1 grams of styrene of Example 3, and a polymer was obtained.

Figure 5:
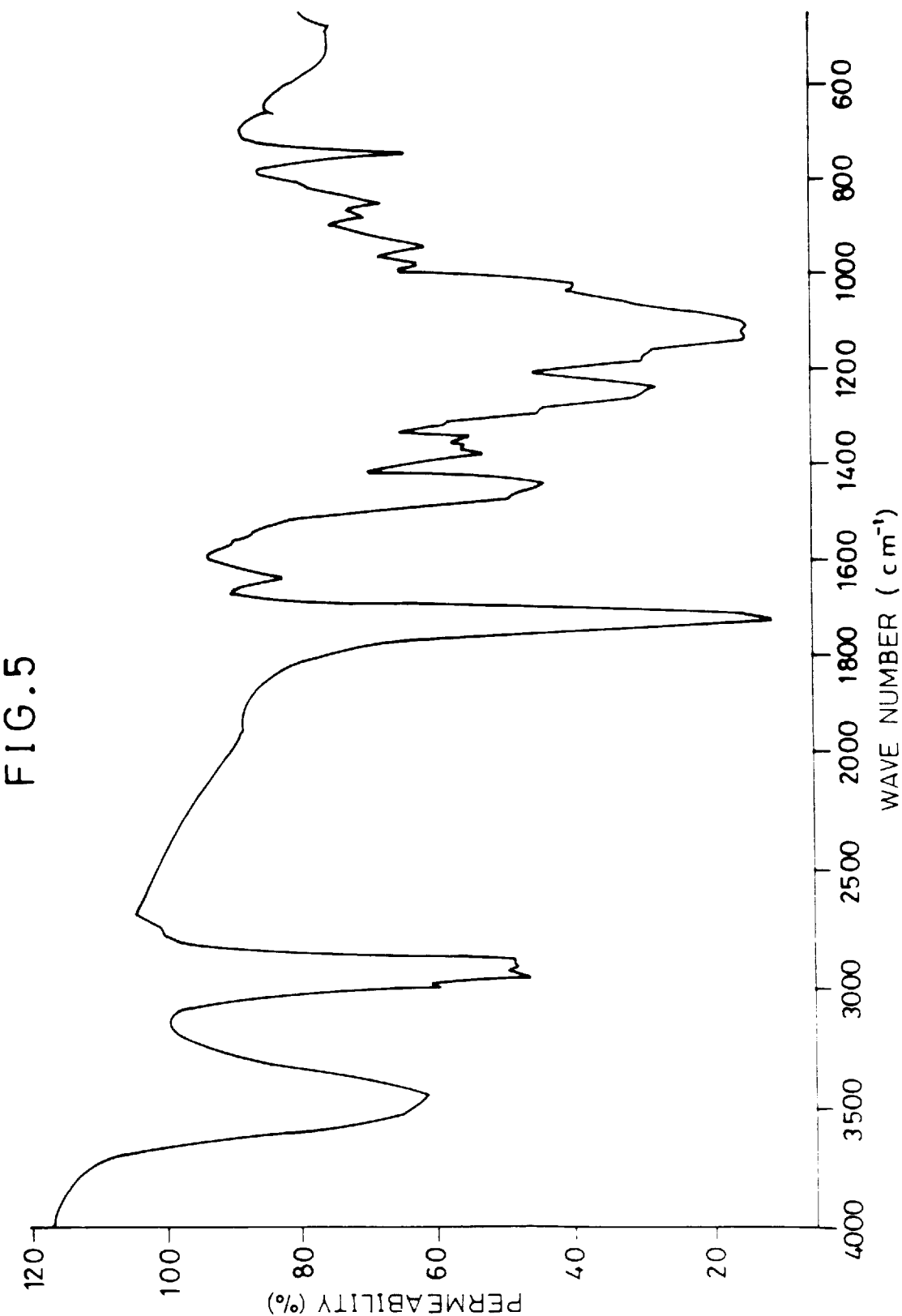
FIG. 5 is an infrared absorption spectrum of still another polymer formed by polymerization of the reaction product.

Identification of the polymer was performed in the same manner as in Example 2. As a result, the polymer was identified as a novel acrylic acid polymer of the present invention. The number-average molecular weight of the acrylic acid polymer measured by gel permeation chromatography was 59,000. The infrared absorption spectrum of the polymer is shown in FIG. 5.

EXAMPLE 5

2 moles of isophorone diisocyanate, 1 mole of triethylene glycol, and 2 moles of 2-hydroxyethyl acrylate were reacted by a predetermined method so as to yield urethane acrylate as a monomer of a ultraviolet-curing resin. Subsequently, a monomeric composition was prepared by mixing 50 grams of the urethane acrylate, 25 grams of the acrylic ester compound obtained in Example 1, 25 grams of 1,6-hexanediol diacrylate as a monomer of the ultraviolet-curing resin, and 3 grams of benzylmethyl ketal as a photopolymerization initiator (produced by Ciba-Geigy and marketed under the trade name "Irgacure 651").

Next, the monomeric composition was applied onto a steel panel (material to be coated) by a so-called spin coater so as to have a thickness of 10 μm. Thereafter, ultraviolet rays were irradiated on the monomeric composition on the steel panel from a 80 W/cm high-pressure mercury lamp which was installed on a position 10 cm higher than the position of the steel panel while moving the steel panel at a speed of 3 m/minute by a conveyer. By performing the irradiation of ultraviolet rays once under the above-mentioned conditions, the monomeric composition was ultraviolet-cured, and a tack-free cured coat was obtained.

In order to evaluate the adhesion of the cured coat to the steel panel, a so-called checker-board-patterned tape peeling test was carried out. More specifically, first, cuts were made at intervals of 1 mm on the 10 mm square cured coat on the steel panel, and the cured coat was divided into 100 small pieces (cells). Subsequently, after bonding a cellophane tape on the small pieces by pressure, the cellophane tape was forcibly peeled from the steel panel, and the number of the small pieces peeled from the steel panel by this peeling action was counted. However, no piece was peeled by the peeling action. Thus, the following equation was given number of small pieces which were not peeled off/number of divided small pieces=100/100

EXAMPLE 6

A reaction was carried out in the same manner as in Example 1 except that the amounts of ethyl-α-hydroxymethyl acrylate and ethylene oxide were changed from 130 grams to 64 grams and from 88 grams to 440 grams, respectively. As a result, 58 grams of transparent pale yellow liquid was obtained. The transparent pale yellow liquid was in a semisolid phase at ordinary room temperature (25° C.).

Figure 6:
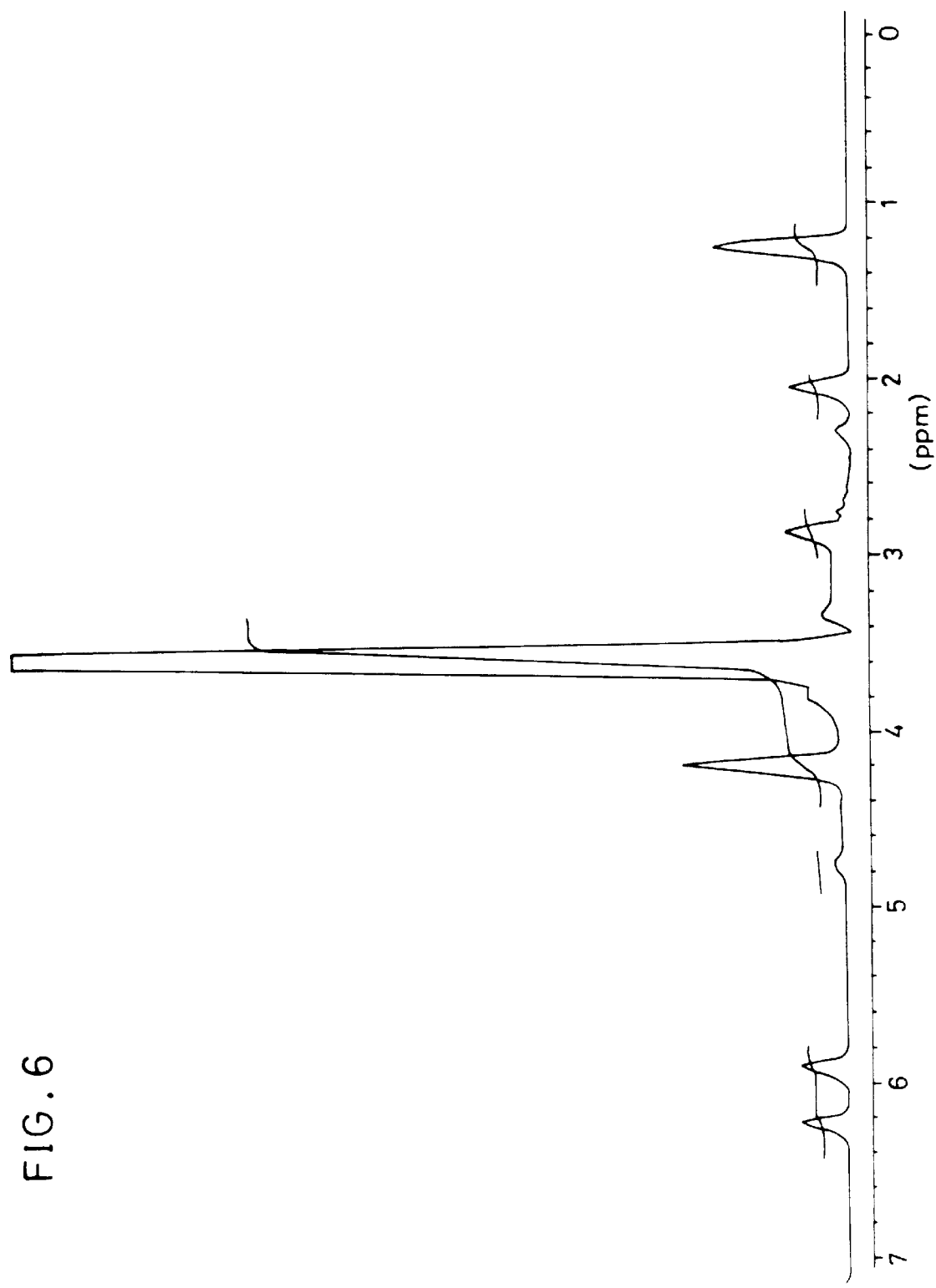
FIG. 6 is a chart of $^1$H-NMR of a reaction product obtained in another embodiment of the present invention.
Figure 7:
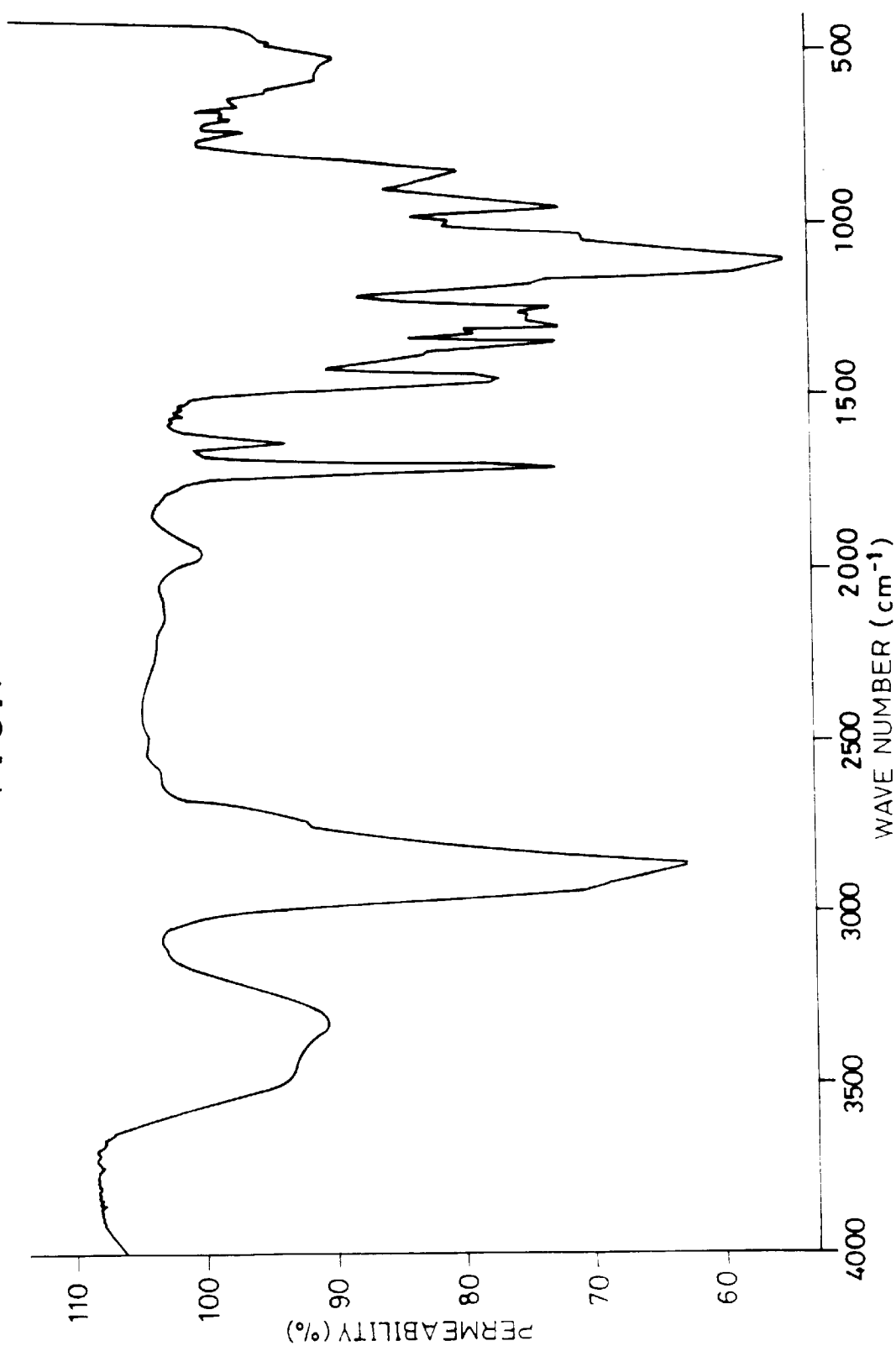
FIG. 7 is an infrared absorption spectrum of the reaction product of FIG. 6.

Identification of the transparent pale yellow liquid was performed in the same manner as in Example 1. As a result, the transparent pale yellow liquid as a reaction product was identified as a novel acrylic ester compound of the present invention. Furthermore, the hydroxyl value of the acrylic ester compound was measured as 66.6 mg KOH/g by a predetermined method. It was found from the result of measurement that 16.2 moles of ethylene oxide was added per mole of ethyl-α-hydroxymethyl acrylate. The chart of $^1$H-NMR and the infrared absorption spectrum of the reaction product are shown in FIGS. 6 and 7, respectively.

EXAMPLE 7

9.3 grams of the acrylic ester compound which was obtained in Example 6, 0.7 grams of acrylonitrile as a copolymerizable monomer, and 0.01 grams of 2,2'-azobisisobutyronitrile as a polymerization initiator were loaded in a test tube. After performing nitrogen replacement, the test tube was closed with a stopper. Next, by heating the acrylic ester compound to 80° C., polymerization of the acrylic ester compound was performed so as to yield a polymer.

Figure 8:
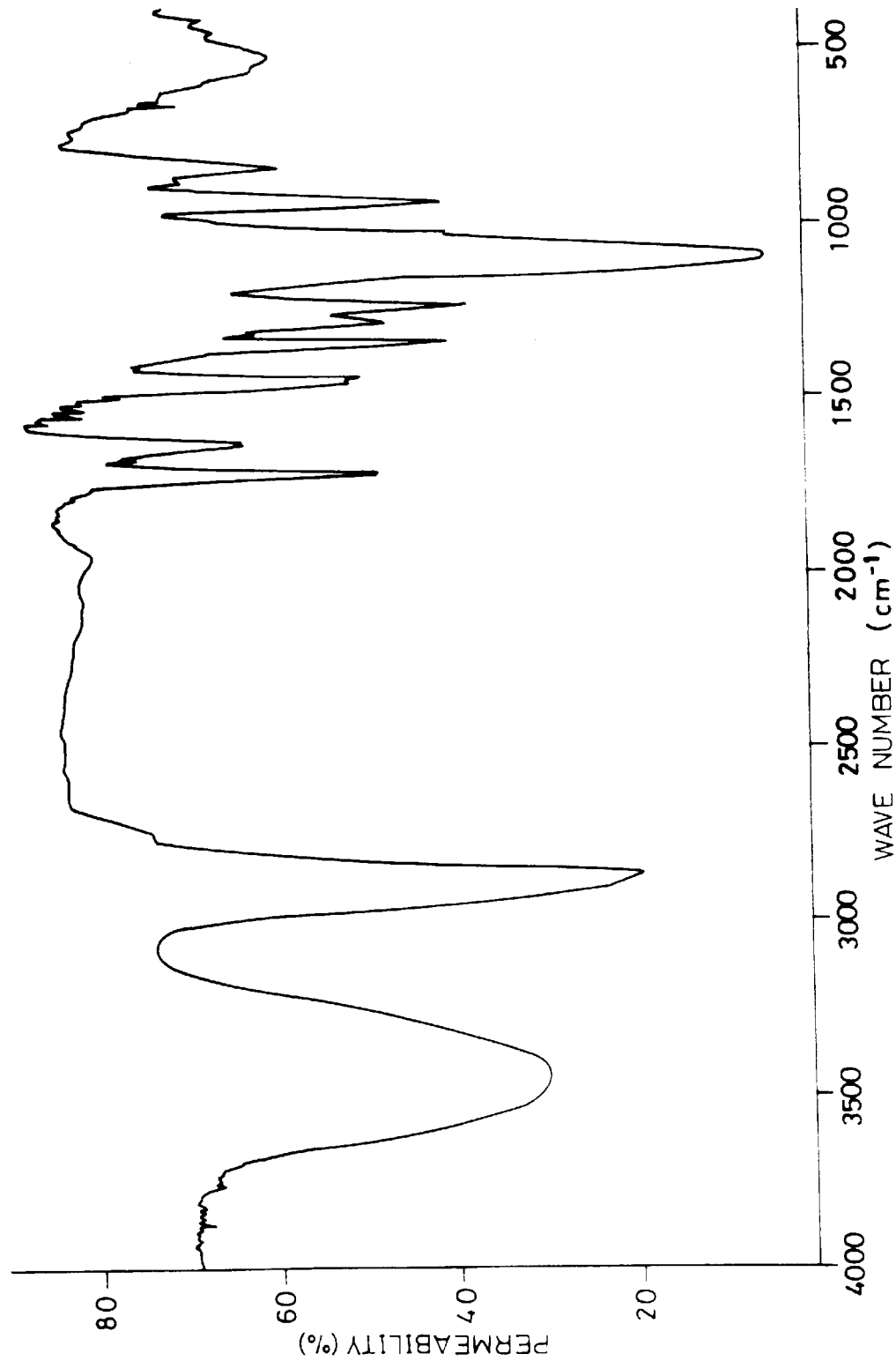
FIG. 8 is an infrared absorption spectrum of a polymer formed by polymerization of the reaction product of FIG. 6.

Identification of the polymer was performed in the same manner as in Example 2. As a result, the polymer was identified as a novel acrylic acid polymer of the present invention. The number-average molecular weight of the acrylic acid polymer measured by gel permeation chromatography was 55,000. The infrared absorption spectrum of the polymer is shown in FIG. 8.

EXAMPLE 8

39 grams of ethyl-α-hydroxymethyl acrylate as acrylic ester, 0.4 grams of tungstophosphoric acid as a catalyst, and 0.08 grams of hydroquinone as a polymerization inhibitor were loaded and agitated in a 300 ml reaction vessel having a thermometer, a gas blowing pipe, a dropping device and an agitator. Moreover, 52 grams of propylene oxide was loaded as a cyclic ether compound in the dropping device. Subsequently, air was injected into the reaction solution, and the propylene oxide in the dropping device was gradually added dropwise into the reaction solution while keeping the temperature in the reaction vessel within a range of from 45° C. to 55° C.

Thereafter, by agitating the reaction solution for two hours at 50° C., a reaction was completed. After the completion of the reaction, the temperature in the vessel was brought to 70° C., the pressure was reduced to 100 mmHg, and unreacted propylene oxide was removed in two hours. Additionally, 3 grams of magnesium oxide as an absorbent was added to the reaction solution, and then the reaction solution was agitated for two hours at 50° C. so as to cause the magnesium oxide to absorb the tungstophosphoric acid in the solution. As a result, an insoluble was formed. Next, the reaction solution was subjected to suction filtration to remove the insoluble. Consequently, 58 grams of transparent pale yellow liquid was obtained.

Figure 9:
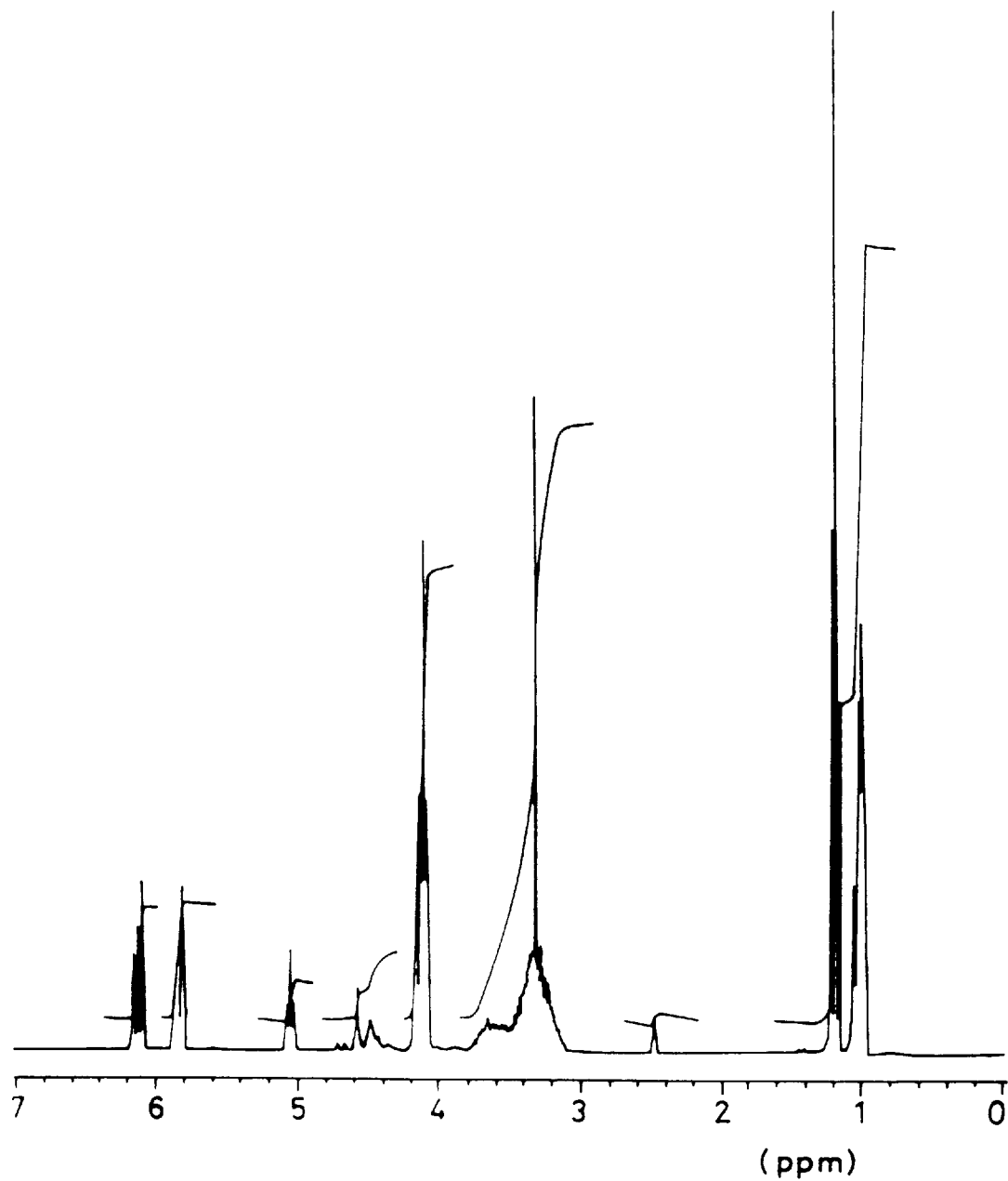
FIG. 9 is a chart of $^1$H-NMR of a reaction product obtained in still another embodiment of the present invention.
Figure 10:
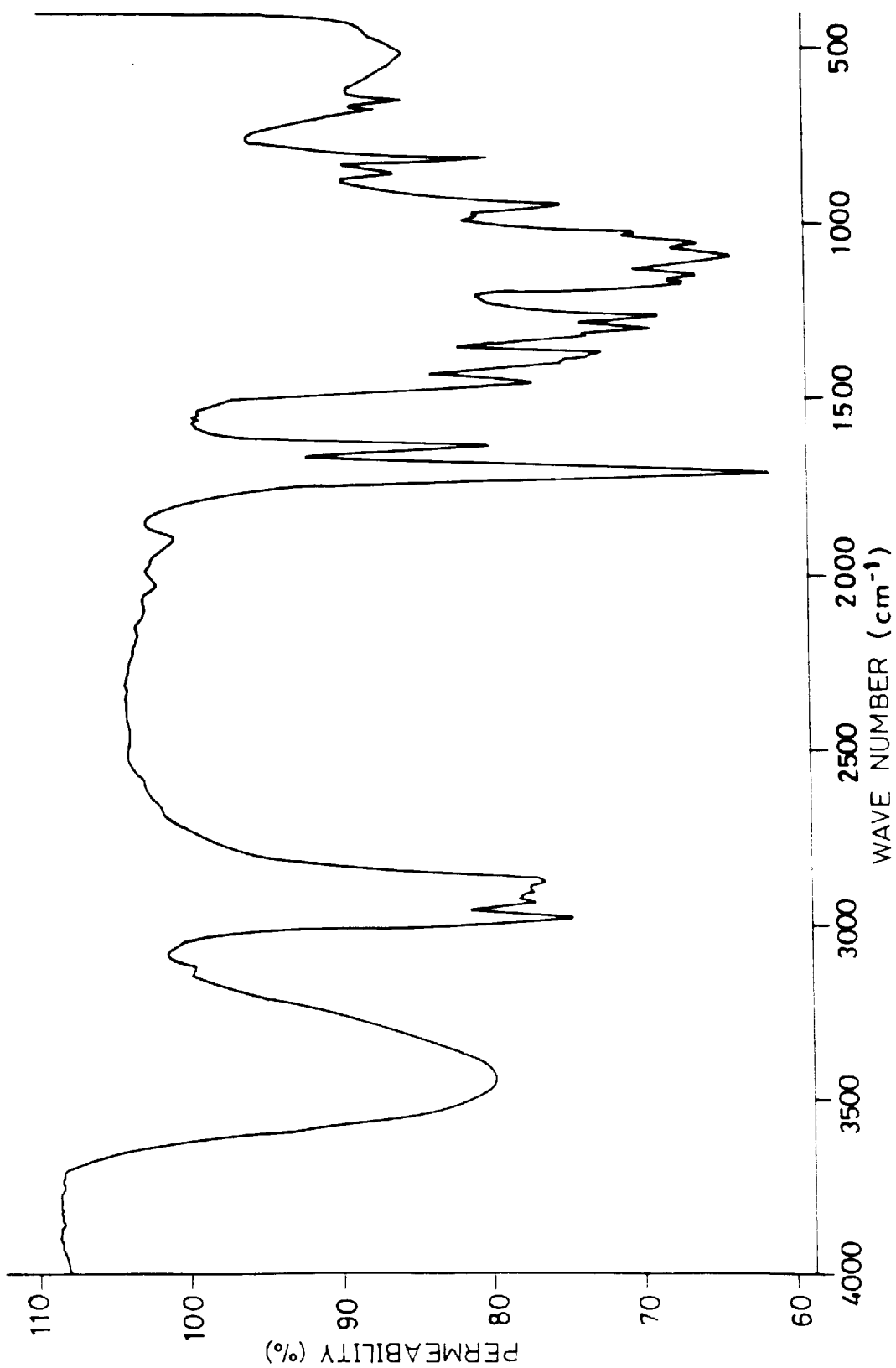
FIG. 10 is an infrared absorption spectrum of the reaction product of FIG. 9.

Identification of the transparent pale yellow liquid was performed in the same manner as in Example 1. As a result, the transparent pale yellow liquid as a reaction product was identified as a novel acrylic ester compound of the present invention. Furthermore, the hydroxyl value of the acrylic ester compound was measured as 221.4 mg KOH/g by a predetermined method. It was found from the result of measurement that 2.1 moles of propylene oxide was added per mole of ethyl-α-hydroxymethyl acrylate. The viscosity of the acrylic ester compound at 25° C. was measured as 14.7 cps by a predetermined method. The chart of $^1$H-NMR and the infrared absorption spectrum of the reaction product are shown in FIGS. 9 and 10, respectively.

EXAMPLE 9

8.0 grams of the acrylic ester compound which was obtained in Example 8, 2.0 grams of acrylonitrile as a copolymerizable monomer, and 0.003 grams of 2,2'-azobisisobutyronitrile as a polymerization initiator were loaded in a test tube. After performing nitrogen replacement, the test tube was closed with a stopper. Next, by heating the acrylic acid derivative to 80° C., polymerization of the acrylic ester compound was performed so as to yield a polymer.

Figure 11:
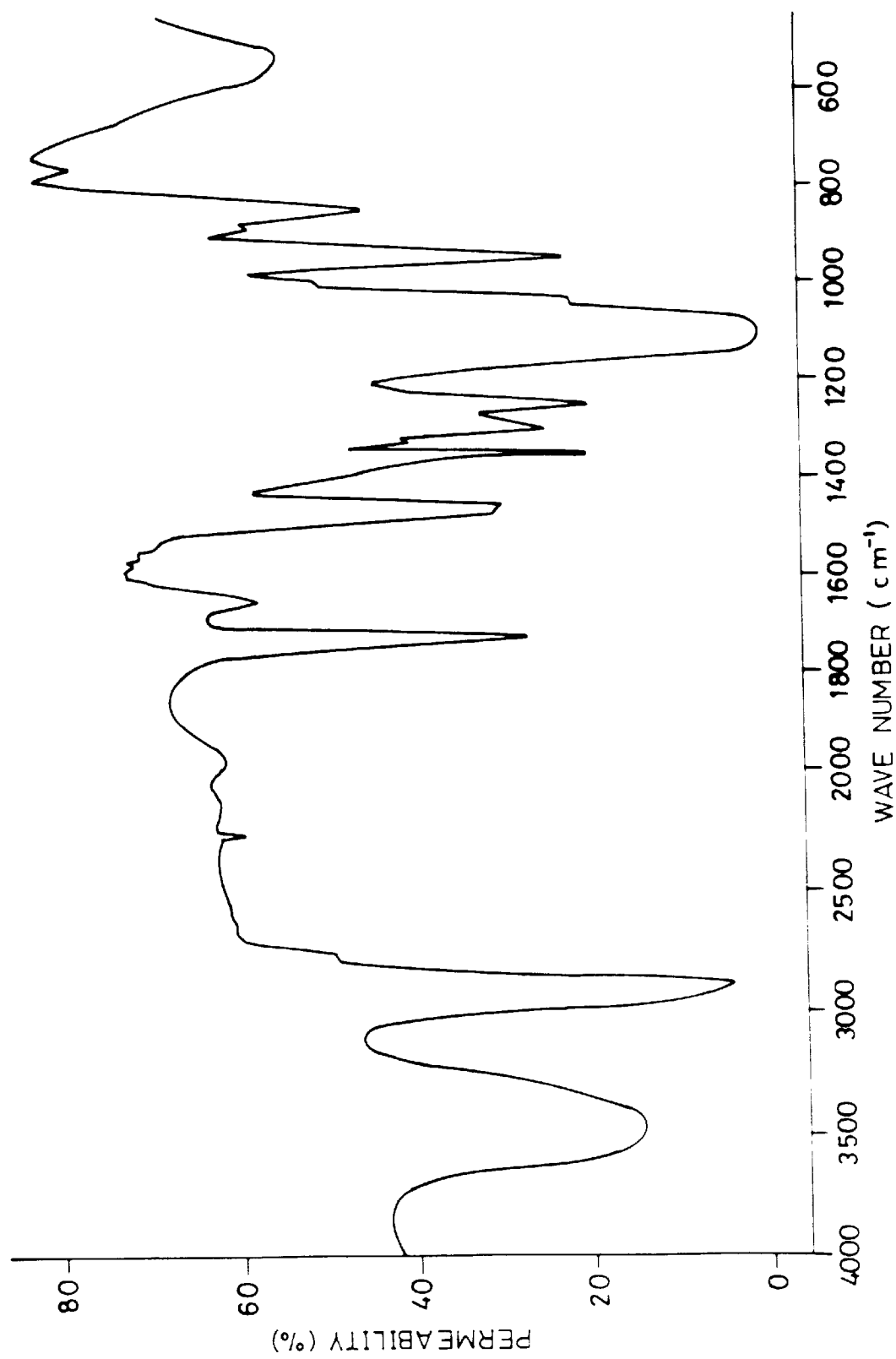
FIG. 11 is an infrared absorption spectrum of a polymer formed by polymerization of the reaction product of FIG. 9.

Identification of the polymer was performed in the same manner as in Example 2. As a result, the polymer was identified as a novel acrylic acid polymer of the present invention. The number-average molecular weight of the acrylic acid polymer measured by the gel permeation chromatography was 51,000. The infrared absorption spectrum of the polymer is shown in FIG. 11.

Comparative Example 1

A comparative monomeric composition was prepared in the same manner as in Example 5 without using the acrylic ester compound of Example 5. More specifically, the comparative monomeric composition was prepared by mixing urethane acrylate and 1,6-hexanediol diacrylate as monomers of a ultraviolet-curing resin with benzylmethyl ketal as a photopolymerization initiator.

Next, a comparable cured coat was obtained by ultraviolet-curing the comparable monomeric composition in the same manner as in Example 5. In order to evaluate the adhesion of the comparative cured coat to the steel panel, a so-called checker-board-patterned tape peeling test was carried out. 68 small pieces were peeled off by the peeling action. Thus, the following equation was given number of small pieces which were not peeled off/number of divided small pieces=32/100

EXAMPLE 10

150 grams of water and 1.5 grams of sodium hydroxide as a catalyst were loaded and agitated in a 1000 ml reaction vessel having a thermometer, a gas blowing pipe, a dropping device and an agitator. Moreover, 30 grams of the acrylic ester compound obtained in Example 2 was loaded in the dropping device. Subsequently, the acrylic ester compound in the dropping device was gradually added dropwise into the reaction vessel while keeping the temperature in the reaction vessel at 80° C.

Thereafter, by agitating the reaction solution for two hours at 80° C., a reaction was completed. After the completion of the reaction, the temperature in the vessel was brought to 90° C., the pressure was reduced to 40 mmHg, and water and by-produced ethyl alcohol were removed. Consequently, 58 grams of transparent pale yellow liquid was obtained.

Figure 12:
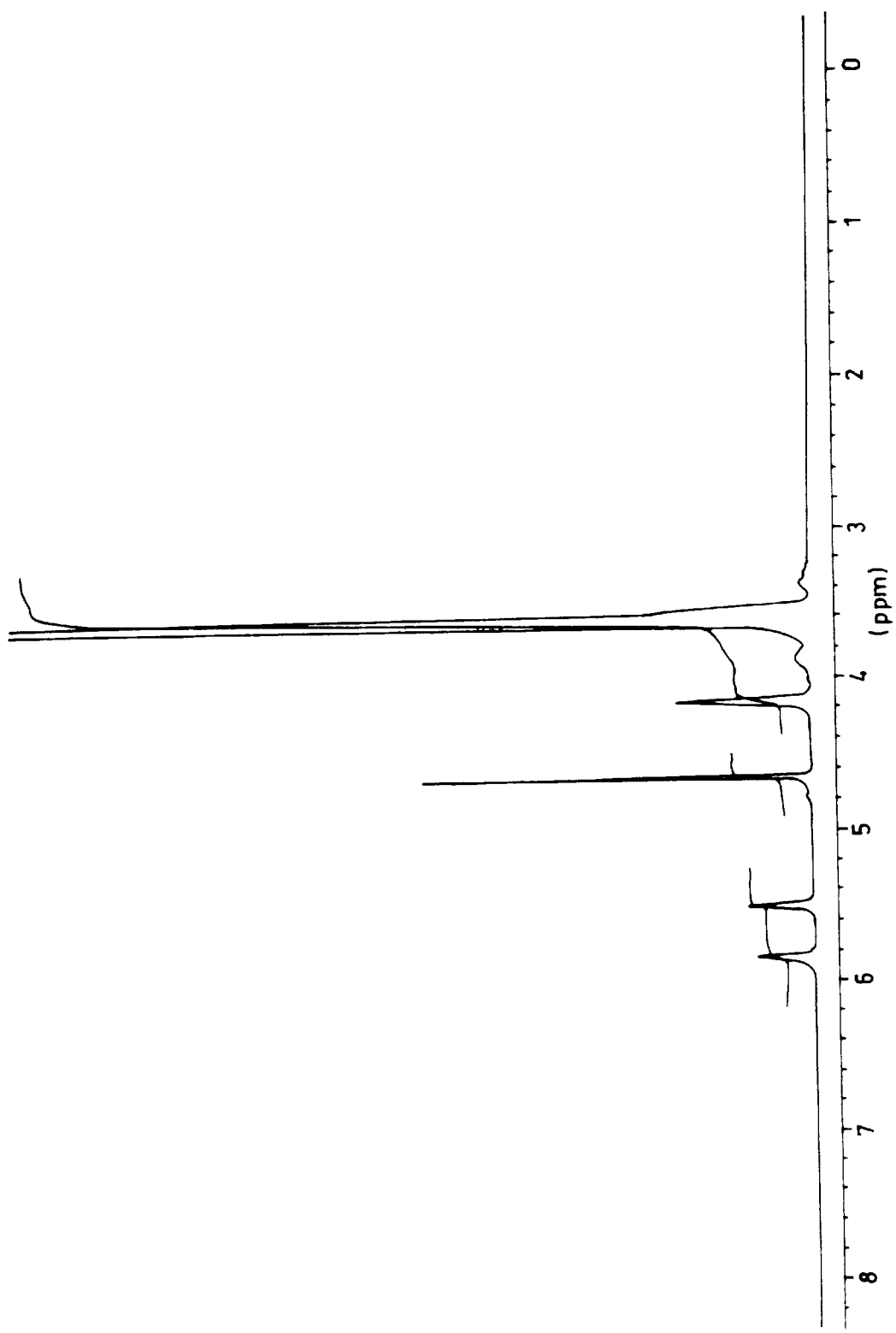
FIG. 12 is a chart of $^1$H-NMR of a reaction product obtained in yet another embodiment of the present invention.

Identification of the transparent pale yellow liquid was performed in the same manner as in Example 1. As a result, the transparent pale yellow liquid as a reaction product was identified as a novel acrylic acid compound of the present invention. The chart of $^1$H-NMR of the reaction product is shown in FIG. 12.

EXAMPLE 11

459 parts water was loaded and agitated in a glass reaction vessel having a thermometer, an agitator, dropping funnels, a nitrogen introduction pipe, and a reflux condenser. Moreover, a monomeric composition formed by 282 parts sodium-α-(hydroxypolyethylene glycoxy methyl) acrylate (the average number of added moles of ethylene oxide was 10) as an acrylic acid compound, 24 parts acrylic acid as a copolymerizable monomer and by 459 parts water, 122 parts 7 percent ammonium persulfate aqueous solution as a polymerization initiator, and 122 parts 3.5 percent sodium hydrogen sulfite as a promotor were separately loaded in the dropping funnels. Subsequently, after performing nitrogen replacement, the temperature of the reaction vessel was brought to 50° C. under the atmosphere of nitrogen, and the monomeric composition, the 7 percent ammonium persulfate aqueous solution and the 3.5 percent sodium hydrogen sulfite in the dropping funnels were respectively added dropwise into the reaction vessel in four hours.

Thereafter, 31 parts of the 7 percent ammonium persulfate aqueous solution and 31 parts of the 3.5 percent sodium hydrogen sulfite were further added dropwise into the reaction vessel in one hour. Subsequently, the reaction solution was further agitated for 3 hours while keeping the temperature in the reaction vessel at 50° C. to complete a polymerization reaction of the acrylic acid compound. Consequently, a copolymer aqueous solution was obtained.

Figure 13:
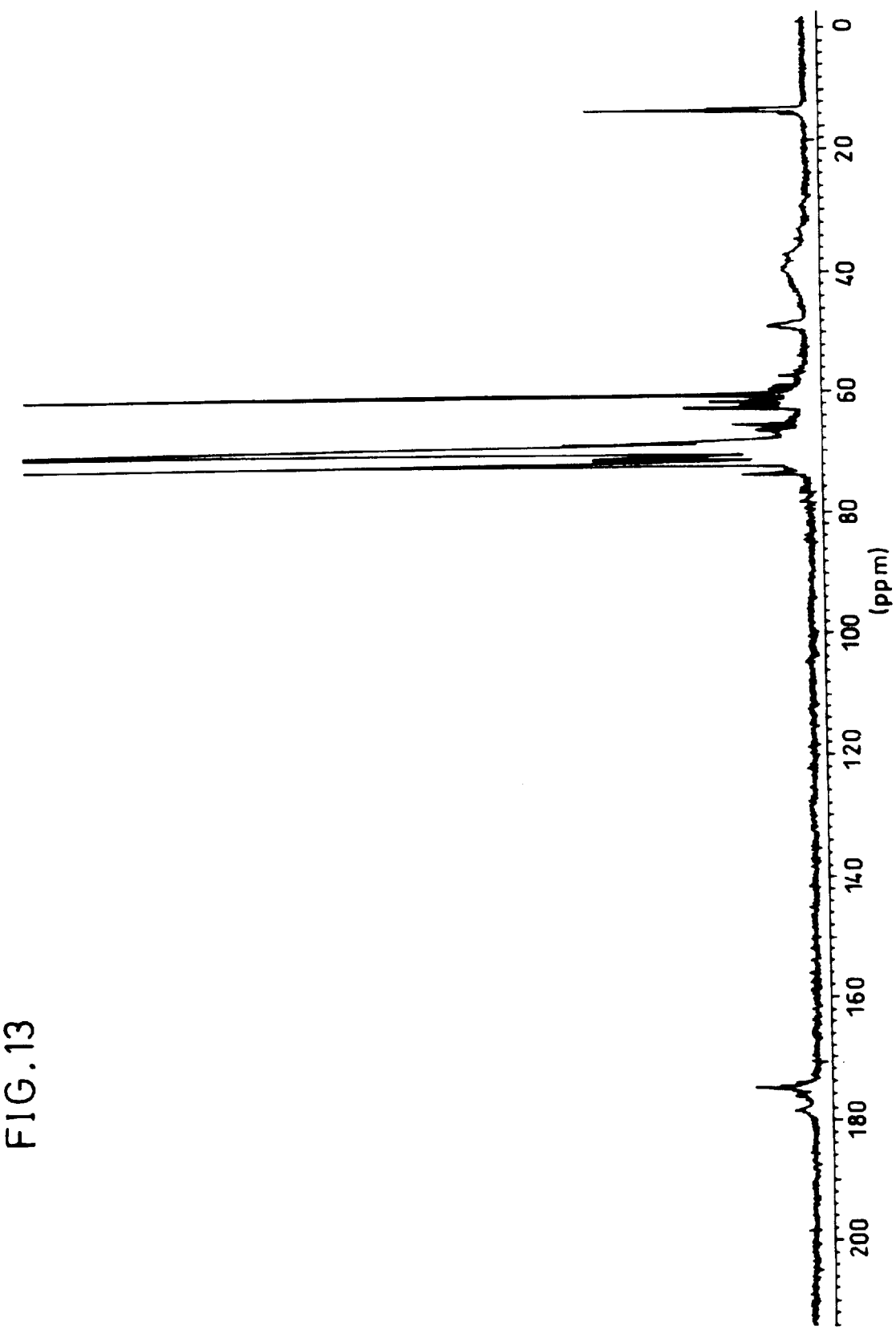
FIG. 13 is a chart of $^{13}$C-NMR of a reaction product obtained in another embodiment of the present invention.

Identification of the copolymer aqueous solution was performed by measuring $^{13}$C-NMR. As a result, the copolymer aqueous solution was identified as a novel acrylic acid polymer of the present invention. The chart of $^{13}$C-NMR of the reaction product is shown in FIG. 13. The number-average molecular weight of the acrylic acid polymer was measured as 15,000 by a predetermined method.

EXAMPLE 12

The same reaction as that of Example 11 was performed in the same manner except that 285 parts ethyl-α-(hydroxypolyethylene glycoxy methyl) acrylate (the average number of added moles of ethylene oxide was 10) as an acrylic ester compound was used instead of the sodium-α-(hydroxypolyethylene glycoxy methyl) acrylate. Consequently, a copolymer aqueous solution was obtained. The number-average molecular weight of the copolymer solution was 23,000.

Subsequently, after transferring the copolymer aqueous solution to a 1000 ml autoclave, 69 parts 48 percent sodium hydroxide as an alkaline substance was added, and hydrolyzing was performed for 6 hours at 150° C. Thereafter, by forming an azeotrope of water and ethyl alcohol generated by hydrolyzing and removing 70 parts distilled liquid, a copolymer was obtained.

Figure 14:
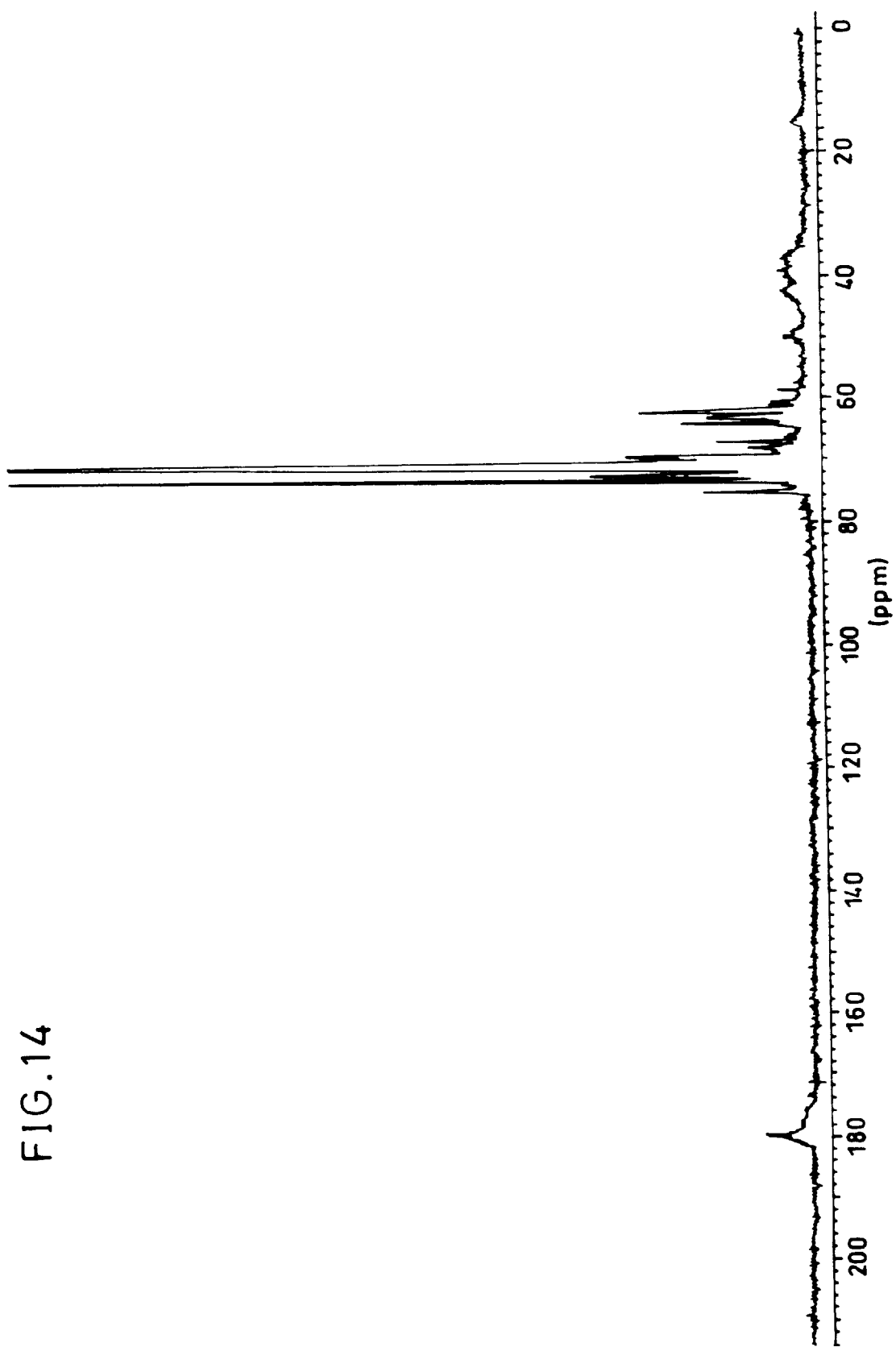
FIG. 14 is a chart of $^{13}$C-NMR of a reaction product obtained in still another embodiment of the present invention.

Identification of the copolymer was performed by the same method as in Example 11. As a result, the copolymer was identified as a novel acrylic acid polymer of the present invention. The chart of $^{13}$C-NMR of the reaction product is shown in FIG. 14.

As clearly shown by the results of Examples 1 to 4 and 6 to 12, it is possible to easily prepare novel acrylic acid derivatives (the acrylic acid compounds and the acrylic ester compounds) and novel acrylic acid polymers by the methods explained in the above examples. Furthermore, it was found from the results of Example 5 and Comparative Example 1 that the acrylic acid derivatives are suitably used as a so-called paint adhesion improving agent.

EXAMPLE 13

130 grams of ethyl-α-hydroxymethyl acrylate as acrylic ester, 100 grams of toluene as a solvent, 1.4 grams of boron trifluoride ethyl ether complex as a catalyst, and 0.065 grams of hydroquinone as a polymerization inhibitor were loaded and agitated in a 1000 ml pressure resistant reaction vessel having a thermometer, a gas blowing pipe and an agitator. Subsequently, after blowing nitrogen gas as an inactive gas into the reaction vessel to have a pressure of 2.5 kg/cm$^2$, 242 grams of ethylene oxide as a cyclic ether compound was gradually injected into the reaction solution while keeping the temperature in the reaction vessel within a range of from 35° C. to 45° C.

After the injection, by agitating the reaction solution for two hours at 50° C., a reaction was completed. After the completion of the reaction, the temperature in the vessel was brought to 40° C., the pressure was reduced to 100 mmHg, and unreacted ethylene oxide was removed. Thereafter, 3 grams of magnesium oxide as an absorbent was added to the reaction solution, and the reaction solution was agitated for two hours at 50° C. so as to cause the magnesium oxide to absorb the boron trifluoride ethyl ether complex in the solution. As a result, an insoluble was formed. Subsequently, the reaction solution was subjected to suction filtration so as to remove the insoluble. Next, the reaction solution was transferred to a rotary evaporator, and toluene was removed at 70° C. under a reduced pressure of 40 mmHg. Consequently, 342 grams of transparent pale yellow liquid as a reaction product, i.e., coarse acrylic ester compound, was obtained.

The hydroxyl value of the coarse acrylic ester compound was measured as 156.4 mg KOH/g by a predetermined method. It was found from the result of measurement that 5.2 moles of ethylene oxide was added per mole of ethyl-α-hydroxymethyl acrylate. The components of the coarse acrylic ester compound were analyzed by liquid chromatography. The results of the analysis are shown in Table 1.

EXAMPLE 14

100 grams of the coarse acrylic ester compound prepared in Example 13 and 10 grams of water were loaded into a 500 ml separating funnel. After shaking the separating funnel 10 times, the separating funnel was arranged to stand still at room temperature. Immediately, the solution in the separating funnel separated into two layers. 30 minutes later, a water layer as the lower layer was removed. Thereafter, the upper layer remaining in the separating funnel, i.e., an acrylic ester compound layer, was transferred to a rotary evaporator, and water was removed at 40 mmHg and 50° C. As a result, 67 grams of transparent pale yellow liquid was obtained. The components of the transparent pale yellow liquid were analyzed using liquid chromatography. The results of the analysis are shown in Table 1.

EXAMPLE 15

100 grams of the coarse acrylic ester compound prepared in Example 13, 100 grams of water, and 1000 grams of toluene were loaded into a 2000 ml separating funnel. After shaking the separating funnel 10 times, the separating funnel was arranged to stand still at room temperature. Immediately, the solution in the separating funnel separated into two layers. 30 minutes later, a water layer as the lower layer was removed. Thereafter, the upper layer remaining in the separating funnel, i.e., an acrylic ester compound layer was transferred to a rotary evaporator, and water and toluene were removed at 40 mmHg and 50° C. As a result, 78 grams of transparent pale yellow liquid was obtained. The components of the transparent pale yellow liquid were analyzed using liquid chromatography. The results of the analysis are shown in Table 1.

EXAMPLE 16

100 grams of the coarse acrylic ester compound prepared in Example 13, 200 grams of water, and 200 grams of ethyl acetate were loaded into a 1000 ml separating funnel. After shaking the separating funnel 10 times, the separating funnel was arranged to stand still at room temperature. Immediately, the solution in the separating funnel separated into two layers. 30 minutes later, a water layer as the lower layer was removed. Thereafter, the upper layer remaining in the separating funnel, i.e., an acrylic ester compound layer, was transferred to a rotary evaporator, and water and ethyl acetate were removed at 40 mmHg and 50° C. As a result, 44 grams of transparent pale yellow liquid was obtained. The components of the transparent pale yellow liquid were analyzed using liquid chromatography. The results of the analysis are shown in Table 1.

EXAMPLE 17

130 grams of ethyl-α-hydroxymethyl acrylate, 1.4 grams of tungstophosphoric acid as a catalyst, and 0.065 grams of hydroquinone were loaded and agitated in a 1000 ml reaction vessel having a thermometer, a gas blowing pipe, a dropping device and an agitator. Moreover, 203 grams of propylene oxide was loaded as a cyclic ether compound in the dropping device. Subsequently, air was injected into the reaction solution, and the propylene oxide in the dropping device was gradually added dropwise into the reaction solution while keeping the temperature in the reaction vessel within a range of from 45° C. to 55° C.

Thereafter, by agitating the reaction solution for two hours at 50° C., reaction was completed. After the completion of the reaction, the temperature in the vessel was brought to 70° C., the pressure was reduced to 100 mmHg, and unreacted propylene oxide was removed in two hours. Additionally, 3 grams of magnesium oxide was added to the reaction solution, and then the reaction solution was agitated for two hours at 50° C. so as to cause the magnesium oxide to absorb the tungstophosphoric acid in the solution. As a result, an insoluble was formed. Next, the reaction solution was subjected to suction filtration to remove the insoluble. Consequently, 298 grams of transparent pale yellow liquid as a reaction product, i.e., coarse acrylic ester compound, was obtained.

The hydroxyl value of the coarse acrylic ester compound was measured as 181.1 mg KOH/g by a predetermined method. It was found from the result of measurement that 3.1 moles of propylene oxide was added per mole of ethyl-α-hydroxymethyl acrylate. The components of the coarse acrylic ester compound were analyzed using liquid chromatography. The results of the analysis are shown in Table 1.

EXAMPLE 18

100 grams of the coarse acrylic ester compound prepared in Example 17, 200 grams of water, and 500 grams of toluene were loaded into a 1000 ml separating funnel. After shaking the separating funnel 10 times, the separating funnel was arranged to stand still at room temperature. Immediately, the solution in the separating funnel separated into two layers. 30 minutes later, a water layer as the lower layer was removed. Thereafter, the upper layer remaining in the separating funnel, i.e., an acrylic ester compound layer, was transferred to a rotary evaporator, and water and toluene were removed at 40 mmHg and 50° C. As a result, 87 grams of transparent pale yellow 80 weight percent aqueous solution was obtained. The components of the transparent pale yellow liquid were analyzed using liquid chromatography. The results of the analysis are shown in Table 1.

TABLE 1

| Example | 13 | 14 | 15 | 16 | 17 | 18 |
|---|---|---|---|---|---|---|
| Acrylic ester derivative (weight %) | 83.1 | 88.1 | 87.9 | 94.5 | 84.1 | 87.5 |
| Glycol (weight %) | 3.2 | 0.0 | 0.0 | 0.0 | 2.7 | 0.0 |
| Glycol monoethyl ether (weight %) | 2.5 | 0.0 | 0.0 | 0.0 | 1.1 | 0.0 |
| α-hydroxy ethyl acrylate (weight %) | 6.1 | 6.6 | 6.7 | 5.1 | 8.2 | 8.5 |
| Ether dimer (weight %) | 1.7 | 1.8 | 1.9 | 0.1 | 1.7 | 1.8 |
| Acetal dimer (weight %) | 1.2 | 1.3 | 1.3 | 0.1 | 1.0 | 1.0 |
| Ester-type dimer (weight %) | 2.2 | 2.2 | 2.2 | 0.2 | 1.2 | 1.2 |

As is clear from the results shown in Table 1, non-polymerizable alcohols, such as glycol and glycol monoethyl ether, contained in coarse acrylic ether compounds can be removed by purifying the coarse acrylic ether compounds by the purification method of the present invention.

EXAMPLE 19

The same reaction as in Example 13 was carried out in the same manner except that the amount of ethylene oxide as a cyclic ether compound was changed from 242 grams to 462 grams. As a result, 568 grams of transparent pale yellow liquid as a reaction product, i.e., coarse acrylic ester compound, was obtained.

The hydroxyl value of the coarse acrylic ester compound was measured as 96.9 mg KOH/g by a predetermined method. It was found from the result of measurement that 10.2 moles of ethylene oxide was added per mole of ethyl-α-hydroxymethyl acrylate.

The components of the coarse acrylic ester compound were analyzed by liquid chromatography.

In addition, 10.0 grams of the transparent pale yellow liquid measured in terms of acrylic ester compound, and 0.03 grams of 2,2'-azobisisobutyronitrile as a polymerization initiator were loaded in a test tube. After performing nitrogen replacement, the test tube was closed with a stopper. Next, by maintaining the temperature at 80° C., polymerization of the acrylic ester compound was performed so as to find whether or not gelation occurred during polymerization. The results of analysis and of the polymerization test are shown together in Table 2.

EXAMPLE 20

100 grams of the coarse acrylic ester compound prepared in Example 19 and 50 grams of hexane were loaded into a 500 ml separating funnel. After shaking the separating funnel 10 times, the separating funnel was arranged to stand still. Immediately, the solution in the separating funnel separated into two layers. 30 minutes later, an acrylic ester compound layer as the lower layer was removed. Thereafter, the acrylic ester compound was transferred to a rotary evaporator, and cyclohexane was removed at 40 mmHg and 50° C. As a result, 86 grams of transparent pale yellow liquid was obtained. The components of the transparent pale yellow liquid were analyzed using liquid chromatography.

The same polymerization test as in Example 16 was performed so as to find whether or not gelation occurred during polymerization. The results of analysis and of the polymerization test are shown together in Table 2.

EXAMPLE 21

100 grams of the coarse acrylic ester compound prepared in Example 19, 100 grams of water and 10 grams of toluene were loaded into a 500 ml separating funnel. After shaking the separating funnel 10 times, the separating funnel was arranged to stand still. Immediately, the solution in the separating funnel separated into two layers. 30 minutes later, a water layer including an acrylic ester compound layer as the lower layer was removed. Thereafter, the acrylic ester compound was transferred to a rotary evaporator, and water and toluene were removed at 40 mmHg and 70° C. As a result, 108 grams of transparent pale yellow 80 weight percent aqueous solution was obtained. The components of the aqueous solution were analyzed using liquid chromatography.

Moreover, the aqueous solution was put in a test tube so as to have 10.0 grams of the acrylic ester compound therein, and diluted with water so as to achieve 40 weight percent monomer density. Subsequently, 0.3 grams of ammonium persulfate as an polymerization initiator and 0.15 grams of sodium hydrogen sulfite were added to the test tube so as to carry out nitrogen replacement. Thereafter, the test tube was closed with a stopper, and polymerization of the acrylic ester compound was performed while keeping the temperature at 50° C. so as to confirm whether or not gelation occurred during polymerization. The results of the analysis and of the polymerization test are shown together in Table 2.

EXAMPLE 22

100 grams of the coarse acrylic ester compound prepared in Example 19, 200 grams of water and 10 grams of ethyl acetate were loaded into a 500 ml separating funnel. After shaking the separating funnel 10 times, the separating funnel was arranged to stand still at room temperature. Immediately, the solution in the separating funnel separated into two layers. 30 minutes later, a water layer containing the acrylic ester compound as the lower layer was removed. Thereafter, the solution removed from the separating funnel, i.e., the acrylic ester compound layer, was transferred to a rotary evaporator, and water and ethyl acetate were removed at 40 mmHg and 70° C. As a result, 108 grams of transparent pale yellow 80 weight percent aqueous solution was obtained. The components of the aqueous solution were analyzed using liquid chromatography. Moreover, the same polymerization test as in Example 21 was carried out to confirm whether or not gelation occurred during polymerization. The results of the analysis and of the polymerization test are shown together in Table 2.

EXAMPLE 23

100 grams of the coarse acrylic ester compound prepared in Example 19 and 50 grams of toluene were loaded into a 500 ml separating funnel. After shaking the separating funnel 10 times, the separating funnel was arranged to stand still at room temperature. However, only a uniform layer was present in the separating funnel, and no signs of separation of the liquid were observed.

EXAMPLE 24

The same reaction as in Example 14 was carried out in the same manner except that the amount of propylene oxide as a cyclic ether compound was changed from 203 grams to 319 grams. As a result, 413 grams of transparent pale yellow liquid as a reaction product, i.e., coarse acrylic ester compound was obtained.

The hydroxyl value of the coarse acrylic ester compound was measured as 126.6 mg KOH/g by a predetermined method. It was found from the result of measurement that 5.4 moles of propylene oxide was added per mole of ethyl-α-hydroxymethyl acrylate.

The components of the coarse acrylic ester compound were analyzed using liquid chromatography. Moreover, the same polymerization test as in Example 19 was carried out to confirm whether or not gelation occurred during polymerization. The results of the analysis and of the polymerization test are shown together in Table 2.

EXAMPLE 25

100 grams of the coarse acrylic ester compound prepared in Example 24 and 50 grams of cyclohexane were loaded into a 1000 ml separating funnel. After shaking the separating funnel 10 times, the separating funnel was arranged to stand still at room temperature. Immediately, the solution in the separating funnel separated into two layers. 30 minutes later, an acrylic ester compound layer as the lower layer was removed. Thereafter, the acrylic ester compound layer was transferred to a 1000 ml separating funnel, and 300 grams of water and 10 grams of toluene were added. After shaking the separating funnel 10 times, the separating funnel was arranged to stand still at room temperature. Immediately, the solution in the separating funnel separated into two layers. 30 minutes later, a water layer containing an acrylic ester compound layer as the lower layer was removed. Subsequently, the solution removed from the separating funnel, i.e., the acrylic ester compound layer, was transferred to a rotary evaporator, and water, toluene and cyclohexane were removed at 40 mmHg and 70° C. As a result, 83 grams of transparent pale yellow 80 weight percent aqueous solution was obtained. The components of the aqueous solution were analyzed using liquid chromatography. Moreover, the same polymerization test as in Example 21 was carried out to confirm whether or not gelation occurred during polymerization. The results of the analysis and of the polymerization test are shown together in Table 2.

TABLE 2

| Example | 19 | 20 | 21 | 22 | 24 | 25 |
|---|---|---|---|---|---|---|
| Acrylic ester derivative (weight %) | 83.6 | 90.7 | 73.0 | 72.7 | 86.7 | 77.5 |
| Ether dimer (weight %) | 1.6 | 0.1 | 0.0 | 0.0 | 1.5 | 0.0 |
| Acetal dimer (weight %) | 1.3 | 0.1 | 0.0 | 0.0 | 1.3 | 0.0 |
| Ester-type dimer (weight %) | 4.5 | 0.4 | 0.1 | 0.1 | 3.3 | 0.8 |
| Glycol (weight %) | 4.5 | 4.5 | 3.6 | 3.6 | 2.8 | 0.0 |
| Glycol monoethyl ether (weight %) | 3.5 | 3.5 | 2.8 | 2.8 | 2.1 | 0.0 |
| α-hydroxyethyl acrylate (weight %) | 1.0 | 0.7 | 0.6 | 0.5 | 2.3 | 1.7 |
| Water (weight %) | 0.0 | 0.0 | 19.9 | 20.3 | 0.0 | 20.0 |
| Gelation during polymerization | o | x | x | x | o | x | o : Occurred, x: Not Occurred

As is clear from the results shown in Table 2, crosslinking components, such as ether dimer, acetal dimer and ester-type dimer, contained in coarse acrylic ether compounds can be removed by purifying the coarse acrylic ether compounds by the purification method of the present invention.

EXAMPLE 26

65 grams of ethyl-α-hydroxymethyl acrylate as acrylic ester, 60 grams of methoxy ethoxy ethanol as a compound containing hydroxyl group, 150 grams of cyclohexane as a solvent, 25 grams of tungstophosphoric acid as a catalyst, and 0.08 grams of hydroquinone were loaded and agitated in a 500 ml glass reaction vessel having a thermometer, a gas blowing pipe, and an agitator. Next, air was blown into the reaction solution, and the cyclohexane was refluxed for eight hours while keeping the temperature in the reaction vessel at 90° C. so as to complete the reaction.

After the completion of the reaction, the reaction solution was washed and extracted twice with a cyclohexane-water system using a separation funnel to extract a reaction product into a cyclohexane layer. Thereafter, the cyclohexane layer was transferred to a recovery vessel, the temperature in the reaction vessel was made 50° C., the pressure therein was reduced to 40 mmHg, and the cyclohexane was removed. As a result, 73.3 grams of the reaction product was obtained.

The reaction product was analyzed by gas chromatography. The reaction product contained 71.2% ethyl-α-(methoxyethoxy) ethoxymethyl acrylate, and 21.9% 2-methoxyethoxyethyl-α-(methoxyethoxy) ethoxymethyl acrylate.

As is clear from the result of Example 26, with the method of Example 26, an oxyacrylate monomer can be easily obtained by reacting acrylic ester with a compound containing hydroxyl group under the presence of an acid as a catalyst, preferably, protonic acid.

EXAMPLE 27

459 parts water was loaded and agitated in a glass reaction vessel having a thermometer, an agitator, dropping funnels, a nitrogen introduction pipe, and a reflux condenser. Moreover, a monomeric composition formed by 282 parts sodium-α-(hydroxypolyethylene glycoxy methyl) acrylate (the average number of added moles of ethyl oxide was 10) as an oxyacrylic acid monomer, 24 parts acrylic acid as a (meth)acrylic acid monomer of general formula (10) and by 459 parts water, 122 parts 7 percent ammonium persulfate aqueous solution as a polymerization initiator, and 122 parts 3.5 percent sodium hydrogen sulfite as a promotor were separately loaded in the dropping funnels. Subsequently, after performing nitrogen replacement, the temperature of the reaction vessel was brought to 50° C. under the atmosphere of nitrogen, and the monomeric composition, the 7 percent ammonium persulfate aqueous solution and the 3.5 percent sodium hydrogen sulfite in the dropping funnels were respectively added dropwise into the reaction vessel in four hours.

Thereafter, 31 parts of the 7 percent ammonium persulfate aqueous solution and 31 parts of the 3.5 percent sodium hydrogen sulfite were further added dropwise into the reaction vessel in one hour. Subsequently, the reaction solution was further agitated for 3 hours while keeping the temperature in the reaction vessel at 50° C. to complete a polymerization reaction. Consequently, a copolymer aqueous solution as the polymer (D) was obtained. The weight-average molecular weight of the copolymer aqueous solution was 17,000.

Subsequently, 27 parts 48 percent sodium hydroxide as an alkaline substance was added to the copolymer aqueous solution so as to neutralize carboxyl group. As a result, a copolymer aqueous solution as the polymer (E) was obtained as a cement dispersing agent of the present invention (hereinafter referred to as cement dispersing agent (1)).

Next, by mixing the cement dispersing agent (1), cement, fine aggregate, coarse aggregate and water, concrete as a cement composition was obtained.

The conditions for mixing the above materials were as follows. Namely, standard mixing conditions of plain concrete containing no cement dispersing agent are a unit cement volume of 320 kg/m$^3$, a unit water volume of 203 kg/m$^3$ (the proportion of water to cement is 63.4%), and a sand percentage of 49 percent. When mixing the cement dispersing agent (1), the mixing conditions change to a unit cement volume of 320 kg/cm$^3$, a unit water volume of 166 kg/M$^3$ (the proportion of water to cement is 51.9%), and a sand percentage of 47 percent.

Normal portland cement (mixture of three formulations of equivalent weight with a specific gravity of 3.16) was used as the cement. Blended sand (with a specific gravity of 2.62 and an FM (fineness modulus) of 2.71) of land sand obtained at Oigawa River and pit sand obtained at Kisarazu was used as the fine aggregate. Hard crushed sand obtained at Tokyo Aoume (with a specific gravity of 2.64 and a MS (Maximum Size) of 20 mm) was used as the coarse aggregate. An air entraining agent (manufactured by NMB and marketed under the trade name of Pozzolith No. 303A) was used to adjust the amount of air entrainment in the concrete to which the cement dispersing agent (1) was added. Mixing of the concrete was performed using a forced mixing type mixer.

The results were that the amount of the cement dispersing agent (1) added to the cement was 0.10 percent in solid content, and the amount of air entraining agent added to the cement was 0.003 percent. The amount of the cement dispersing agent and the amount of the air entraining agent are respectively shown in Table 3.

By measuring changes in the slump value of the concrete and in the amount of entrained air with time, the slump maintaining ability and the air entraining ability of the concrete were evaluated. Moreover, the time taken for setting the concrete and the compressive strength of a test piece with a material age of 28 days (hereinafter referred to as 28-day compressive strength) were measured. Methods for measuring the slump value, the amount of air, the compressive strength and the setting time, and a method for collecting the test piece for measurement of the 28-day compressive strength were based on JIS (Japanese Industrial Standards) A 1101, 1108, 1128, 1132 and 6204). The results of the tests are shown together in Tables 4 and 5.

EXAMPLE 28

The same reaction as that of Example 27 was performed in the same manner except that 285 parts ethyl-α-(hydroxypolyethylene glycoxy methyl) acrylate (the average number of added moles of ethylene oxide was 10) as an oxyacrylate monomer was used instead of sodium-α-(hydroxypolyethylene glycoxy methyl) acrylate. Consequently, a copolymer aqueous solution as the polymer (F) was obtained. The weight-average molecular weight of the copolymer solution was 28,000.

Subsequently, after transferring the copolymer aqueous solution to a 1000 ml autoclave, 69 parts 48 percent sodium hydroxide as an alkaline substance was added, and hydrolyzing was performed for 6 hours at 150° C. Thereafter, by forming an azeotrope of water and ethyl alcohol generated by hydrolyzing and performing distillation, 70 parts distilled liquid was removed. Consequently, a copolymer aqueous solution as the polymer (G) was obtained as a cement dispersing agent of the present invention (hereinafter just referred to as the cement dispersing agent (2)).

Next, concrete was prepared by using the same method as in Example 27 except that the cement dispersing agent (2) was used instead of the cement dispersing agent (1).

The results were that the amount of the cement dispersing agent (2) added to the cement was 0.11 percent in solid content, and the amount of the air entraining agent added to the cement was 0.004 percent. The amount of the cement dispersing agent and the amount of entraining agent are shown together in Table 3.

By measuring changes in the slump value of the concrete and in the amount of entrained air with time, the slump maintaining ability and the air entraining ability of the concrete were evaluated. Moreover, the time taken for setting the concrete and the 28-day compressive strength were measured. The results of the tests are shown together in Tables 4 and 5.

Comparative Example 2

Comparative concrete was prepared by the same method as in Example 27 except that naphthalenesulfonic formalized condensate (NSF) was used as a comparative cement dispersing agent instead of the cement dispersing agent (1), and the same tests as in Example 27 were carried out.

The results were that the amount of the NSF added to the cement was 0.50 percent in solid content, and the amount of the air entraining agent added to the cement was 0.008 percent. The amount of the NSF and the amount of the air entraining agent are shown in Table 3.

By measuring changes in the slump value of the concrete and in the amount of entrained air with time, the slump maintaining ability and the air entraining ability of the comparative concrete were evaluated. Moreover, the time taken for setting the comparative concrete and the 28-day compressive strength were measured. The results of the tests are shown together in Tables 4 and 5.

Comparative Example 3

Comparative concrete was prepared by the same method as in Example 27 except that melaminesulfonic formalized condensate (MSF) was used as a cement dispersing agent instead of the cement dispersing agent (1), and the same tests as in Example 27 were carried out.

The results were that the amount of the MSF added to the cement was 0.60 percent in solid content, and the amount of the air entraining agent added to the cement was 0.002 percent. The amount of the MSF and the amount of the air entraining agent are shown in Table 3.

By measuring changes in the slump value of the comparative concrete and in the amount of entrained air with time, the slump maintaining ability and the air entraining ability of the comparative concrete were evaluated. Moreover, the time taken for setting the comparative concrete and the 28-day compressive strength were measured. The results of the tests are shown together in Tables 4 and 5.

Comparative Example 4

424 parts water was loaded and agitated in the same reaction vessel as in Example 27. Moreover, a monomeric composition formed by 200 parts methoxypolyethylene glycol monoacrylic ester (the average number of added moles of ethylene oxide was 10) as the other monomer, 50 parts methacrylic acid as a (meth)acrylic acid monomer of general formula (10) and by 375 parts water, and 42 parts 5 percent ammonium persulfate aqueous solution as a polymerization initiator were separately loaded in the dropping funnels. Subsequently, after performing nitrogen replacement, the temperature in the reaction vessel was brought to 95° C. under the atmosphere of nitrogen, and the monomeric composition and the 5 percent ammonium persulfate aqueous solution in the dropping funnels were respectively added dropwise into the reaction vessel in four hours.

Thereafter, 42 parts of the 5 percent ammonium persulfate aqueous solution was further added dropwise into the reaction vessel in one hour. Subsequently, the reaction solution was further agitated for 1 hour while keeping the temperature in the reaction vessel at 95° C. so as to complete a polymerization reaction. Consequently, a comparative copolymer aqueous solution was obtained as comparative cement dispersing agent (3). The weight-average molecular weight of the comparative copolymer aqueous solution was 35,000.

Next, comparative concrete was prepared by the same method as in Example 27 except that the comparative cement dispersing agent (3) was used instead of the cement dispersing agent (1), and the same tests as in Example 27 were carried out.

The results were that the amount of the comparative cement dispersing agent (3) added to the cement was 0.15 percent in solid content, and addition of the air entraining agent was not necessary. The amount of the comparative cement dispersing agent (3) is shown in Table 3.

By measuring changes in the slump value of the comparative concrete and in the amount of entrained air with time, the slump maintaining ability and the air entraining ability of the comparative concrete were evaluated. Moreover, the time taken for setting the comparative concrete and the 28-day compressive strength were measured. The results of the tests are shown together in Tables 4 and 5.

TABLE 3

| | Cement dispersing agent | | Air en-training agent |
|---|---|---|---|
| | Type | Amount (%) | Amount (%) |
| Example 27 | cement dispersing agent (1) | 0.10 | 0.003 |
| Example 28 | cement dispersing agent (2) | 0.11 | 0.004 |
| Comparative Example 2 | NSF | 0.50 | 0.008 |
| Comparative Example 3 | MSF | 0.60 | 0.002 |
| Comparative Example 4 | cement dispersing agent (3) | 0.15 | — |

TABLE 4

| | Slump value (cm)/Amount of entrained air (%) | | | |
|---|---|---|---|---|
| | Just after Aqitation | 30 min. later | 60 min. later | 90 min. later |
| Example 27 | 18.0/4.0 | 17.0/4.1 | 15.0/3.8 | 13.0/4.0 |
| Example 28 | 18.0/4.0 | 17.0/3.8 | 14.0/3.7 | 11.0/3.9 |
| Comparative Example 2 | 18.0/3.8 | 14.0/4.1 | 10.0/4.1 | |
| Comparative Example 3 | 17.5/4.0 | 15.5/4.0 | 11.5/3.7 | |
| Comparative Example 4 | 18.5/3.8 | 17.5/4.1 | 14.5/4.8 | 12.5/5.0 |

TABLE 5

| | Setting time (hours-minutes) | | 28-day compressive |
|---|---|---|---|
| | Start | End | strength (kg/cm$^2$) |
| Example 27 | 6-10 | 9-00 | 440 |
| Example 28 | 6-50 | 9-30 | 420 |
| Comparative Example 2 | 5-30 | 8-30 | 435 |
| Comparative Example 3 | 5-50 | 8-40 | 421 |
| Comparative Example 4 | 6-40 | 9-40 | 390 |

As is clear from the results shown in Tables 3–5, the concrete prepared by adding the cement dispersing agent (1) or the cement dispersing agent (2) of the present invention has superior slump maintaining ability compared to the comparative concrete formed by adding NSF or MSF. Moreover, the concrete of the present invention has more stable air entraining ability and higher strength compared to the comparative concrete formed by adding the cement dispersing agent (3). Furthermore, the cement dispersing agents (1) and (2) of the present invention can perform the same functions as NSF, MSF and the comparative cement dispersing agent (3) with reduced amounts with respect to cement.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An acrylic acid derivative represented by general formula (1)

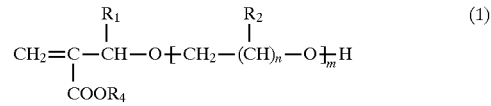

wherein $R_1$ and $R_2$ independently represent a hydrogen atom or an organic residue, $R_4$ represents a hydrogen atom or counter-ions, n is a positive number among 1 to 3, and m is a positive number among 1 to 100.

2. The acrylic acid derivative according to claim 1,
   wherein $R_1$ is a hydrogen atom, $R_2$ is selected from the group consisting of a hydrogen atom, methyl group and ethyl group, and $R_4$ is selected from the group consisting of a hydrogen atom, monovalent metal, bivalent metal, ammonium group and organic amine group.

3. A method for preparing an acrylic acid derivative represented by general formula (1)

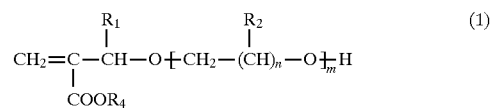

wherein $R_1$ and $R_2$ independently represent a hydrogen atom or an organic residue, $R_4$ represents a hydrogen atom or counter-ions, n is a positive number among 1 to 3, and m is a positive number among 1 to 100, comprising the step of
   hydrolyzing an acrylic acid derivative represented by general formula (2)

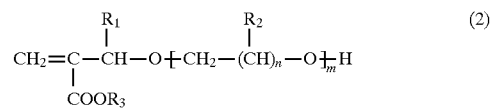

wherein $R_1$ and $R_2$ independently represent a hydrogen atom or an organic residue, $R_3$ represents an organic residue, n is a positive number among 1 to 3, and m is a positive number among 1 to 100.

4. The method for preparing an acrylic acid derivative according to claim 3,
   wherein a weight ratio of water used for hydrolyzing to the acrylic acid derivative of general formula (2) is within a range of from 0.001 to 1000.

5. The method for preparing an acrylic acid derivative according to claim 3,
   wherein hydrolyzing is carried out under the presence of a catalyst.

6. The method for preparing an acrylic acid derivative according to claim 5,
   wherein the catalyst is one compound selected from the group consisting of hydroxide of monovalent metal, metallic oxide of monovalent metal, hydroxide of bivalent metal, metallic oxide of bivalent metal, ammonia, tertiary amine, and protonic acid.

7. The method for preparing an acrylic acid derivative according to claim 5,
   wherein an amount of the catalyst used with respect to one mole of the acrylic acid derivative of general formula (2) is within a range of from 0.01 mole to 10 moles.

8. The method for preparing an acrylic acid derivative according to claim 3, wherein hydrolyzing is performed at a temperature within a range of from 0° C. to 150° C.

9. An acrylic acid derivative represented by general formula (2)

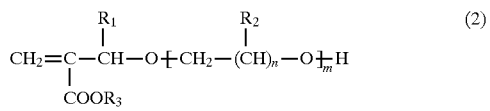

wherein $R_1$ and $R_2$ independently represent a hydrogen atom or an organic residue, $R_3$ represents an organic residue, n is a positive number among 1 to 3, and m is a positive number among 1 to 100.

10. The acrylic acid derivative according to claim 9, wherein $R_1$ is a hydrogen atom, $R_2$ is selected from the group consisting of a hydrogen atom, methyl group and ethyl group, and $R_3$ is an alkyl group having 1 to 18 carbons.

11. The acrylic acid derivative according to claim 9, wherein m is a positive number among 1 to 50.

12. A method for preparing an acrylic acid derivative represented by general formula (2)

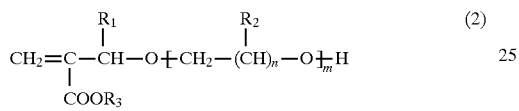

wherein $R_1$ and $R_2$ independently represent a hydrogen atom or an organic residue, $R_3$ represents an organic residue, n is a positive number among 1 to 3, and m is a positive number among 1 to 100, comprising the step of reacting an acrylic ester represented by general formula (3)

wherein $R_1$ represents a hydrogen atom or an organic residue, and $R_3$ represents an organic residue, with a cyclic ether compound represented by general formula (4)

wherein $R_2$ represents a hydrogen atom or an organic residue, and n is a positive number among 1 to 3.

13. The method for preparing an acrylic acid derivative according to claim 12, wherein said acrylic ester is at least one compound selected from the group consisting of methyl-α-hydroxymethyl acrylate, ethyl-α-hydroxymethyl acrylate, n-butyl-α-hydroxymethyl acrylate, and 2-ethylhexyl-α-hydroxymethyl acrylate.

14. The method for preparing an acrylic acid derivative according to claim 12, wherein said cyclic ether compound is at least one compound selected from the group consisting of ethylene oxide, propylene oxide, butylene oxide, and tetrahydrofuran.

15. The method for preparing an acrylic acid derivative according to claim 12, wherein an amount of said cyclic ether compound used with respect to one mole of said acrylic ester is within a range of from 1 mole to 100 moles.

16. The method for preparing an acrylic acid derivative according to claim 12, wherein the reaction is performed under the presence of a polymerization inhibitor.

17. The method for preparing an acrylic acid derivative according to claim 12, wherein the reaction is performed at a temperature within a range of from 0° C. to 150° C.

18. The method for preparing an acrylic acid derivative according to claim 12, wherein the reaction is performed under the presence of a catalyst.

19. The method for preparing an acrylic acid derivative according to claim 18, wherein an amount of said catalyst is within a range of from 0.001 weight percent to 10 weight percent of said acrylic ester.

20. The method for preparing an acrylic acid derivative according to claim 12, further comprising the step of removing said catalyst after the reaction.

21. A method for purifying an acrylic acid derivative which is represented by general formula (2)

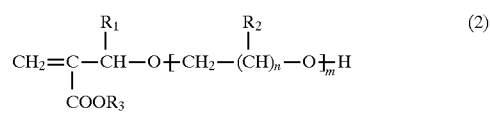

wherein $R_1$ and $R_2$ independently represent a hydrogen atom or an organic residue, $R_3$ represents an organic residue, n is a positive number among 1 to 3, and m is a positive number among 1 to 100, and which contains a crosslinking component having at least two double bonds in a molecule as an impurity, comprising the step of washing the acrylic acid derivative with an organic solvent (A) in which a solubility of said crosslinking component is higher than a solubility of said acrylic acid derivative.

22. The method for purifying an acrylic acid derivative according to claim 21, wherein washing includes the step of extracting said crosslinking component into a layer of said organic solvent (A).

23. The method for purifying an acrylic acid derivative according to claim 21, wherein a solubility parameter of said organic solvent (A) is not greater than 8.5.

24. The method for purifying an acrylic acid derivative which is represented by general formula (2)

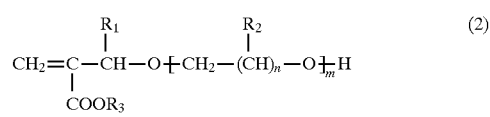

wherein $R_1$ and $R_2$ independently represent a hydrogen atom or an organic residue, $R_3$ represents an organic residue, n is a positive number among 1 to 3, and m is a positive number among 1 to 100, and which contains a crosslinking component having at least two double bonds in a molecule as an impurity, comprising the step of washing said acrylic acid derivative with a washing agent (I) containing at least water.

25. The method for purifying an acrylic acid derivative according to claim 24, wherein washing includes the step of separating said acrylic acid derivative from said crosslinking component by extracting said acrylic acid derivative into a layer of water.

26. The method for purifying an acrylic acid derivative according to claim 24,
wherein a weight ratio of water to said acrylic acid derivative is within a range of from 0.01 to 100.

27. The method for purifying an acrylic acid derivative according to claim 24,
wherein said washing agent (I) contains an organic solvent (B) which is separable from a layer of water, and a solubility parameter of said organic solvent (B) is not greater than 10.

28. The method for purifying an acrylic acid derivative according to claim 24,
wherein a weight ratio of the organic solvent (B) to said acrylic acid derivative is more than zero but not greater than 100.

29. A method for purifying an acrylic acid derivative which contains non-polymerizable alcohol as an impurity and is represented by general formula (6)

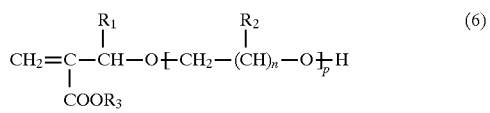

wherein $R_1$ and $R_2$ independently represent a hydrogen atom or an organic residue, $R_3$ represents an organic residue, n is a positive number among 1 to 3, and p is a positive number among 1 to 10, comprising the step of
washing said acrylic acid derivative with a washing agent (II) containing at least water.

30. The method for purifying an acrylic acid derivative according to claim 29,
wherein washing includes the step of separating said acrylic acid derivative from said non-polymerizable alcohol by extracting said non-polymerizable alcohol into a layer of water.

31. The method for purifying an acrylic acid derivative according to claim 29,
wherein a weight ratio of water to said acrylic acid derivative is within a range of from 0.001 to 100.

32. The method for purifying an acrylic acid derivative according to claim 29,
wherein said washing agent (II) contains an organic solvent (C) which is separable from a layer of water, and a solubility parameter of said organic solvent (C) is not smaller than 7.

33. The method for purifying an acrylic acid derivative according to claim 29,
wherein a weight ratio of said organic solvent (C) to said acrylic acid derivative is more than zero but not greater than 100.

34. An acrylic acid polymer having a structural unit represented by general formula (5)

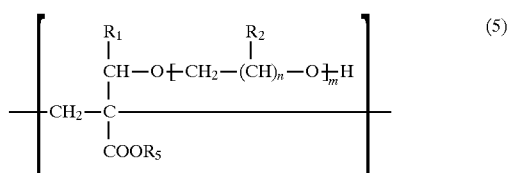

wherein $R_1$ and $R_2$ independently represent a hydrogen atom or an organic residue, $R_5$ represents a hydrogen atom, counter-ions or an organic residue, n is a positive number among 1 to 3, and m is a positive number among 1 to 100.

35. The acrylic acid polymer according to claim 34,
wherein a number-average molecular weight of said acrylic acid polymer is within a range of from 1,000 to 1,000,000.

36. A cement dispersing agent containing an acrylic acid polymer having a structural unit represented by general formula (7)

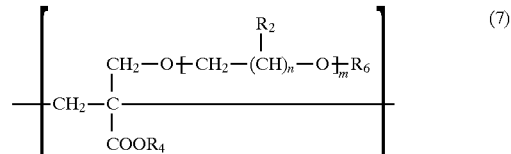

wherein $R_2$ and $R_6$ independently represent a hydrogen atom or an organic residue, $R_4$ represents a hydrogen atom or counter-ions, n is a positive number among 1 to 3, and m is a positive number among 1 to 100 representing the average number of added moles of oxyalkylene group.

37. The cement dispersing agent according to claim 36,
wherein $R_2$ is selected from the group consisting of a hydrogen atom and alkyl group having 1 to 8 carbons, $R_6$ is selected from the group consisting of a hydrogen atom, alkyl group having 1 to 8 carbons, and phenyl group, $R_4$ is selected from the group consisting of a hydrogen atom, monovalent metal, bivalent metal, ammonium group, and organic amine group.

38. The cement dispersing agent according to claim 36,
wherein a weight-average molecular weight of said acrylic acid polymer is within a range of from 1,000 to 500,000.

39. A cement dispersing agent containing at least one kind of acrylic acid polymer selected from the group consisting of an acrylic acid polymer (D) formed by polymerization of a monomeric composition (III) containing at least an acrylic acid derivative represented by general formula (8)

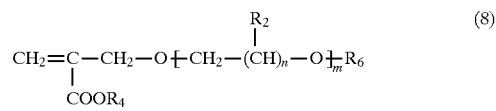

wherein $R_2$ and $R_6$ independently represent a hydrogen atom or an organic residue, $R_4$ represents a hydrogen atom or counter-ions, n is a positive number among 1 to 3, and m is a positive number among 1 to 100 representing the average number of added moles of oxyalkylene group; an acrylic acid polymer (E) formed by neutralizing said acrylic acid polymer (D) with an alkaline substance; and an acrylic acid polymer (G) formed by hydrolyzing with an alkaline substance an acrylic acid polymer (F) obtained by polymerization of a monomeric composition (IV) containing at least an acrylic acid derivative represented by general formula (9)

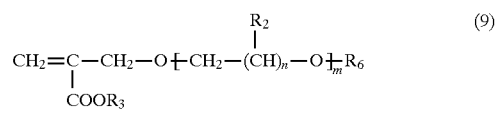

wherein $R_2$ and $R_6$ independently represent a hydrogen atom or an organic residue, $R_3$ represents an organic residue, n is a positive number among 1 to 3, and m is a positive number among 1 to 100 representing the average number of added moles of oxyalkylene group.

40. The cement dispersing agent according to claim 39,
wherein said acrylic acid derivative of general formula (8) is at least one kind of compound selected from the group consisting of α-(hydroxypolyethylene oxymethyl) acrylic ester and α-(methoxypolyethylene oxymethyl) acrylic ester, in which an average number of added moles of oxyalkylene group is within a range of from 5 to 100, and monovalent metallic salts thereof.

41. The cement dispersing agent according to claim 39, wherein said acrylic acid derivative of general formula (9) is at least one kind of compound selected from the group consisting of alkyl-α-(hydroxypolyethylene oxymethyl) acrylic ester and alkyl-α-(methoxypolyethylene oxymethyl) acrylic ester, in which an average number of added moles of oxyalkylene group is within a range of from 5 to 100, and monovalent metallic salts thereof.

42. The cement dispersing agent according to claim 39, wherein said monomeric composition (III) further contains a (meth)acrylic acid monomer represented by general formula (10)

wherein $R_7$ represents a hydrogen atom, methyl group or —$CH_2OH$ group, and $R_8$ represents a hydrogen atom or counter-ions.

43. The cement dispersing agent according to claim 42, wherein said (meth)acrylic acid monomer of general formula (10) is a compound wherein $R_8$ is selected from the group consisting of a hydrogen atom, monovalent metal, bivalent metal, ammonium group, and organic amine group.

44. The cement dispersing agent according to claim 42, wherein said acrylic acid polymer (D) is formed by said acrylic acid derivative of general formula (8) and said (meth)acrylic acid monomer of general formula (10), in which an amount of said acrylic acid derivative of general formula (8) is within a range of from 20 weight percent to 100 weight percent and an amount of said (meth)acrylic acid monomer of general formula (10) is within 0 weight percent to 80 weight percent.

45. The cement dispersing agent according to claim 39, wherein said acrylic acid polymer (D) is formed by said acrylic acid derivative of general formula (8), a (meth) acrylic acid monomer represented by general formula (10)

wherein $R_7$ represents a hydrogen atom, methyl group or —$CH_2OH$ group, and $R_8$ represents a hydrogen atom or counter-ions, and other monomer other than said acrylic acid derivative of general formula (8) and said (meth)acrylic acid monomer of general formula (10), in which an amount of said acrylic acid derivative of general formula (8) is within a range of from 1 weight percent to 100 weight percent, an amount of said (meth)acrylic acid derivative of general formula (10) is within a range of from 0 weight percent to 99 weight percent, and an amount of said other monomer is within a range of from 0 weight percent to 50 weight percent, a total amount thereof being 100 weight percent.

46. The cement dispersing agent according to claim 39, wherein said monomeric composition (IV) further contains at least one kind of (meth)acrylic acid monomer selected from the group consisting of a (meth)acrylic acid monomer represented by general formula (10)

wherein $R_7$ represents a hydrogen atom, methyl group or —$CH_2OH$ group, and $R_8$ represents a hydrogen atom or counter-ions, and a (meth)acrylic acid monomer represented by general formula (11)

wherein $R_9$ represents a hydrogen atom, methyl group or —$CH_2OH$ group, and $R_{10}$ represents an organic residue.

47. The cement dispersing agent according to claim 46, wherein said (meth)acrylic acid monomer of general formula (10) is a compound in which $R_8$ is selected from the group consisting of a hydrogen atom, monovalent metal, bivalent metal, ammonium group, and organic amine group.

48. The cement dispersing agent according to claim 46, wherein said (meth)acrylic acid monomer of general formula (11) is a compound in which $R_{10}$ is an alkyl group having 1 to 8 carbons.

49. The cement dispersing agent according to claim 46, wherein said acrylic acid polymer (F) is formed by said acrylic acid derivative of general formula (9), and said (meth)acrylic acid monomer of general formula (10), in which an amount of said acrylic acid derivative of general formula (9) is within a range of from 20 weight percent to 100 weight percent, and an amount of said (meth)acrylic acid monomer of general formula (10) is within a range of from 0 weight percent to 80 weight percent.

50. The cement dispersing agent according to claim 39, wherein said acrylic acid polymer (F) is formed by said acrylic acid derivative of general formula (9), a (meth) acrylic acid monomer represented by general formula (10)

wherein $R_7$ represents a hydrogen atom, methyl group or —$CH_2OH$ group, and $R_8$ represents a hydrogen atom or counter-ions), a (meth)acrylic acid monomer represented by general formula (11)

wherein $R_9$ represents a hydrogen atom, methyl group or —$CH_2OH$ group, and $R_{10}$ represents an organic residue, and other monomer other than said acrylic acid derivative of general formula (8), said (meth)acrylic acid monomer of general formula (10) and said (meth)acrylic acid monomer of general formula (11), in which an amount of said acrylic acid derivative of general formula (9) is within a range of from 1 weight percent to 100 weight percent, and an amount of said (meth)acrylic acid monomer of general formula (10) is within a range of from 0 weight percent to 90 weight percent, an amount of said (meth)acrylic acid monomer of general formula (11) is within a range of from 0 weight percent to 90 weight percent, and an amount of said other monomer is within a range of from 0 weight percent to 50 weight percent, a total amount thereof being 100 weight percent.

51. A cement composition comprising at least:

cement;

water; and a cement dispersing agent containing an acrylic acid polymer having a structural unit represented by general formula (7)

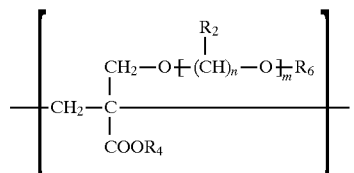

wherein $R_2$ and $R_6$ independently represent a hydrogen atom or an organic residue, $R_4$ represents a hydrogen atom or counter-ions, n is a positive number among 1 to 3, and m is a positive number among 1 to 100 representing an average number of added moles of oxyalkylene group.

52. A method for preparing an acrylic acid derivative represented by general formula (12)

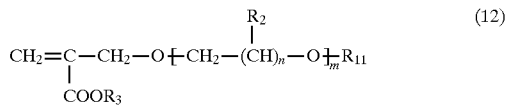

wherein $R_2$ represents a hydrogen atom or an organic residue, $R_3$ and $R_{11}$ independently represent an organic residue, n is a positive number among 1 to 3, and m is a positive number among 1 to 100 representing an average number of added moles of oxyalkylene group, comprising the step of reacting an acrylic ester represented by general formula (13)

wherein $R_3$ represents an organic residue, with a compound containing a hydroxyl group, represented by general formula (14)

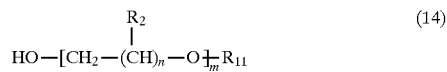

wherein $R_2$ represents a hydrogen atom or an organic residue, $R_{11}$ represents an organic residue, n is a positive number among 1 to 3, and m is a positive number among 1 to 100, under the presence of an acid catalyst, a polymerization inhibitor, and molecular oxygen.

* * * * *